United States Patent
Letourneau et al.

(10) Patent No.: US 7,365,209 B2
(45) Date of Patent: Apr. 29, 2008

(54) NITROGEN HETEROCYCLE BIARYLS FOR OSTEOPOROSIS AND OTHER DISEASES

(75) Inventors: Jeffrey John Letourneau, East Windsor, NJ (US); Vidyahar Paradkar, Somerville, NJ (US); Michael H. J. Ohlmeyer, Plainsboro, NJ (US); Lawrence W. Dillard, Yardley, PA (US); John J. Baldwin, Gwynedd Valley, PA (US); Christopher Mark Riviello, Morrisville, PA (US); Angela Wong, North Wales, PA (US); Yaing Rong, Monmouth Junction, NJ (US)

(73) Assignee: Pharmacopeia, Inc., Cranbury, NJ (US)

( * ) Notice: Subject to any disclaimer, the term of this patent is extended or adjusted under 35 U.S.C. 154(b) by 504 days.

(21) Appl. No.: 10/775,963

(22) Filed: Feb. 10, 2004

(65) Prior Publication Data

US 2005/0222203 A1    Oct. 6, 2005

Related U.S. Application Data

(60) Provisional application No. 60/446,418, filed on Feb. 11, 2003.

(51) Int. Cl.
    *A61K 31/405*    (2006.01)
    *A01N 43/38*     (2006.01)
    *C07D 235/00*    (2006.01)

(52) U.S. Cl. ............... 548/304.4; 548/301.7; 548/302.7; 514/410; 514/412; 514/415

(58) Field of Classification Search ............ 548/301.7, 548/302.7, 304.4; 514/410, 412, 415
See application file for complete search history.

(56) References Cited

U.S. PATENT DOCUMENTS

| | | | |
|---|---|---|---|
| 6,306,819 B1 | 10/2001 | Rupnick et al. ............ 514/2 |
| 2005/0222203 A1 | 10/2005 | Letourneau et al. | |

FOREIGN PATENT DOCUMENTS

| | | | |
|---|---|---|---|
| CA | 1031780 | 5/1978 | |
| WO | WO97/19934 | 6/1997 | ........... 241/44 |
| WO | WO98/31359 | 7/1998 | |
| WO | WO 02/44156 | 6/2002 | |
| WO | WO 02/081467 | 10/2002 | |

*Primary Examiner*—Bruck Kifle
*Assistant Examiner*—Paul V. Ward
(74) *Attorney, Agent, or Firm*—Heslin Rothenburg Farley & Mesiti P.C.

(57) ABSTRACT

Nitrogen heterocycle biaryls having a carboxylate terminus are useful for treating endometriosis, osteoporosis, restenosis following angioplasty, rheumatoid arthritis, cancer, macular degeneration and obesity.

Compounds of formula:

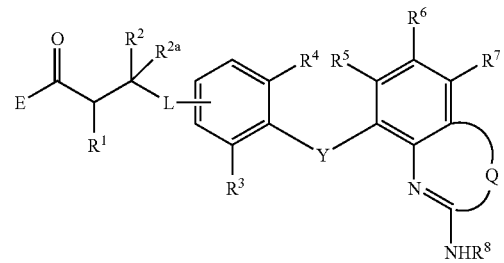

are disclosed. A representative example is

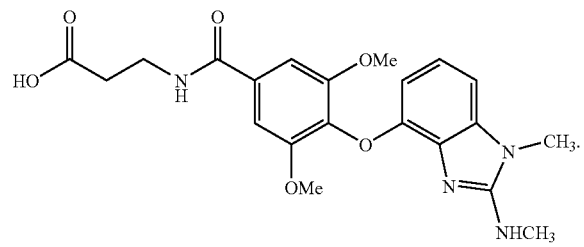

25 Claims, No Drawings

NITROGEN HETEROCYCLE BIARYLS FOR OSTEOPOROSIS AND OTHER DISEASES

CROSS REFERENCE TO RELATED APPLICATIONS

This application claims priority from a U.S. provisional application Ser. No. 60/446,418, filed Feb. 11, 2003, the entire disclosure of which is incorporated herein by reference.

FIELD OF THE INVENTION

The invention relates to a genus of nitrogen heterocycle biaryls having a carboxylate terminus. The nitrogen heterocycle biaryls are useful for treating endometriosis, osteoporosis, restenosis following angioplasty, rheumatoid arthritis, cancer, macular degeneration and obesity.

BACKGROUND OF THE INVENTION

Integrins are a superfamily of heterodimeric transmembrane glycoproteins that function in cellular adhesion, migration and signal transduction. These glycoproteins consist of an $\alpha$ and a $\beta$-subunit, which associate non-covalently in defined combinations. To date, 17 $\alpha$-subunits and eight $\beta$-subunits have been identified, which associate selectively to form at least 23 integrins, all of which appear to function as receptors.

The integrin $\alpha_v\beta_3$, also referred to as the vitronectin receptor, is expressed on a variety of cell types, including osteoclasts, vascular smooth muscle cells, endothelial cells and various tumor cells. In general, the level of expression of $\alpha_v\beta_3$ integrin is low on most cell types but it is greatly increased in remodeling or growing tissues. Consistent with its expression profile, $\alpha_v\beta_3$ integrin mediates several biologically relevant processes, such as adhesion of osteoclasts to bone, vascular smooth muscle cell migration and angiogenesis. As a result, vitronectin receptor antagonists are useful for the treatment of endometriosis, osteoporosis, restenosis following percutaneous transluminal coronary angioplasty (PTCA), rheumatoid arthritis, cancer and ocular diseases [see, e.g., Miller et al., *Identification and in vivo efficacy of small-molecule antagonists of integrin $\alpha_v\beta_3$ (the vitronectin receptor)*, Drug Discovery Today, Vol, 5, No. 9, 397-408 (2000)].

Osteoporosis is a debilitating bone disease characterized by a decrease in bone mass (osteopenia) leading to an increased risk of fracture. The osteopenia associated with osteoporosis arises from an imbalance between bone resorption and formation, such that resorption exceeds formation. For bone resorption to occur, the bone-resorbing osteoclasts must first adhere to the bone matrix and this key adhesive event is mediated by $\alpha_v\beta_3$ integrin. Disruption of osteoclast adhesion inhibits bone resorption both in vitro and in vivo and provides a therapeutic approach to the treatment and/or prevention of osteoporosis [see, Miller et al. (2000)].

Angiogenesis (the formation of new blood vessels) involves the $\alpha_v\beta_3$ integrin mediated migration and proliferation of endothelial cells. Significantly, the vitronectin receptor is upregulated only in growing vessels and not in mature ones. Thus, vitronectin antagonists are useful in the treatment of diseases characterized by excessive or undesirable angiogenesis, such as cancer, rheumatoid arthritis, diabetic retinopathy and macular degeneration. In support of this hypothesis, vitronectin-selective antibodies and peptides have been shown to be effective inhibitors of angiogenesis [see, Miller et al. (2000)].

U.S. Pat. No. 6,306,819 describes the use of angiogenesis inhibitors in vivo for obesity, intestinal polyps, cardiac hypertrophy, and endometriosis. Initial studies conducted in genetically obese mice showed that inhibition of angiogenesis led to reduction in adipose tissue mass. Weight gain in animals receiving angiogenesis inhibitors was significantly reduced, in spite of increases in appetite sufficient to cause weight gain in paired-fed mice. Discontinuation of the inhibitor resulted in rapid expansion of the adipose tissue. The effect was dose-dependent, repeatedly reversible, and occurred in response to all of the inhibitors tested. Significant inhibition was also observed in both the intestinal polyp and cardiac hypertrophy animal models. Results in vivo in an endometriosis model also showed decreased development of endometriosis in animals treated with angiogenesis inhibitors.

Rheumatoid arthritis is a debilitating, systemic autoimmune disease in which there is massive bone and cartilage destruction within articulating joints. Integrin $\alpha_v\beta_3$ is expressed on the vessels within the invasive pannus and appears to play a role in angiogenic vessel formation within the highly invasive hypertrophic synovium. In addition, vitronectin mediates the bone resorption process. Because rheumatoid arthritis involves both angiogenic vessel formation and bone resorption, vitronectin antagonists provide therapy for rheumatoid arthritis. A cyclic $\alpha_v\beta_3$ integrin inhibitor (an Arg-Gly-Asp peptide) has been shown to be effective in vivo in a rabbit model of inflammatory arthritis [see, Miller et al. (2000)].

Restenosis refers to a significant, delayed loss of blood vessel lumen that generally occurs after percutaneous transluminal coronary angioplasty (PTCA). Vascular smooth muscle cell migration into the neointima is a necessary step in restenosis and $\alpha_v\beta_3$ integrin, which is expressed on smooth muscle cells, has been shown to mediate this migration. In addition, vascular injury induced by PTCA causes a rapid, persistent and coordinated upregulation of $\alpha_v\beta_3$, $\alpha_v\beta_5$ and osteopontin during the period of neointimal development. Studies have shown that blocking the vitronectin receptor inhibits smooth muscle cell migration and that both peptide antagonists and a humanized monoclonal antibody are effective in reducing neointimal hyperplasia following arterial injury in vivo [see, Miller et al. (2000)]. Based on these findings, persons of skill accept that vitronectin antagonists would be useful for the treatment of restenosis following PTCA.

SUMMARY OF THE INVENTION

In one aspect the invention relates to compounds of formula I:

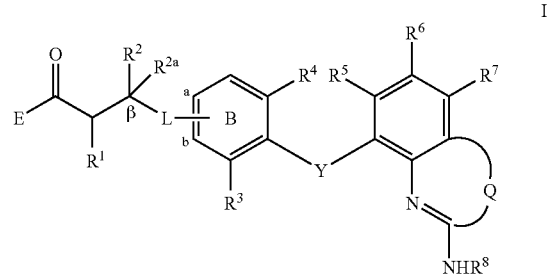

wherein

Y is chosen from the group consisting of —O—, —S—, —SO$_2$—, —CH$_2$— and —N(loweralkyl)-;

L is a linker. The linker comprises from one to eight carbons and from zero to three nitrogens, sulfurs and oxygens. At least two atoms are interposed between ring B and carbon β. The linker may be straight chain, branched or cyclic and, when cyclic, is either attached at carbons a and b of ring B or, when $R^1$ is methylene, it may be attached at $R^1$ to form a four, five or six membered ring;

Q is chosen from O, S, CH=N, N=CH, CH=CH and $NR^9$;

E is hydroxy, or E is a biolabile residue such that E and the carboxyl to which it is attached together form an ester or amide cleavable in vivo to provide a compound in which E is hydroxy;

$R^1$ is chosen from the group consisting of hydrogen, aryl, heteroaryl, ($C_1$ to $C_6$)hydrocarbon, substituted aryl, $C_1$ to $C_3$ alkylaryl, —$NHCOOR^{10}$, —$NHSO_2R^{10}$ and —NH-$COR^{10}$; when $R^1$ is methylene (i.e. a divalent $C_1$ hydrocarbon) it provides the point of attachment for a cyclic linker L;

$R^2$ is chosen from the group consisting of hydrogen, aryl, heteroaryl, $C_1$ to $C_6$ hydrocarbon, substituted aryl, $C_1$ to $C_3$ alkylaryl, —$NHCOOR^{10}$, —$NHSO_2R^{10}$ and —NH-$COR^{10}$, and $R^{2a}$ is hydrogen; or taken together $R^2$ and $R^{2a}$ a form a carbonyl;

$R^3$ and $R^4$ are independently chosen from the group consisting of hydrogen, $C_1$ to $C_4$ hydrocarbon, loweralkoxy, halogen and fluoro(loweralkyl);

$R^5$, $R^6$ and $R^7$ are independently chosen from the group consisting of hydrogen, halogen and fluoro(loweralkyl);

$R^8$ is chosen from hydrogen and lower alkyl; and $R^9$ is chosen from hydrogen, alkyl, substituted alkyl, aryl and $C_1$ to $C_3$ alkylaryl; or taken together $R^8$ and $R^9$ represent a two to four carbon chain forming a five to seven membered cyclic structure, which may contain one degree of unsaturation; and $R^{10}$ is chosen from the group consisting of alkyl, substituted alkyl, aryl and $C_1$ to $C_3$ alkylaryl.

In another aspect, the invention relates to a method of treating a condition that is associated with excessive vitronectin receptor activity by administering a therapeutically effective amount of a compound of the foregoing formula. Conditions associated with excessive vitronectin receptor activity include: endometriosis, osteoporosis, restenosis following angioplasty, rheumatoid arthritis, cancer, macular degeneration and obesity.

DETAILED DESCRIPTION OF THE INVENTION

The invention relates to compounds of formula I:

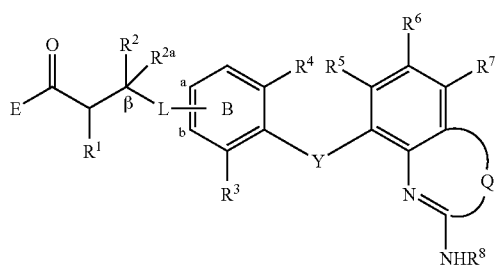

I

One embodiment includes subgenera in which L forms a fused ring with ring B, such as the subgenus of formula:

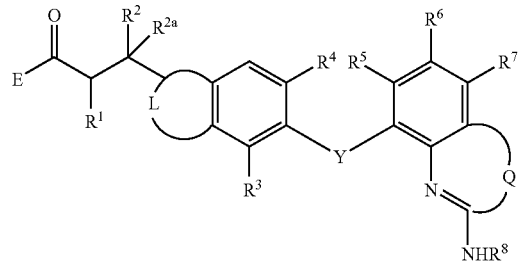

in which L is a cyclic linker forming a five-, six or seven-membered ring. The ring formed by L may be substituted with one or two substituents, preferably lower alkyl and/or oxo. Particularly preferred compounds having cyclic L may be described by the subgeneric formula:

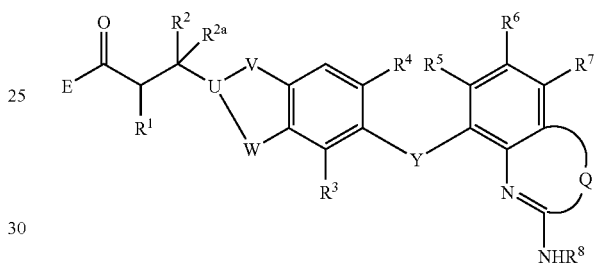

in which U is CH, C($CH_3$) or N; V is C=O, $CH_2$ or O; W is $(CH_2)_nC=O$, $C(=O)(CH_2)_n$, $(CH_2)_nCH_2$, $O(CH_2)_n$ or $(CH_2)_nO$; and n is zero, one or two. Examples of these include:

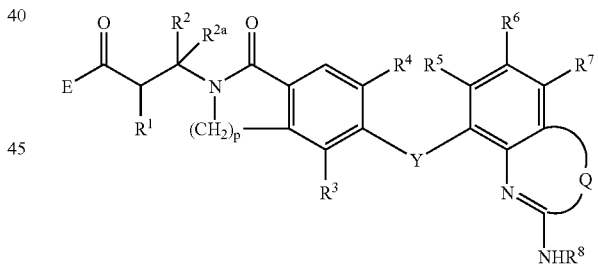

in which p is one, two or three;

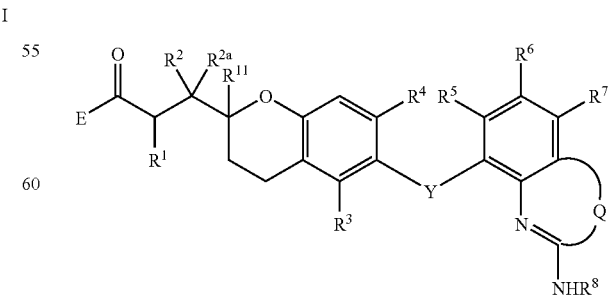

in which $R^{11}$ is hydrogen or methyl;

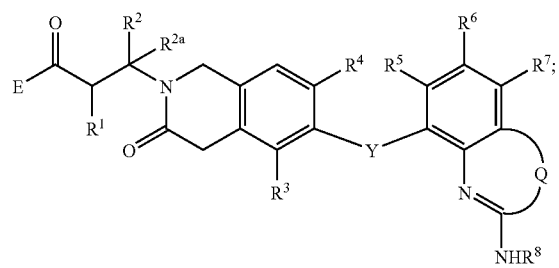
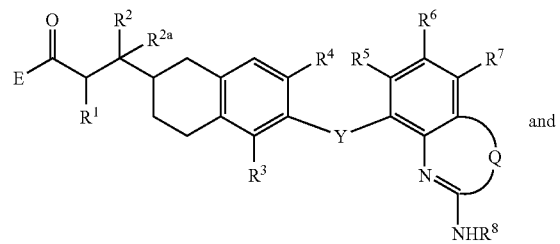
and
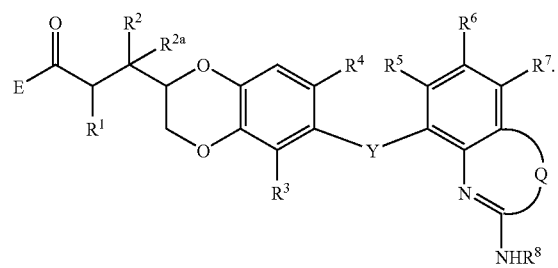
Examples of cyclic L are:
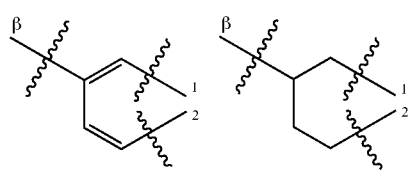
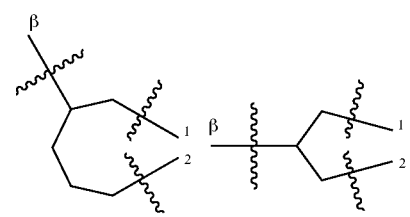
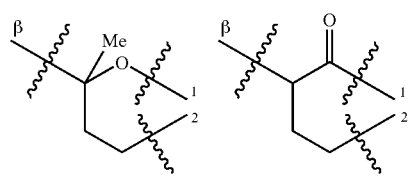
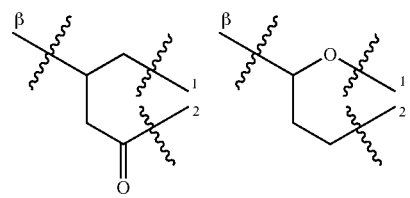
-continued
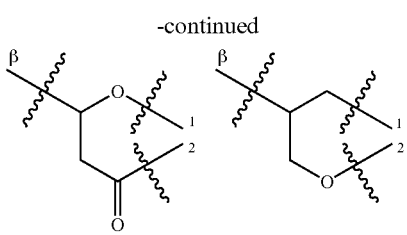
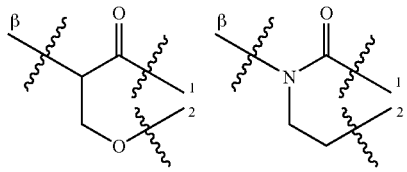
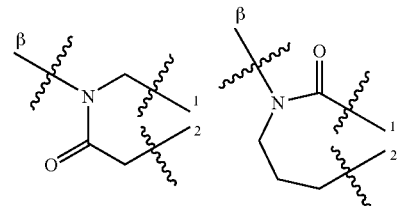
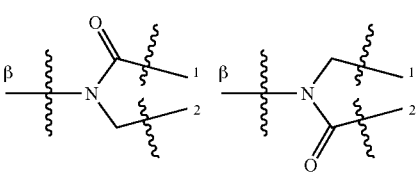
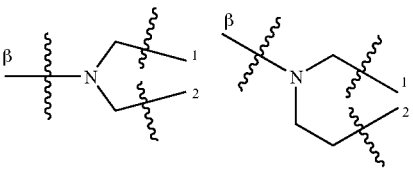
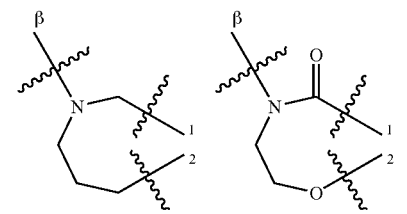
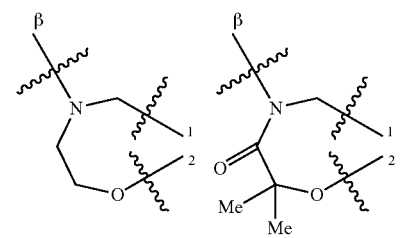
Another embodiment includes subgenera in which L, by attaching through $R^1$, forms a ring incorporating the β carbon. These subgenera are represented by the formula:

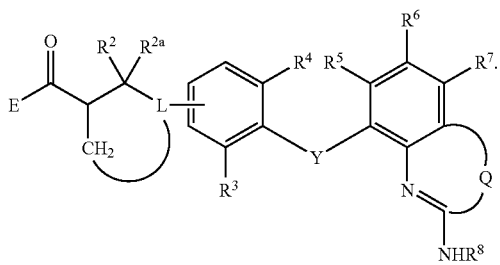

A preferred subgenus is that of formula:

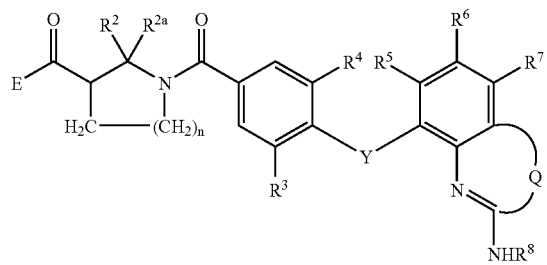

in which n is zero, one or two.

In another preferred embodiment, L may be an acyclic residue of one to four carbons and from zero to three nitrogens, sulfurs and oxygens, in a straight or branched chain, para to Y:

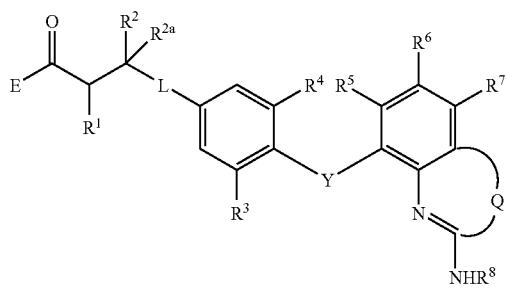

or from one to eight carbons and from zero to three nitrogens, sulfurs and oxygens, in a straight or branched chain meta to Y:

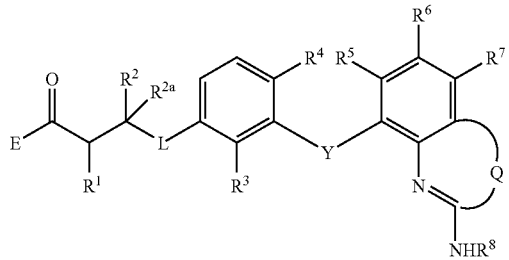

Examples of acyclic L are $CH_2CH_2$, $CH=CH$, cyclopropane, amide, N(Loweralkyl) amide, $OCH_2$, sulfonamide, N(Loweralkyl) sulfonamide. Preferred compounds are those in which L is —C(=O)NH—, —CH=CH— or —$CH_2CH_2$—.

Preferred subgenera of "Q" include compounds of formula:

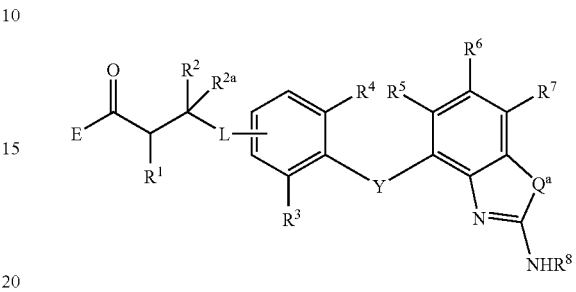

in which $Q^a$ is O, S, CH=N, N=CH, CH=CH or $NR^9$, and $R^9$ is hydrogen, alkyl, aryl, $(C_1-C_3)$alkylaryl or alkyl substituted with methoxy, fluoro or hydroxy. Particularly preferred ring systems are:

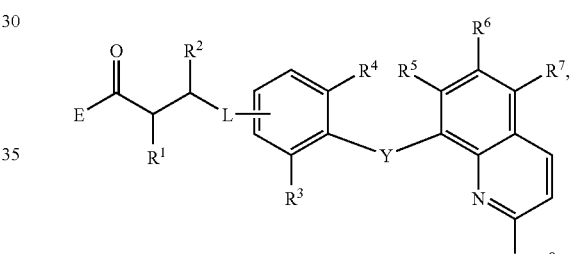

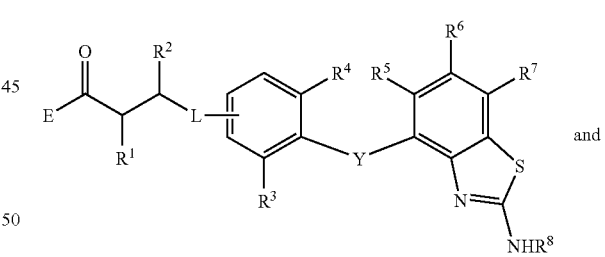

and

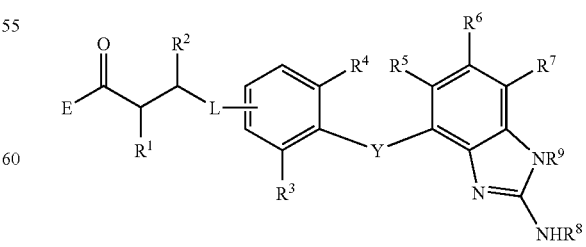

wherein $R^9$ is chosen from hydrogen, lower alkyl, and fluoro(loweralkyl); and

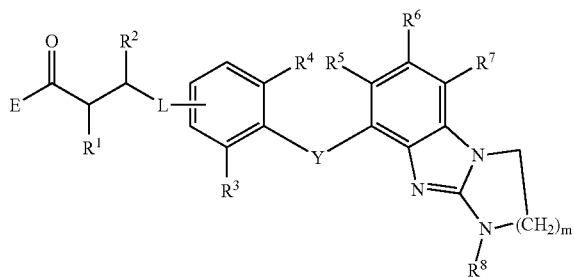

wherein m is one or two. A particularly preferred subgenus is the subgenus in which a cyclic linker in combined with a cyclic structure formed from $R^8$ and $R^9$:

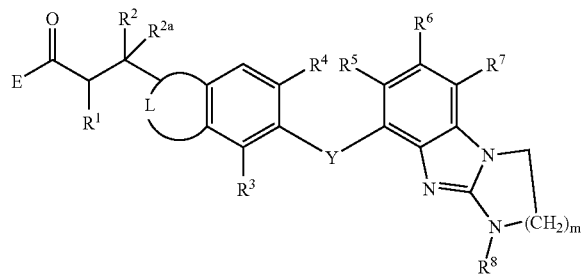

wherein m is one or two.

An example of such a particularly preferred subgenus is:

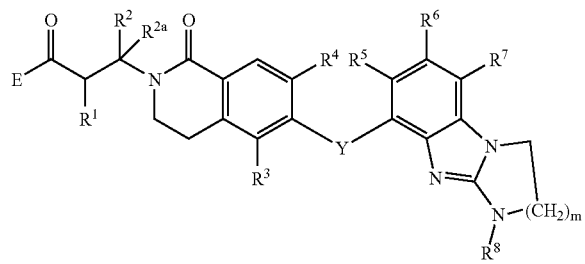

wherein m is one or two.

As described above, E may be hydroxy or a biolabile residue. The active drug substance appears to be the carboxylic acid, i.e. E is hydroxy. However, the invention also encompasses prodrugs of the active carboxylic acids. The concept of a prodrug is well established in the art (see for example U.S. Pat. Nos. 6,166,089; 5,681,964 and 4,235,887, the disclosures of which are incorporated herein by reference). In the compounds that function as prodrugs, E and the carboxyl to which it is attached together form an ester or amide cleavable in vivo to provide a compound in which E is hydroxy.

Turning to the two-carbon chain between the carboxylate and the linker L, preferred compounds are those in which $R^2$ is hydrogen, $C_1$-$C_6$ hydrocarbon, aryl, substituted aryl or heteroaryl; $R^{2a}$ is hydrogen and $R^1$ is hydrogen, —NHCOOR$^{10}$, —NHCOR$^{10}$ or —NHSO$_2$R$^{10}$. When $R^1$ is other than hydrogen, the preferred stereochemistry of the carbon to which $R^1$ is attached is of the configuration shown:

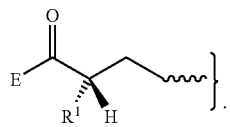

When $R^1$ is hydrogen, $R^{2a}$ is hydrogen and $R^2$ is other than hydrogen, the preferred stereochemistry of the carbon to which $R^2$ is attached is of the configuration shown:

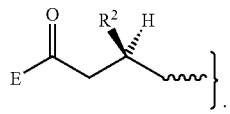

It is preferred that only one of $R^1$ and $R^2$ be other than hydrogen.

Among the ring substituents, preferred values for $R^3$ and $R^4$ are hydrogen, methyl, methoxy, halogen or trifluoromethyl; for $R^5$ and $R^7$, hydrogen; for $R^8$, hydrogen or methyl; and for Y, oxygen. The most preferred subgenus is that in which E is hydroxy; $R^1$ is hydrogen, —NHCOOR$^{10}$ or —NHCOR$^{10}$; $R^2$ is hydrogen, aryl, heteroaryl or substituted aryl; $R^3$ and $R^4$ are chosen from hydrogen, methyl, methoxy, halogen and trifluoromethyl; $R^5$ and $R^7$ are hydrogen; and $R^8$ is chosen from hydrogen and methyl.

The present invention includes compounds of formula (I) in the form of salts. Suitable salts include those formed with both organic and inorganic acids. Such acid addition salts will normally be pharmaceutically acceptable, although salts of non-pharmaceutically acceptable salts may be of utility in the preparation and purification of the compound in question. The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfueric, tartaric acid, p-toluenesulfonic, and the like. When the compounds contain an acidic side chain, suitable pharmaceutically acceptable base addition salts for the compounds of the present invention include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine.

While it may be possible for the compounds of formula (I) or their salts and solvates to be administered as the raw chemical, it is preferable to present them as a pharmaceutical composition. According to a further aspect, the present invention provides a pharmaceutical composition comprising a compound of formula (I) or a pharmaceutically acceptable salt or solvate thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association a compound of formula (I) or a pharmaceutically acceptable salt or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose or multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

Formulations for rectal administration may be presented as a suppository with the usual carriers, such as cocoa butter or polyethylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

Preferred unit dosage formulations are those containing an effective dose, or an appropriate fraction thereof, of the active ingredient.

The pharmaceutical compositions will usually include a "pharmaceutically acceptable inert carrier" and this expression is intended to include one or more inert excipients, which include starches, polyols, granulating agents, microcrystalline cellulose, diluents, lubricants, binders, disintegrating agents, and the like. If desired, tablet dosages of the disclosed compositions may be coated by standard aqueous or nonaqueous techniques. "Pharmaceutically acceptable carrier" also encompasses controlled release means. Compositions of the present invention may also optionally include other therapeutic ingredients, anti-caking agents, preservatives, sweetening agents, colorants, flavors, desiccants, plasticizers, dyes, and the like.

The compounds of formula (I) are preferably administered orally or by injection (intravenous or subcutaneous). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

Definitions

Throughout this specification the terms and substituents retain their definitions.

Alkyl is intended to include linear, branched, or cyclic hydrocarbon structures and combinations thereof. Lower alkyl refers to alkyl groups of from 1 to 6 carbon atoms. Examples of lower alkyl groups include methyl, ethyl, propyl, isopropyl, butyl, s- and t-butyl and the like. Preferred alkyl groups are those of $C_{20}$ or below. Cycloalkyl is a subset of alkyl and includes cyclic hydrocarbon groups of from 3 to 8 carbon atoms. Examples of cycloalkyl groups include c-propyl, c-butyl, c-pentyl, norbornyl and the like.

($C_1$ to $C_n$)Hydrocarbon includes alkyl, cycloalkyl, alkenyl, alkynyl, aryl and combinations thereof containing only hydrogen and one to n carbons. Examples include vinyl, allyl, cyclopropyl, propargyl, phenethyl, cyclohexylmethyl, camphoryl and naphthylethyl.

Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons.

Oxaalkyl refers to alkyl residues in which one or more carbons (and their associated hydrogens) have been replaced by oxygen. Examples include methoxypropoxy, 3,6,9-trioxadecyl and the like. The term oxaalkyl is intended as it is understood in the art [see Naming and Indexing of Chemical Substances for Chemical Abstracts, published by the American Chemical Society, ¶196, but without the restriction of ¶127(a)], i.e. it refers to compounds in which the oxygen is bonded via a single bond to its adjacent atoms (forming ether bonds); it does not refer to doubly bonded oxygen, as would be found in carbonyl groups.

Acyl refers to groups of from 1 to 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to four carbons.

Aryl and heteroaryl mean a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or a tricyclic 13- or 14-membered aromatic or heteroaromatic ring system containing 0-3 heteroatoms selected from O, N, or S. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Alkylaryl means an alkyl residue attached to an aryl ring. Examples of $C_1$-$C_3$ alkylaryl are benzyl, phenethyl, phenylpropyl and naphthylethyl. Alkylheteroaryl means an alkyl residue attached to a heteroaryl ring. Examples include, e.g., pyridinylmethyl, pyrimidinylethyl and the like.

Heterocycle means a cycloalkyl or aryl residue in which from one to three carbons is replaced by a heteroatom selected from the group consisting of N, O and S. The nitrogen and sulfur heteroatoms may optionally be oxidized, and the nitrogen heteroatom may optionally be quaternized. Examples of heterocycles that fall within the scope of the invention include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. It is to be noted that heteroaryl is a subset of heterocycle in which the heterocycle is aromatic. Examples of heterocyclyl residues additionally include piperazinyl, 2-oxopiperazinyl, 2-oxopiperidinyl, 2-oxo-pyrrolidinyl, 2-oxoazepinyl, azepinyl, 4-piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl, benzothienyl, thiamorpholinyl, thiamorpholinylsulfoxide, thiamorpholinylsulfone, oxadiazolyl, triazolyl and tetrahydroquinolinyl.

Substituted alkyl, aryl, cycloalkyl, heterocyclyl etc. refer to alkyl, aryl, cycloalkyl, or heterocyclyl wherein up to three H atoms in each residue are replaced with halogen, haloalkyl, hydroxy, loweralkoxy including alkylene dioxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy.

The term "halogen" means fluorine, chlorine, bromine or iodine.

The term "oxo", when referring to a substituent, means an oxygen double bonded to a carbon, e.g. a ketone or amide carbonyl.

As used herein, reference to "treatment" or "treating" a patient are intended to include prophylaxis. The terms include amelioration, prevention and relief from the symptoms and/or effects associated with these disorders. The terms "preventing" or "prevention" refer to administering a medicament beforehand to forestall or obtund an attack. Persons of ordinary skill in the medical art (to which the present method claims are directed) recognize that the term "prevent" is not an absolute term. In the medical art it is understood to refer to the prophylactic administration of a drug to diminish the likelihood or seriousness of a condition, and this is the sense intended.

The graphic representations of racemic, ambiscalemic and scalemic or enantiomerically pure compounds used herein are taken from Maehr J. Chem. Ed. 62, 114-120 (1985): solid and broken wedges are used to denote the absolute configuration of a chiral element; wavy lines indicate disavowal of any stereochemical implication which the bond it represents could generate; solid and broken bold lines are geometric descriptors indicating the relative configuration shown but denoting racemic character; and wedge outlines and dotted or broken lines denote enantiomerically pure compounds of indeterminate absolute configuration. Thus, among the structures below, those having open wedges are intended to encompass both of the pure enantiomers of that pair, those having solid wedges are intended to encompass the single, pure enantiomer having the absolute stereochemistry shown.

Abbreviations

The following abbreviations and terms have the indicated meanings throughout:

Ac=acetyl
ACN=acetonitrile
Bn=benzyl
BNB=4-bromomethyl-3-nitrobenzoic acid
Boc=t-butyloxy carbonyl
Bu=butyl
CBZ=carbobenzoxy=benzyloxycarbonyl
DBU=diazabicyclo[5.4.0]undec-7-ene
DCM=dichloromethane=methylene chloride=$CH_2Cl_2$
DEAD=diethyl azodicarboxylate
DIC=diisopropylcarbodiimide
DIEA=N,N-diisopropylethyl amine
DIPEA=N,N-diisopropylethyl amine
DMAP=4-N,N-dimethylaminopyridine
DME=dimethoxyethane
DMF=N,N-dimethylformamide
DMSO=dimethyl sulfoxide
DVB=1,4-divinylbenzene
EDC=ethylene dichloride=1,2-dichloroethane
EEDQ=2-ethoxy-1-ethoxycarbonyl-1,2-dihydroquinoline
Et=ethyl
FCC=flash column chromography
Fmoc=9-fluorenylmethoxycarbonyl
GC=gas chromatography
HATU=O-(7-Azabenzotriazol-1-yl)-1,1,3,3-tetramethyluronium hexafluorophosphate
HOAc=acetic acid
HOBt=hydroxybenzotriazole
m-CPBA=m-chloroperbenzoic acid
Me=methyl
mesyl=methanesulfonyl
MTBE=methyl t-butyl ether
NMM=N-methylmorpholine
NMO=N-methylmorpholine oxide
NMP=N-methylpyrrolidone
PEG=polyethylene glycol
Ph or K=phenyl
PhOH=phenol
PfP=pentafluorophenol
PPTS=pyridinium p-toluenesulfonate
PyBroP=bromo-tris-pyrrolidino-phosphonium hexafluorophosphate
rt=room temperature sat'd=saturated
s-=secondary
t-=tertiary
TBAB=tetrabutylammonium bromide
TBAI=tetrabutylammonium iodide
TBDMS=t-butyldimethylsilyl
TEA=triethylamine
TFA=trifluoroacetic acid
TBF=tetrahydrofuran
TMOF=trimethyl orthoformate
TMS=trimethylsilyl
Ts=tosyl=p-toluenesulfonyl
Trt=triphenylmethyl Although this invention is susceptible to embodiment in many different forms, preferred embodiments of the invention are shown. It should be understood, however, that the present disclosure is to be considered as an exemplification of the principles of this invention and is not intended to limit the invention to the embodiments illustrated.

It may be found upon examination that certain members of the claimed genus are not patentable to the inventors in this application. In this event, subsequent exclusions of species from the compass of applicants' claims are to be considered artifacts of patent prosecution and not reflective of the inventors' concept or description of their invention; the invention encompasses all of the members of the genus (I) that are not already in the possession of the public.

In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here.

Preparation of Intermediates 1-5 and 2-5:

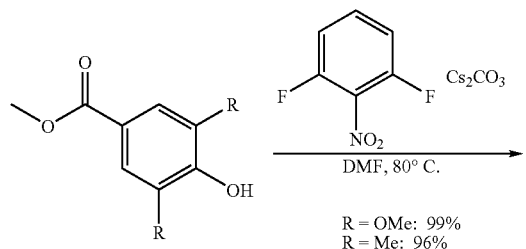

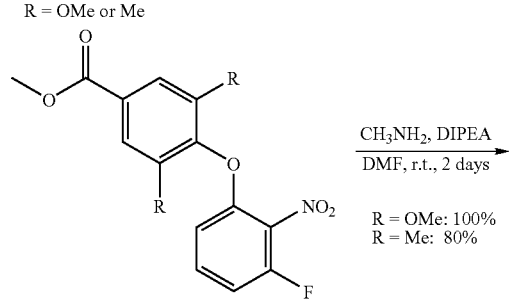

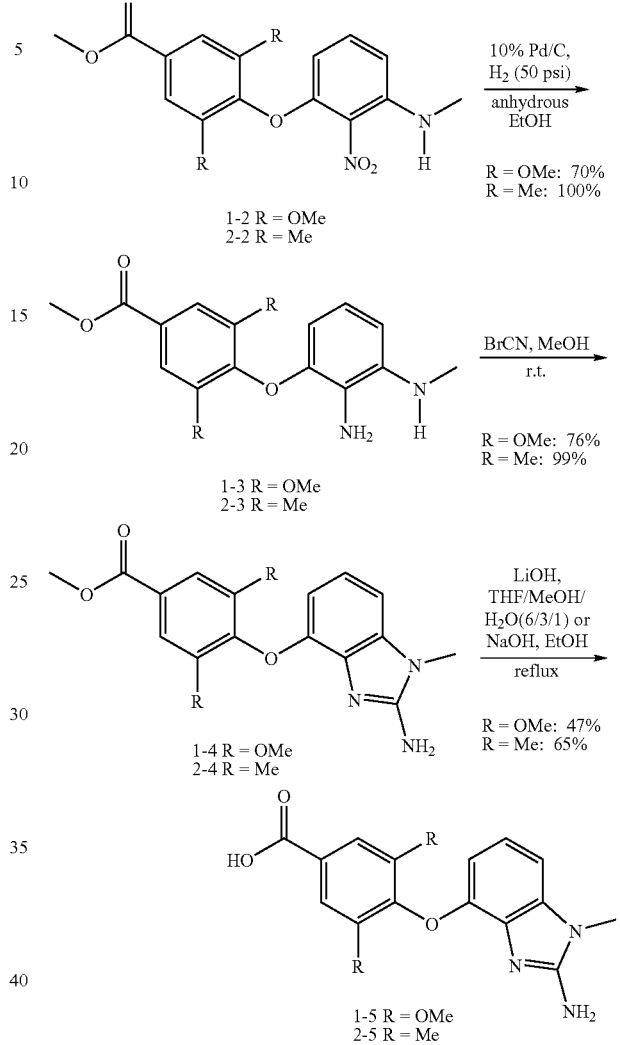

Preparation of Intermediate 1-5:

Step 1:

To a solution of methylsyringate (1.0 g; 4.72 mmol) in DMF (50 mL) were added $Cs_2CO_3$ (1.85 g; 5.66 mmol) and 2,6-difluoronitrobezene (0.5 mL; 4.72 mmol). The reaction mixture was heated to 80° C. for 16 h. The mixture was cooled and poured into water, then extracted with EtOAc (3×). The organic layers were combined and washed with water (1×) then brine (1×). The organic phase was dried (MgSO4), filtered and concentrated in vacuo giving 1.64 g (99%) of 1-1 which was used in the next reaction without further purification.

Step 2:

To a solution of 1-1 (1.46 g, 4.16 mmol) in DMF (25 mL) were added methylamine (2M in MeOH, 9.4 mL, 18.9 mmol) and diisopropylethylamine (1.64 mL; 9.44 mmol). The mixture was stirred at room temperature for 48 h. The mixture was then poured into water and extracted with EtOAc (3×). The combined organic layer was washed with brine (1×) and dried over MgSO4, filtered and concentrated in vacuo. The residue obtained was chromatographed on silica gel with n-hexane-EtOAc (1:1) to give 1.69 g of 1-2 (100%) as a yellowish solid.

Step 3:

A solution of 1-2 (1.69 g, 4.66 mmol) in anhydrous ethanol (50 mL) containing 10% of palladium on activated carbon (~50 mg) was shaken under a hydrogen atmosphere (50 psi) in a Parr apparatus for 16 h. The mixture was filtered through the celite and washed with ethanol. The filtrate was concentrated in vacuo to yield 1.08 g (70%) of 1-3 which was used in the next step without further purification.

Data for 1-3: MS: m/z (assignment, relative intensity) 333.0 (M+H$^+$, 80).

Step 4:

To a solution of 1-3 (1.08 g, 3.25 mmol) in anhydrous methanol under argon, was added 5.0 M cyanogen bromide in acetonitrile (2.60 mL, 13.0 mmol). The mixture was stirred for 16 h at room temperature and then concentrated in vacuo. The residue was chromatographed on silica gel with CH$_2$Cl$_2$—CH$_3$OH (95:5) giving 880 mg (76%) of 1-4.

Data for 1-4: MS: m/z (assignment, relative intensity) 358.3 (M+H$^+$, 65).

Step 5:

A mixture of 1-4 (880 mg, 2.46 mmol) and lithium hydroxide hydrate (540 mg, 13.00 mmol) in THF/MeOH/H2O (6:3:1) (40 mL) was refluxed for 16 h. The mixture was concentrated in vacuo to dryness. The residue was re-dissolved in distilled water and the solution obtained was adjusted to pH around 5 with 1N HCl (aq). Precipitated solid was collected by filtration and dried in vacuo to give 400 mg (47%) of 1-5. Data for 1-5: MS: m/z (assignment, relative intensity) 344.2 (M+H$^+$, 60).

Preparation of Intermediate 2-5:

Step 1:

Following the general procedure described for step 1 in example 1, 4-hydroxy-3,5-dimethyl-benzoic acid methyl ester (1.0 g, 5.55 mmol) was reacted with 2,6-difluoronitrobenzene giving 1.70 g (96%) of crude 2-1 which was used in the next step without purification.

Step 2:

Following the general procedure described for step 2 in example 1, the crude compound 2-1 was treated with methylamine to give 1.40 g (80%) of 2-2 after FCC purification (silica gel, n-Hexane/EtOAc 3:1).

Step 3:

Following the general procedure described for step 3 in example 1, the nitro compound 2-2 was reduced by hydrogenation yielding 1.29 g (100%) of corresponding amine 2-3 which was used directly in the next step without further purification.

Step 4:

Following the procedure described for step 4 in example 1, compound 2-3 was reacted with cyanogen bromide to yield, after purification by FCC (silica gel, eluted with 5% methanol/DCM), 1.38 g (99%) of aminobenzimidazole 2-4.

Data for 2-4: MS: m/z (assignment, relative intensity) 326.1 (M+H$^+$, 100).

Step 5:

The compound 24 obtained above (1.38 g, 4.25 mmol) was combined with 1N NaOH (aq) (10.6 mL, 10.6 mmol) in 20 mL EtOH. After 6 h at 60° C. the mixture was cooled and 10.6 mL 1 N HCl (aq) was added, adjusted final pH around 5. The resulting white precipitate was collected on a frit, washed with water, then with Et$_2$O and dried providing 870 mg (65%) of acid 2-5. Data for 2-5: MS: m/z (assignment, relative intensity) 312.3 (M+H$^+$, 100).

Example 3

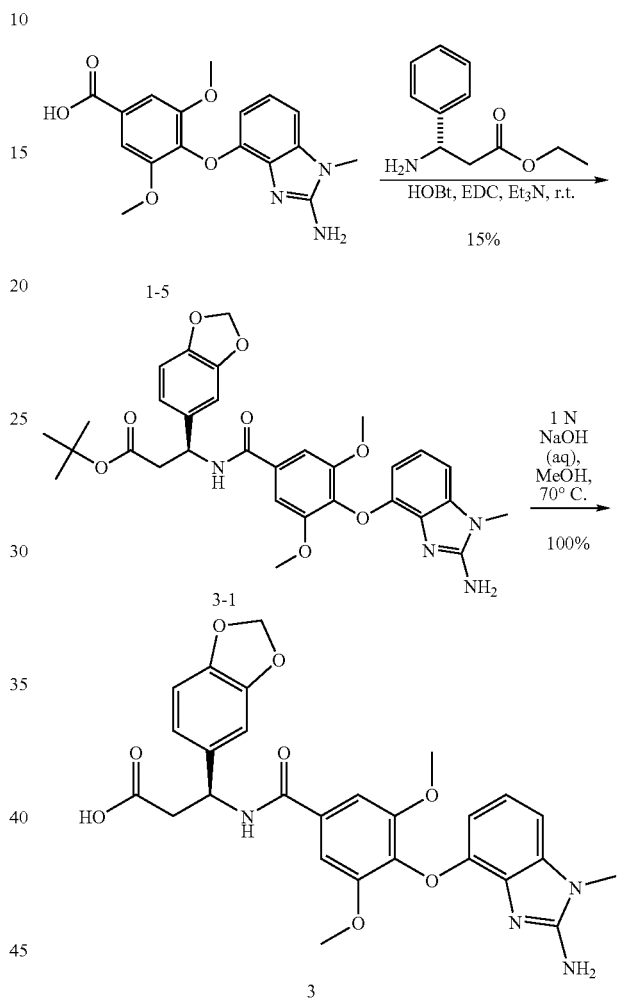

Example 3

Step 1:

To a solution of 1-5 (20 mg; 0.0583 mmol) in DMF (1 mL) were added triethylamine (10 μL; 0.064 mmol), 1-hydroxybenzotriazole (9 mg; 0.064 mmol), 1-[3-(dimethylamino)propyl]-3-ethylcarbodiimide hydrochloride (12 mg; 0.064 mmol) and (S)-3-Amino-3-benzo[1,3]dioxol-5-yl-propionic acid ethyl ester hydrochloride (16 mg; 0.0583 mmol) [For preparation see: Zablocki, J. A.; et al. *J. Med. Chem.* 1995, 38, 2378.] The reaction mixture was stirred at room temperature overnight. Then the mixture was partitioned between EtOAc and water. The aqueous phase was extracted with EtOAc (3×). The organic phases were combined and concentrated in vacuo. The residue was purified by FCC (silica gel; elution with 1:1 EtOAc:Hexane) giving 5 mg (15%) of 3-1.

Data for 3-1: MS: nWz (assignment, relative intensity) 563.1 (M+H+, 100).

Step 2:

To a solution of ethyl ester 3-1 (5 mg; 0.0089 mmol) in MeOH (2 mL) was added 1 N NaOH (aq) (50 μL; 0.050 mmol). The resultant mixture was heated to 70° C. for 16 h. The mixture was then cooled and concentrated in vacuo and the crude material was acidified to pH 2 with 1 N HCl (aq). The mixture was applied to a column filled with Dowex 50 W (H+) ion exchange resin and then eluted with water until the eluent became neutral (pH 6). The column was then eluted with 5% pyridine/H₂O. Fraction containing the desired product were pooled and concentrated in vacuo and the zwitterion thus obtained was treated with 50% TFA/DCM and concentrated in vacuo giving 6 mg of 3 (100%) as the TFA salt Data for 3: MS: m/z (assignment, relative intensity) 535.2 (M+H+, 100).

Example 4

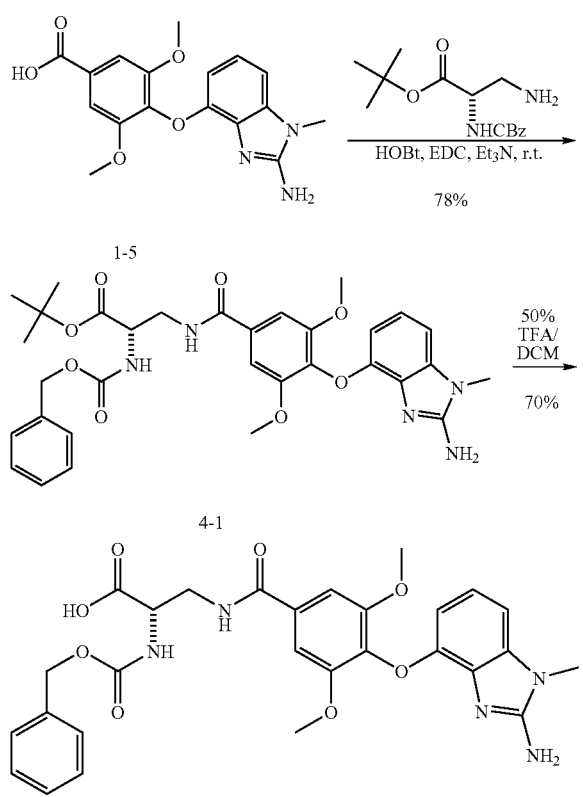

Example 4

Step 1:

To a solution of 1-5 (20 mg; 0.0583 mmol) in DMF (0.8 mL) were added triethylamine (9.47 μL; 0.07 mmol), 1-hydroxybenzotriazole (9.45 mg; 0.07 mmol), 1-[3-(dimethylamino)propyl]-3-ethylcarbodiimide hydrochloride (13.4 mg; 0.07 mmol) and (S)-3-amino-2-benzyloxycarbonylamino-propionic acid tert-butyl ester (7.14 mg; 0.0583 mmol) [For preparation see: Stilz, Hans Ulrich; et al. *J. Med. Chem.* 2001, 44, 1158-1176.] The reaction mixture was stirred at room temperature overnight. Then the mixture was partitioned between EtOAc and water. The aqueous phase was extracted with EtOAc (3×). The organic phases were combined and concentrated in vacuo. The residue was purified by FCC (silica gel; elution with 1:1 EtOAc:Hexane) giving 28 mg (78%) of 4-1.

Data for 4-1: MS: m/z (assignment, relative intensity) 620.2 (M+H+, 100), 564.2 (M-t-Bu, 67).

Step 2:

To a solution of 4-1 (28 mg; 0.0533 mmol) in DCM (3 mL) was added trifluoroacetic acid (3 mL). The reaction mixture was stirred at room temperature for 4 hours. The mixture was then concentrated in vacuo and the residue was triturated with ethyl ether (3×) giving 18 mg (70%) of 4.

Data for 4: MS: m/z (assignment, relative intensity) 564.2 (M+H+, 100).

Example 5

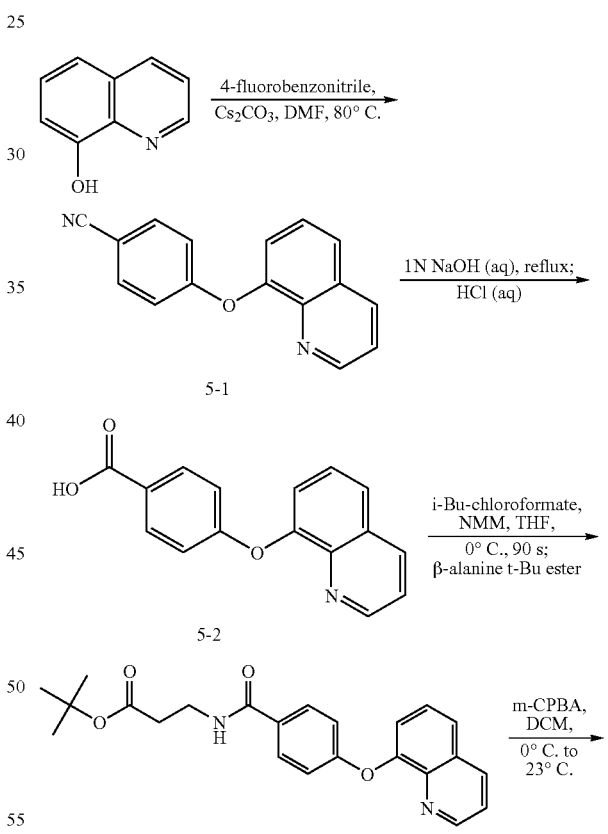

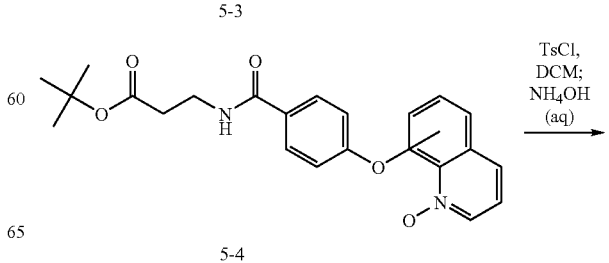

-continued

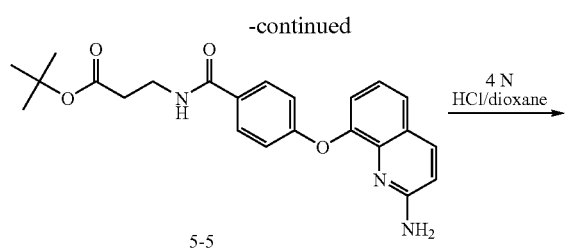

5-5

Example 5

Step 1:

To a solution of 8-hydroxyquinoline (1 g; 6.89 mmol) in DMF (7 mL) were added Cs$_2$CO$_3$ (2.24 g; 6.89 mmol) and 4-fluorobenzonitrile (834 mg; 6.89 mmol). The reaction mixture was heated to 80° C. for 16 h. The mixture was cooled and diluted with EtOAc (300 mL). This was washed with water (2×100 mL) and brine (1×100 mL). The organic phase was dried (Na$_2$SO$_4$), filtered and concentrated in vacuo giving 1.32 g (78%) of 5-1 which was used in the next reaction without further purification.

Step 2:

Benzonitrile 5-1 (1.32 g; 5.36 mmol) was treated with 13 mL of 1 N NaOH (aq) and heated to reflux for 22 h. The mixture was then cooled to room temperature and 13 mL of 1 N HCl (aq) was added carefully forming a tan precipitate which was collected by filtration and washed with cold water (2×) to afford 1.39 g of 5-2 (98%).

Data for 5-2: MS: m/z (assignment, relative intensity) 266.2 (M+H$^+$, 100).

Step 3:

To a solution of 5-2 (197 mg; 0.743 mmol) in THF (7 mL) at 0° C. were added i-butylchloroformate (96 μL; 0.743 mmol) and NMM (90 μL; 0.817 mmol) and the resultant mixture was stirred at 0° C. for 90 s. To this were added β-alanine t-butyl ester HCl (135 mg; 0.743 mmol) and TEA (114 μL; 0.817 mmol). The mixture was allowed to warm to room temperature and stirred for 0.5 h after which it was filtered through a pad of Celite and the filtrate diluted with EtOAc (100 μL). This was washed with sat. Na$_2$CO$_3$ (aq) (1×50 mL) and brine (1×50 mL), dried (Na$_2$SO$_4$), filtered and concentrated in vacuo. The residue was purified by FCC (silica gel; elution with 2:1 EtOAc:hexanes) giving 234 mg (80%) of 5-3.

Data for 5-3: MS: m/z (assignment, relative intensity) 393.0 (M+H$^+$, 100), 337.1 (M-tBu, 21).

Step 4:

To a solution of quinoline 5-3 (48 mg; 0.122 mmol) in DCM (2 mL) at 0° C. was added m-CPBA (70%; 30 mg; 0.122 mmol). The reaction mixture was allowed to warm to room temperature and stirred for 3 d. The mixture was then filtered through basic alumina (elution with DCM then 5% MeOH/DCM) to remove any unreacted m-CPBA and the filtrate was concentrated in vacuo. The crude residue was then purified by FCC (silica gel; elution with 5% MeOH/DCM) to afford 29 mg (58%) of N-oxide 5-4.

Step 5:

To a solution of the N-oxide 5-4 (29 mg; 0.0710 mmol) in DCM (0.5 mL) was added TsCl (16 mg; 0.0852 mmol) and this was immediately followed by the addition of conc. NH$_4$OH (aq) (0.15 mL). The biphasic mixture was stirred vigorously at room temperature for 3 h and was then diluted with EtOAc and washed with sat. NaHCO$_3$ (aq) (1×). The organic phase was dried (Na$_2$SO$_4$), filtered and concentrated in vacuo and the residue was purified by FCC (silica gel; elution with 5% MeOH/DCM) giving 9 mg (31%) of aminoquinoline 5-5.

Data for 5-5: MS: m/z (assignment, relative intensity) 408.0 (M+H$^+$, 100), 352.2 (M-tBu, 13).

Step 6:

5-5 was treated with 4 N HCl in dioxane (2 mL) and allowed to stand for 16 h. This was then concentrated in vacuo giving 9 mg of 5 as an HCl salt.

Data for 5: MS: m/z (assignment, relative intensity) 352.2 (M+H$^+$, 100).

Example 6

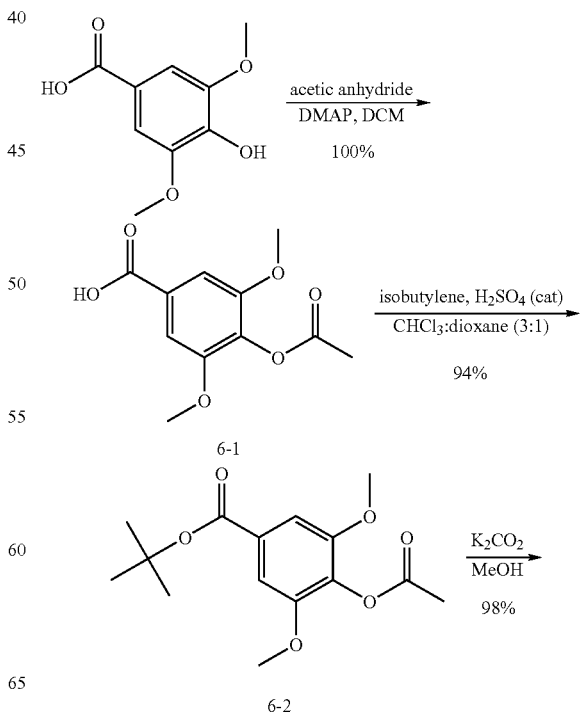

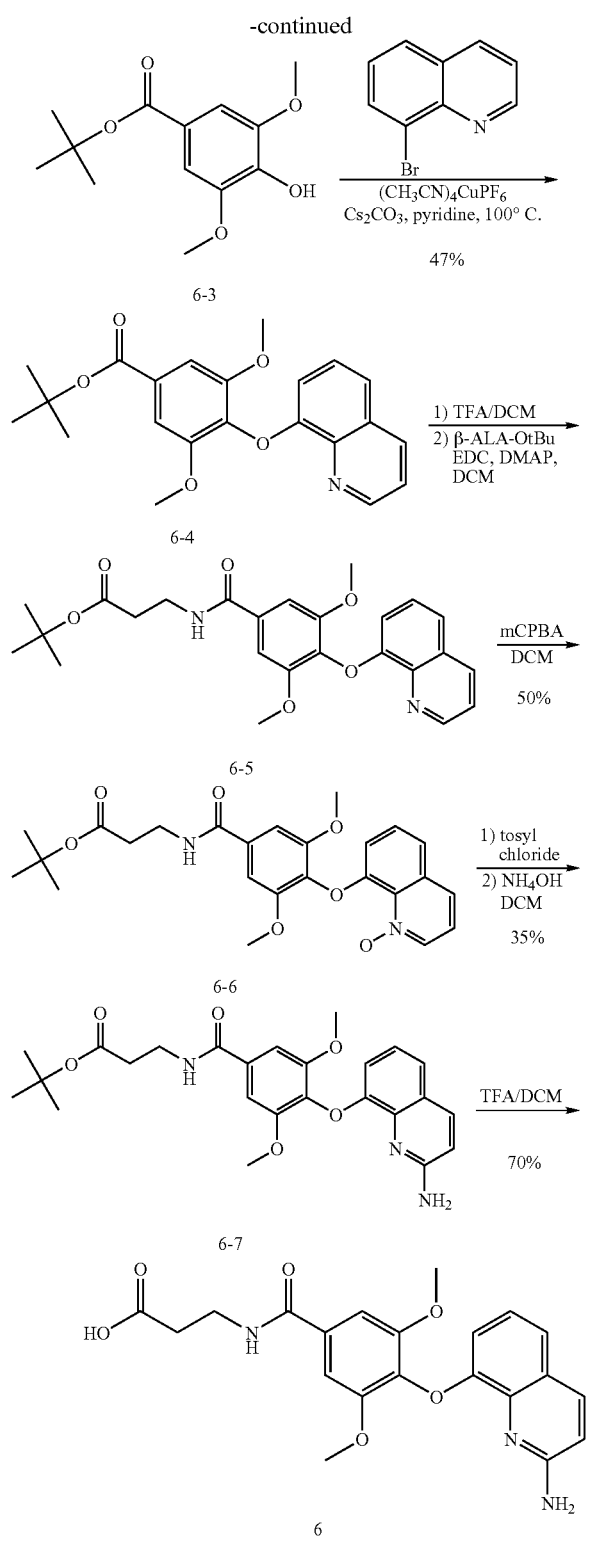

Example 6

Step 1:

To syringic acid (9.9 g, 50 mmol) in 100 mL DCM was added DMAP (6.7 g, 55 mmol). To this solution was added slowly acetic anhydride (5.6 g, 55 mmol). The solution was stirred for 3 hours and then concentrated in vacuo. The residue was taken up in DCM and washed with 1N HCl. The organic layer was dried over $MgSO_4$ and concentrated to yield 6-1 as an orange solid (12 g, 50 mmol, 100%).

Step 2

To 6-1 (1.3 g, 5.4 mmol) in 30 mL of $CHCl_3$:dioxane (3:1) in a pressure vessel at −78° C. was added approx 10 mL isobutylene and a few drops of concentrated sulfuric acid. The vessel was sealed, warmed to 25° C. for 2 hours, then heated to 80° C. for 18 hours. The solution was then concentrated in vacuo. The residue was taken up in DCM and washed with water. The organic layer was dried over $MgSO_4$ to yield 6-2 as a white solid (1.5 g, 5.1 mmol, 94%).

Step 3

To 6-2 (1.5 g, 5.1 mmol) in 30 mL MeOH was added $K_2CO_3$ (1.4 g, 10 mmol) and stirred for 1 hour. The mixture was filtered and concentrated in vacuo. The residue was taken up in DCM and washed with 1N HCl. The organic layer was dried over $MgSO_4$ to yield 6-3 as an oil (1.3 g, 5 mmol, 98%).

Step 4

6-3 (0.25 g, 1 mmol), 8-bromoquinoline (0.21 g, 1 mmol), $Cs_2CO_3$ (11.0 g, 3 mmol), and tetrakisacetonitrile copper(I) hexafluoroacetate (0.37 g, 1 mmol) were suspended in 2.5 ml anhydrous pyridine under an Argon atmosphere and heated at 100° C. After 8 hours and additional 0.37 g of and tetrakisacetonitrile copper(I)hexafluoroacetate was added. After 18 hours the mixture was diluted with water and extracted with DCM. The organic layer was concentrated in vacuo and the residue chromatagraphed on a silica gel column, eluting with 30% EtOAc:hexanes to yield 6-4 as a foam (0.18 g, 0.47 mmol, 47%).

Data for 6-4: MS: ni/z (assignment, relative intensity) 326.3 ($M+H^+$-tbu, 90)

Step 5:

6-4 (0.3 g, 0.8 mmol) was treated with 10 ml 50% TFA/DCM for 45 minutes. The solution was concentrated in vacuo. The residue was taken up in DCM and basified with excess DIEA. To this solution was added N-methylmorpholine (290 µl, 2.6 mmol) and isobuytylchloroformate (115 µl, 0.9 mmol). After 10 minutes β-alanine t-butyl ester (0.18 g, 0.96 mmol) was added. The solution was stirred for 18 hours. The solution was then concentrated in vacuo. The residue was taken up in DCM and washed with 0.5N HCl and 0.5N NaOH. The organic layer was dried over $MgSO_4$ and concentrated. The resulting oil 6-5 was used without purification.

Data for 6-5: MS: m/z (assignment, relative intensity) 453.3 ($M+H^+$, 90)

Step 6

To 6-5 in 10 ml DCM was added 3-perchlorobenzoic acid (0.69 g, 4 mmol). The mixture was stirred for 18 hours then diluted with DCM and washed with 1N NaOH. The organic layer was dried over $MgSO_4$ and concentrated to yield 6-6 as a glass (0.1 g, 0.2 mmol, 50% over 2 steps).

Step 7

To 6-6 (0.1 g, 0.2 mmol) in 1.8 ml $CHCl_3$ was added tosyl chloride (0.5 g, 0.26 mmol) immediately followed by ammonium hydroxide (110 µl, 2 ml/mmol). The solution was stirred for 90 minutes then diluted with saturated $NaHCO_3$ and extracted with $CHCl_3$. After concentration, the residue was chromatagraphed on a silica gel column eluting with 5% MeOH/DCM to 7% MeOH/DCM to yield 6-7 as a foam (0.033 g, 0.07 mmol, 35%).

Data for 6-7: MS: m/z (assignment, relative intensity) 468.2 (M+H⁺, 95)

Step 8

6-7 was treated with 10 ml TFA/DCM for 6 hours. The solution was then concentrated and purified by preparative HPLC to yield 6 as a tan solid (0.02 g, 0.05 mmol, 70%).

Data for 6: MS: nVz (assignment, relative intensity) 412:6 (M+H⁺, 90)

Example 7

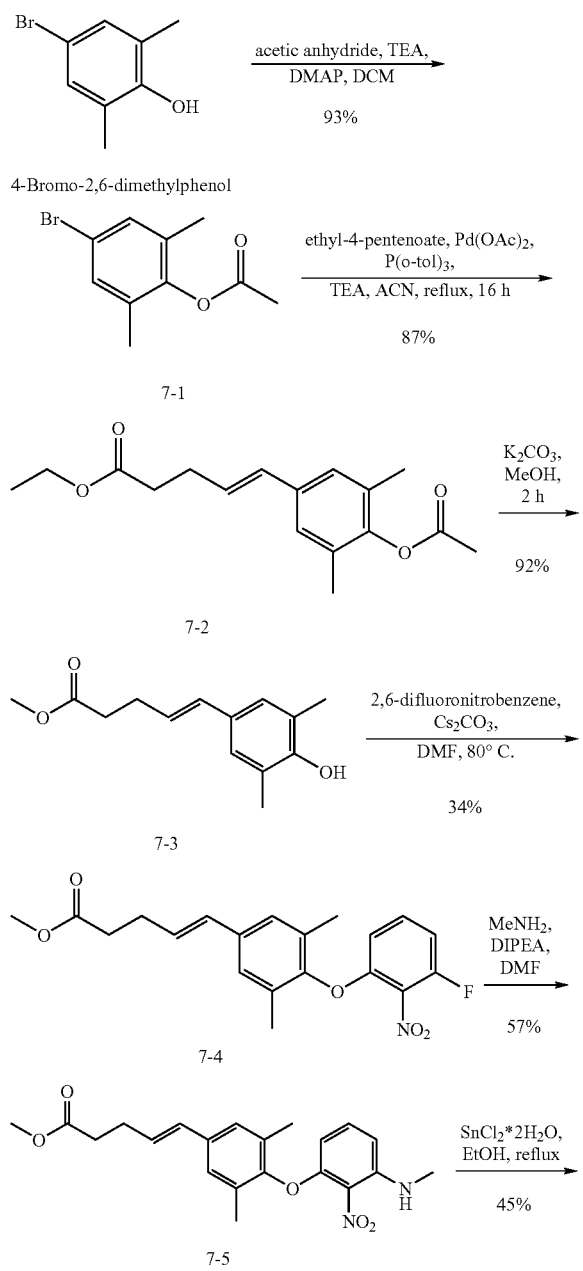

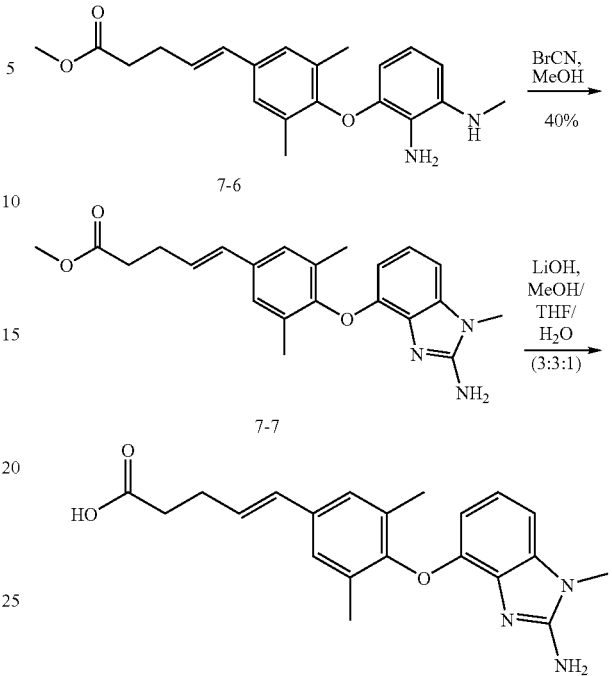

Example 7

Step 1:

To a solution of 4-bromo-2,6-dimethylphenol (1.00 g; 4.97 mmol) in DCM (25 mL) were added triethylamine (1.04 mL; 7.46 mmol) and acetic anhydride (0.56 mL; 5.96 mmol). To this was added a small scoop of DMAP and the reaction mixture was stirred at 23° C. for 1 h. The volatiles were removed in vacuo and the residue was taken up in EtOAc (100 mL). The organic solution was washed with 1 M HCl (aq) (1×40 mL), sat. NaHCO₃ (aq) (1×40 mL) and brine (1×40 mL). The organic phase was dried (Na₂SO₄), filtered and concentrated in vacuo giving 1.13 g of 7-1 (93%) which was used in the next step without further purification.

Step 2:

To a solution of 7-1 (500 mg; 2.06 mmol) and ethyl-4-pentenoate (0.26 mL; 2.06 mmol) in acetonitrile (10 mL) were added TEA (0.57 mL; 4.12 mmol), P(o-tol)₃ (82 mg; 0.268 mmol) and Pd(OAc)₂ (46 mg; 0.206 mmol). The reaction vessel was flushed with Argon and the reaction mixture was then heated to reflux for 16 h. The mixture was cooled, concentrated in vacuo and the residue was purified by FCC (silica gel; elution with 5:1 hexanes:EtOAc) affording 520 mg of 7-2 (87%).

Step 3:

To a solution of 7-2 (520 mg; 1.80 mmol) in MeOH (9 mL) was added potassium carbonate (371 mg; 2.69 mmol) and the mixture was stirred at 23° C. for 2 h. The solvent was then removed in vacuo and the crude residue was partitioned between EtOAc and sat. NH₄Cl (aq). The organic phase was washed with brine (1×), dried (Na₂SO₄), filtered and concentrated in vacuo to afford 390 mg of phenol 7-3 (92%) which was used in the following reaction without further purification.

Step 4:

To a solution of phenol 7-3 (0.39 g; 1.66 mmol) in DMF (16 mL) were added 2,6-difluoronitrobenzene (0.18 mL; 1.66 mmol) and $Cs_2CO3$ (541 mg; 1.66 mmol). The reaction mixture was heated to 80° C. for 16 h. The mixture was cooled, diluted with EtOAc (100 mL) and washed with water (1×50 mL) and brine (1×50 mL). The organic phase was dried over $Na_2SO_4$, filtered and concentrated in vacuo and the crude residue was purified by FCC (silica gel; elution with 5:1 hexanes:EtOAc) giving 210 mg of 7-4 (34%).

Step 5:

To a solution of 7-4 (210 mg; 0.562 mmol) in DMF (5 mL) were added $MeNH_2$ (2.0 M in THF; 0.56 mL; 1.12 mmol) and DIPEA (0.2 mL; 1.12 mmol). The resultant mixture was stirred at 23° C. for 16 h. More $MeNH_2$ (2.0 M in THF; 0.56 mL; 1.12 mmol) was added and stirring was continued for another 16 h. After diluting with EtOAc (50 mL) the mixture was washed with water (1×20 mL) and brine (1×20 mL). The organic phase was dried ($Na_2SO_4$), filtered and concentrated in vacuo. The residue was purified by FCC (silica gel; elution with 2:1 hexanes:EtOAc) giving 123 mg of 7-5 (57%).

Data for 7-5: MS: m/z (assignment, relative intensity) 385.0 $(M+H^+, 100)$.

Step 6:

To a solution of alkene 7-5 (123 mg; 0.320 mmol) in EtOH (3 mL) was added $SnCl_2.2H_2O$ (361 mg; 1.60 mmol). The reaction mixture was heated to reflux for 16 h. The mixture was then cooled and concentrated in vacuo. Water was added (10 mL) and the pH was adjusted to 9 with sat. $NaHCO_3$ (aq). This was extracted with EtOAc (3×20 mL) and the combined organics were washed with water (1×20 mL) and brine (1×20 mL). The organic layer was then dried ($Na_2SO_4$), filtered and concentrated in vacuo giving 53 mg of ethyl ester 7-6 (45%).

Data for 7-6: MS: m/z (assignment, relative intensity) 369.1 $(M+H^+, 100)$.

Step 7

To a solution of diamine 7-6 (53 mg; 0.144 mmol) in MeOH (1 mL) was added cyanogen bromide (0.5 M in acetonitrile; 0.12 mL; 0.575 mmol). The reaction mixture was stirred at 23° C. for 3 days. The reaction was quenched with sat. $NaHCO_3$ (aq) and concentrated in vacuo. The crude residue was partitioned between EtOAc and water. The organic phase was washed with brine (1×), dried ($Na_2SO_4$), filtered and concentrated in vacuo. Purification by FCC (silica gel; elution with 10% MeOH/DCM) afforded 23 mg (40%) of aminobenzimidazole 7-7.

Data for 7-7: MS: m/z (assignment, relative intensity) 394.3 $(M+H^+, 100)$.

Step 8:

To a solution of the ethyl ester 7-7 (23 mg; 0.0585 mmol) in MeOH (3 mL), THF (3 mL) and water (1 mL) was added $LiOH.H_2O$ (20 mg; XS). The reaction mixture was stirred at 23° C. for 16 h. The volatiles were removed in vacuo and the mixture was acidified to pH 1 with 2 N HCl (aq). The aqueous solution was applied to a column filled with Dowex 50 W ($H^+$) resin. The column was washed with water until the eluant became neutral and was then eluted with 5% pyridine/$H_2O$. The desired fractions were combined and concentrated in vacuo. The crude material thus obtained was then purified by FCC (silica gel; elution with 8:2:0.2 DCM:MeOH:$H_2O$) giving 7.5 mg (36%) of acid 7.

Data for 7: MS: r2 z (assignment, relative intensity) 366.3 $(M+H^+, 100)$.

Example 8

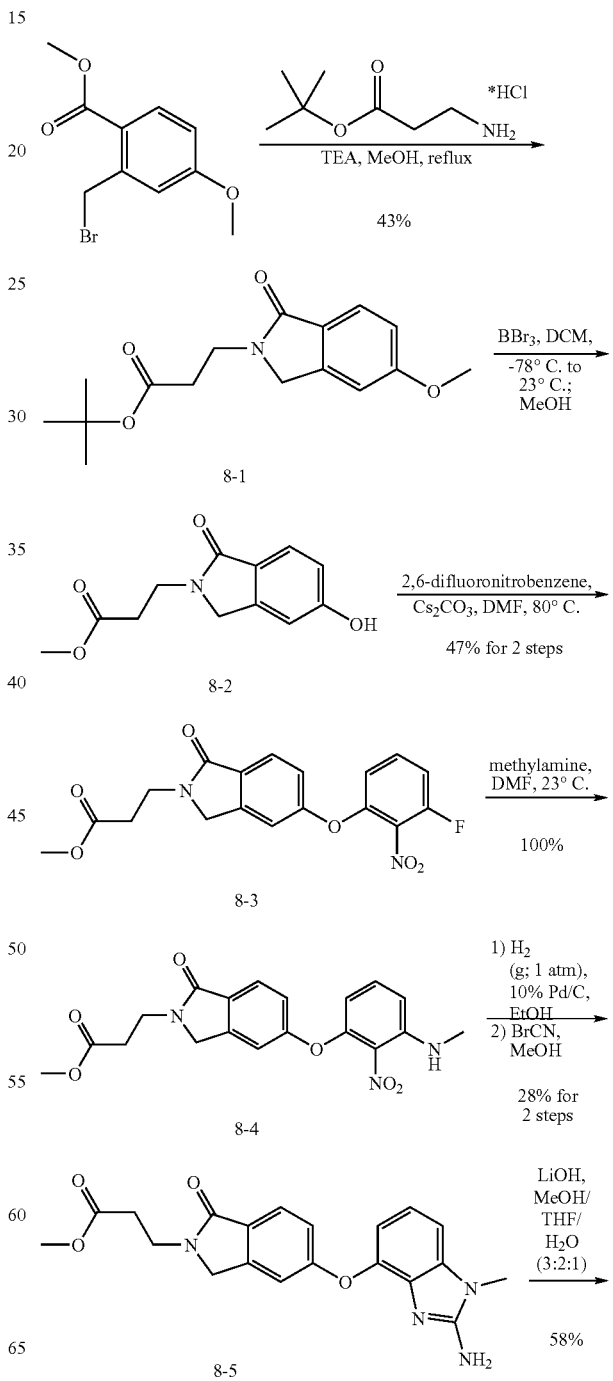

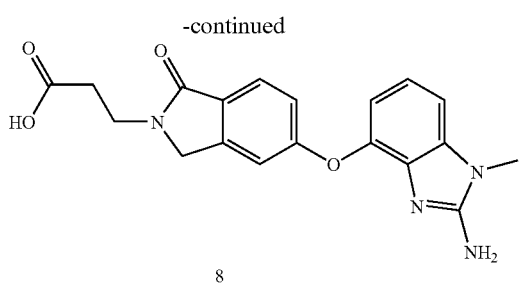

8

Example 8

Step 1:

To a solution of 2-Bromomethyl-4-methoxy-benzoic acid methyl ester (310 mg; 1.20 mmol) [For preparation see: Wyrick, S. D.; et al. *J. Med. Chem.* 1987, 30, 1798-1806 and references therein] in MeOH (2 mL) were added triethylamine (418 μL; 3.00 mmol) and β-alanine t-Bu ester hydrochloride (240 mg; 1.32 mmol). The reaction mixture was heated to reflux for 3 h. The mixture was then cooled, concentrated in vacuo and the crude residue was taken up in EtOAc. This was washed with 1 N HCl (aq) (1×), dried ($Na_2SO_4$), filtered and concentrated in vacuo. The residue was purified by FCC (silica gel; elution with 1:1 EtOAc:hexanes) giving 152 mg (43%) of 8-1.

Data for 8-1: MS: m/z (assignment, relative intensity) 291.9 ($M+H^+$, 100), 236.1 (M-tBu, 25%).

Step 2:

To a solution of 8-1 (152 mg; 0.522 mmol) in DCM (2 mL) at −78° C. was added $BBr_3$ (1M in DCM; 1.8 mL; 1.8 mmol). The mixture was allowed to warm to room temperature and stirred for 16 h. The mixture was then cooled to −78° C. and quenched with MeOH (1 mL). The mixture was allowed to warm to room temperature and the volatiles were removed in vacuo. The crude residue was azeotroped with MeOH (3×) and used in the next reaction without further purification.

Data for 8-2: MS: Hz (assignment, relative intensity) 236.1 ($M+H^+$, 100).

Step 3:

To a solution of 8-2 (123 mg; 0.522 mmol) in DMF (5 mL) were added 2,6-difluoronitrobenzene (55 μL; 0.522 mmol) and $Cs_2CO_3$ (170 mg; 0.522 mmol). The reaction mixture was heated to 80 IC for 16 h. The mixture was cooled and partitioned between EtOAc and water. The aqueous phase was extracted with EtOAc (3×). The organic phases were combined and washed with water (1×) and brine (1×). The organic phase was dried ($Na_2SO_4$), filtered and concentrated in vacuo. The residue was purified by FCC (silica gel, elution with 3:1 EtOAc:hexanes) giving 91 mg (47% for 2 steps) of 8-3.

Step 4:

To a solution of 8-3 (91 mg; 0.243 mmol) in DMF (2 mL) was added $MeNH_2$ (2.0 M in MeOH; 0.49 mL; 0.972 mmol). The reaction mixture was stirred at room temperature for 16 h. The mixture was diluted with EtOAc (100 mL) and washed with water (1×25 mL) and brine (1×25 mL). The organic phase was dried ($Na_2SO_4$), filtered and concentrated in vacuo. The desired aniline 8-4 was used crude in the next reaction.

Step 5:

8-4 (95 mg; 0.243 mmol) was reduced by hydrogenation in EtOH in the presence of a catalytic amount of 10% Pd/C under 1 atm of $H_2$ (g) (balloon) for 6 h. The reaction mixture was filtered through a pad of Celite and concentrated in vacuo. The crude residue was taken up in MeOH (2 μL) and to the resultant solution was added cyanogen bromide (5 M in acetonitrile; 0.19 mL; 0.972 mmol). The mixture was stirred for 16 h at room temperature and was then quenched with sat. $NaHCO_3$ (aq) and concentrated in vacuo. The residue was partitioned between EtOAc and water and the aqueous phase was extracted with additional EtOAc (2×). The organic phases were combined, dried ($Na_2SO_4$), filtered and concentrated in vacuo.

The residue was purified by FCC (silica gel, elution with 10% MeOH/DCM) affording 26 mg of the desired aminobenzimidazole 8-5.

Data for 8-5: MS: m/z (assignment, relative intensity) 381.3 ($M+H^+$, 100), 761.0 ($2M+H^+$, 6).

Step 6:

To a solution of methyl ester 8-5 (26 mg; 0.0683 mmol) in MeOH (1.5 mL), THF (1 mL) and water (0.5 mL) was added $LiOH.H_2O$ (9 mg; 0.205 mmol). The reaction mixture was stirred for 0.5 h and then more $LiOHH_2O$ (8 mg) was added after which stirring was continued for 2 h. The mixture was then concentrated in vacuo and the residue treated with 1 mL of water. This was brought to pH 4-5 by addition of 1 N HCl (aq) giving an off-white precipitate which was collected by filtration. The solid thus obtained was treated with 50% TFA/DCM and concentrated in vacuo affording 19 mg of 8 as a TFA salt.

Data for 8: MS: m/z (assignment, relative intensity) 367.2 ($M+H^+$, 100), 733.1 ($2M+H^+$, 22).

Example 9

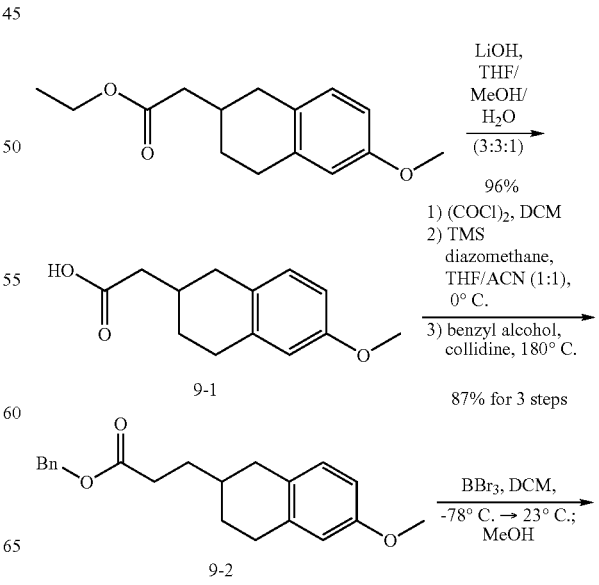

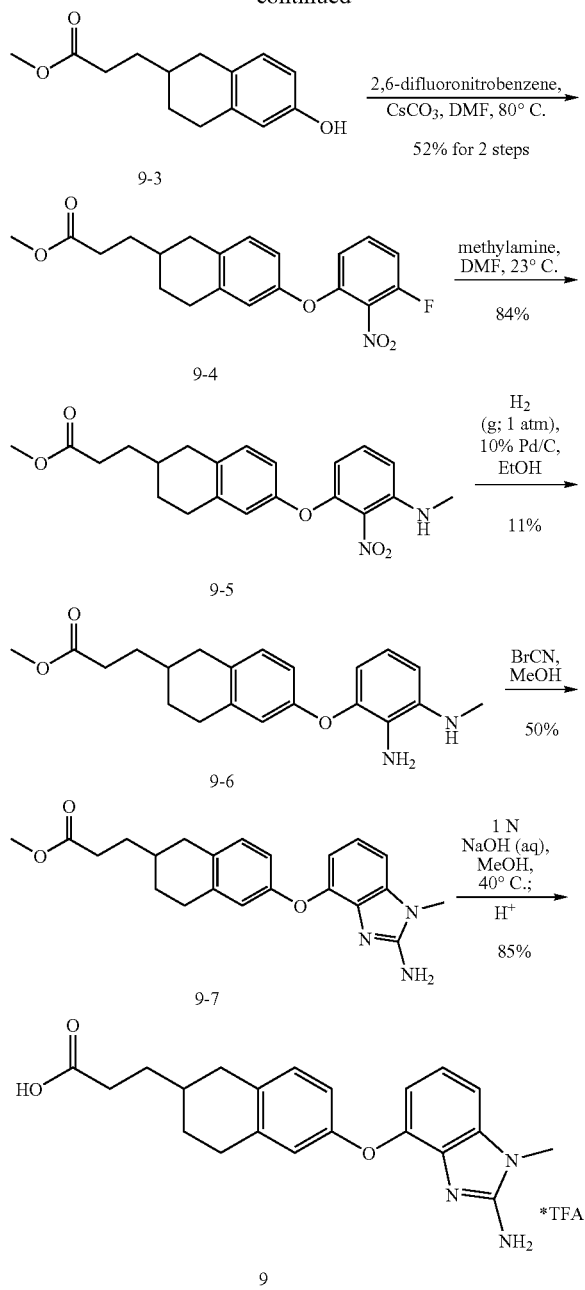

Example 9

Step 1:

To a solution of (6-Methoxy-1,2,3,4-tetrahydro-naphthalen-2-yl)-acetic acid ethyl ester (307 mg; 1.13 mmol) [For preparation see: Fisher, M. J.; et al. *J. Med Chem* 1999, 42, 4875-4889] in THF (3 mL), MeOH (3 mL) and water (1 mL) was added LiOH·H$_2$O (142 mg; 3.38 mmol). The reaction mixture was stirred at room temperature for 2 hours and was then concentrated in vacuo. The residue was made acidic by the addition of 1 N HCl (aq) and the cloudy white mixture was extracted with EtOAc (3×). The combined organic layers were dried (Na$_2$SO$_4$), filtered and then concentrated in vacuo giving 264 mg of acid 9-1 (96%) which was of suitable purity for synthetic use in the next step.

Step 2:

To a solution of acid 9-1 (83 mg; 0.340 mmol) in DCM (1 mL) were added oxalyl chloride (36 µL; 0.408 mmol) and a drop of DMF (cat.). The reaction mixture was stirred at room temperature for 0.5 h until bubbling ceased. The mixture was concentrated in vacuo and then azeotroped with toluene (2×). The crude acid chloride was dissolved in THF (0.5 mL) and ACN (0.5 mL), cooled to 0° C., and to this was added TMSdiazomethane (2.0 M in hexanes; 0.37 mL; 0.748 mmol). The reaction mixture was stirred at 0° C. for 2.5 h and was then concentrated in vacuo. Benzyl alcohol (0.5 mL) and collidine (0.5 mL) were then added to the crude diazoketone and the mixture was heated to 180° C. for 10 min. The mixture was cooled to room temperature, diluted with ethyl ether and washed with 1N HCl (aq) (1×20 mL), water (1×10 mL) and brine (1×10 mL). The ether layer was dried (Na$_2$SO$_4$), filtered and concentrated in vacuo. The crude product was purified by FCC (silica gel; elution with 6:1 hexanes:EtOAc) giving 99 mg of benzyl ester 9-2(87%).

Step 3:

Following the general procedure described for step 2 in example 8, the product from above, 9-2, was reacted with BBr$_3$ giving phenol 9-3 which was used in the next step crude without further purification.

Step 4:

Following the procedure described for step 3 in example 8, the crude product from above, 9-3, was reacted with 2,6-difluoronitrobenzene giving, after purification by FCC (silica gel; elution with 4:1 hexanes: EtOAc), 67 mg (64% for 2 steps) of 94.

Step 5:

Following the procedure described for step 4 in example 8, compound 9-4 from above was reacted with methylamine to afford 58 mg (84%) of 9-5 after purification by FCC (silica gel; elution with 4:1 hexanes:EtOAc).

Step 6:

9-5 (58 mg; 0.151 mmol) was reduced by hydrogenation in EtOH in the presence of a catalytic amount of 10% Pd/C under 1 atm of H$_2$ (g) (balloon) for 16 h. The reaction mixture was filtered through a pad of Celite and concentrated in vacuo. The residue was purified by FCC (silica gel, elution with 2:1 hexanes:EtOAc) to afford 6 mg (11%) of the desired diamine 9-6.

Data for 9-6: MS: m/z (assignment, relative intensity) 355.3 (N+H$^+$, 100).

Step 7:

The diamine 9-6 above was taken up in MeOH (1 mL) and to the resultant solution was added cyanogen bromide (5 M in ACN; 0.014 mL; 0.0677 mmol). The mixture was stirred for 1 h at room temperature and was then quenched with sat. NaHCO$_3$ (aq) and concentrated in vacuo. The residue was partitioned between EtOAc and brine and the aqueous phase was extracted with additional EtOAc (2×). The organic phases were combined, dried (Na$_2$SO$_4$), filtered and concentrated in vacuo. The residue was purified by FCC (silica gel, elution with 10% MeOH/DCM) affording 3 mg (50%) of the desired amrinobenzimidazole 9-7.

Data for 9-7: MS: m/z (assignment, relative intensity) 380.5 (M+H$^+$, 100).

Step 8:

To a solution of methyl ester 9-7 (3 mg; 0.00791 mmol) in MeOH (0.5 mL) was added 50 μL of 1 N NaOH (aq). The resultant mixture was stirred at room temperature for 16 h. Analysis by HPLC showed incomplete reaction so more 1 N NaOH (aq) was added (50 μL) and the mixture was heated to 40° C. for 1 h. The mixture was then cooled and concentrated in vacuo and the crude material was acidified to pH 2 with 1 N HCl (aq). The crude suspension was applied to a column filled with Dowex 50 W (H$^+$) ion exchange resin and then eluted with water until the eluent became neutral (pH 6). The column was then eluted with 5% pyridine/H$_2$O. Fractions containing the desired product were pooled and concentrated in vacuo and the zwitterion thus obtained was treated with 50% TFA/DCM and concentrated in vacuo giving 3.4 mg of 9 (85%) as the TFA salt.

Data for 9: MS: m/z (assignment, relative intensity) 366.5 (M+H$^+$, 100)

Example 10

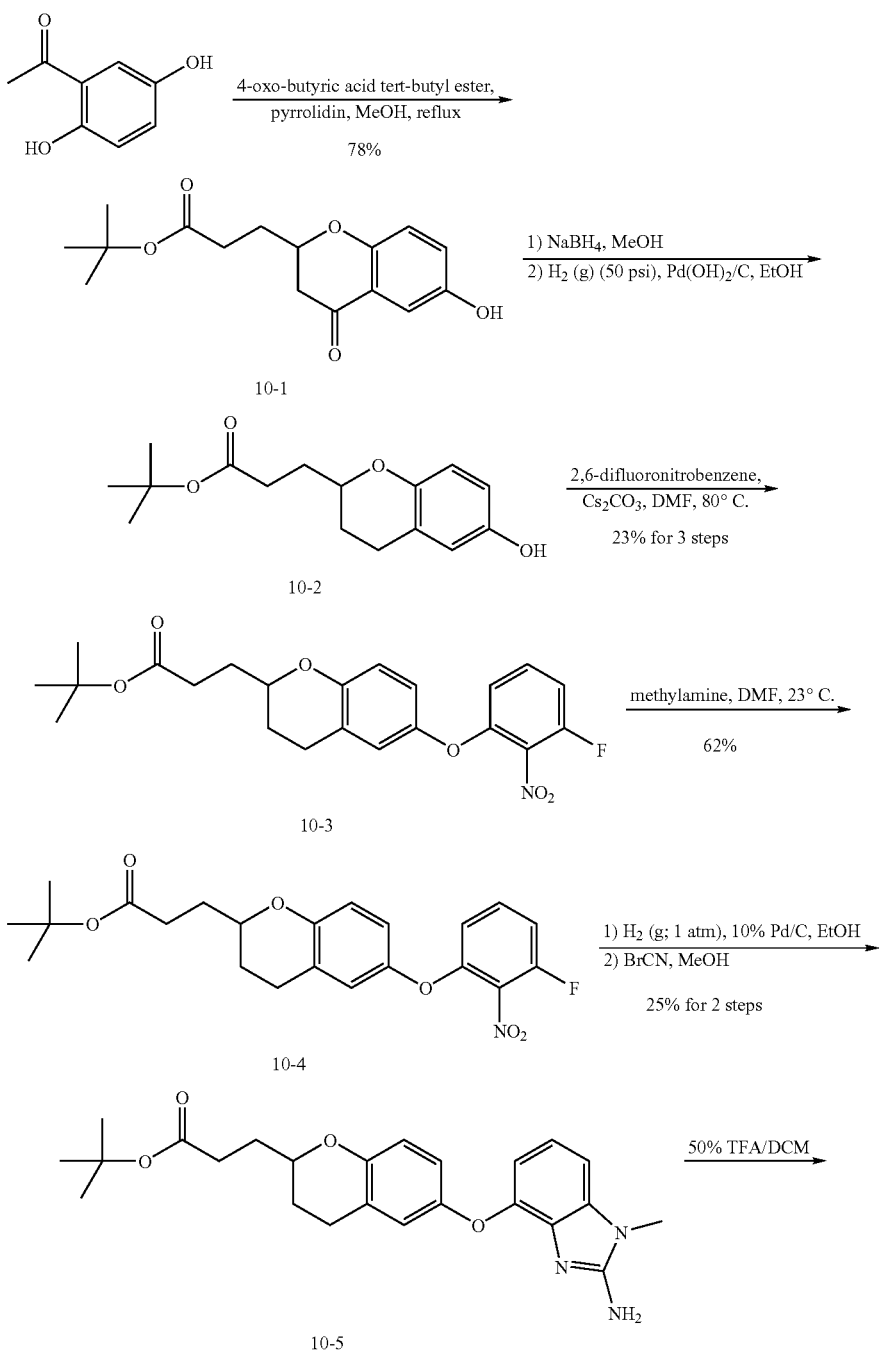

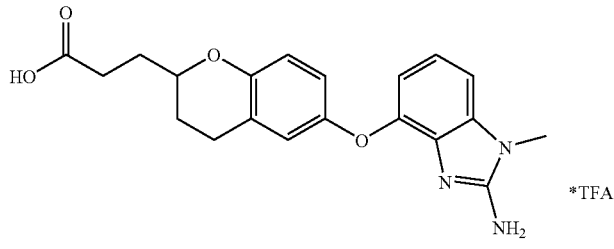

10

Example 10

Step 1:

To a solution of 4-oxo-butyric acid tert-butyl ester (53 mg; 0.335 mmol) in MeOH (3 mL) were added 2',5'-dihydroxy-acetophenone (51 mg; 0.335 mmol) and pyrrolidine (28 μL; 0.335 mmol). The reaction mixture was heated to 70° C. for 16 h. The mixture was cooled, concentrated in vacuo and the residue was purified by FCC (silica gel; elution with 3:1 hexanes:EtOAc) to afford 76 mg (78%) of 10-1.

Step 2:

To a solution of 10-1 (76 mg; 0.260 mmol) in MeOH (5 mL) was added NaBH$_4$ (12 mg; 0.312 mmol). The reaction mixture was stirred for 1 h and was then concentrated in vacuo. The residue was treated with brine and extracted with EtOAc (3×). The organic layers were combined, dried (Na$_2$SO$_4$), filtered and concentrated in vacuo. The crude alcohol was taken up in EtOH and the resulting solution placed in a Parr shaker vessel. To this was added a small scoop of Pd(OH)$_2$/C. The mixture was placed under 50 psi of H$_2$ (g) and shaken for 16 h in a Parr hydrogenator. The mixture was then filtered through a pad of Celite and concentrated in vacuo giving 72 mg (100%) of 10-2 which was used without further purification.

Data for 10-2: MS: m/z (assignment, relative intensity) 301.0 (M+Na$^+$, 100), 222.9 (M-tBu, 42).

Step 3:

Following the procedure described for step 3 in example 8, the crude product from above, 10-2, was reacted with 2,6-difluoronitrobenzene giving, after purification by FCC (silica gel; elution with 4:1 hexanes:EtOAc), 25 mg (23% for 3 steps) of 10-3.

Step 4:

Following the procedure described for step 4 in example 8, compound 10-3 from above was reacted with methylamine to afford 16 mg (62%) of 10-4 after purification by FCC (silica gel; elution with 4:1 hexanes:EtOAc).

Step 5:

Following the procedure described for step 5 in example 8, compound 10-4 from above was reduced and then reacted with cyanogen bromide to afford, after purification by FCC (silica gel; elution with 10% MeOH/DCM), 4 mg (25% for 2 steps) of aminobenzimidazole 10-5.

Data for 10-5: MS: m/z (assignment, relative intensity) 424.1 (M+H$^+$, 100), 368.3 (M-tBu, 72).

Step 6:

10-5 (4 mg; 0.0094 mmol) was treated with 50% TFA/DCM and allowed to stand for 16 h. This was then concentrated in vacuo and triturated with Et2O giving 4 mg (89%) of 10 as a TFA salt.

Data for 10: MS: m/z (assignment, relative intensity) 368.2 (M+H$^+$, 100).

Example 11

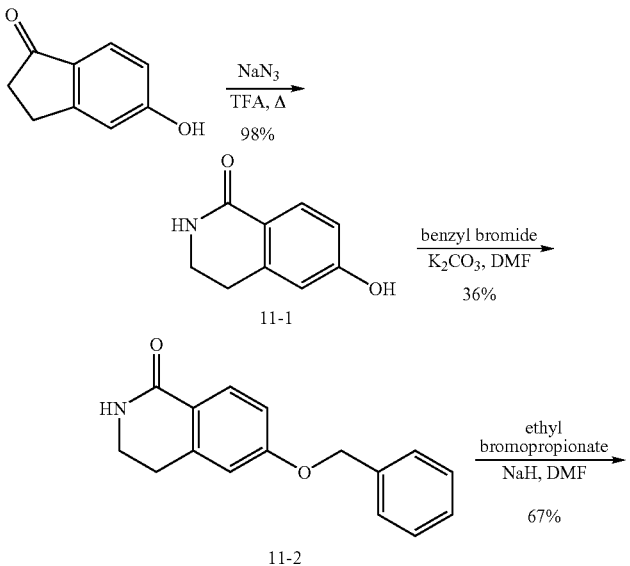

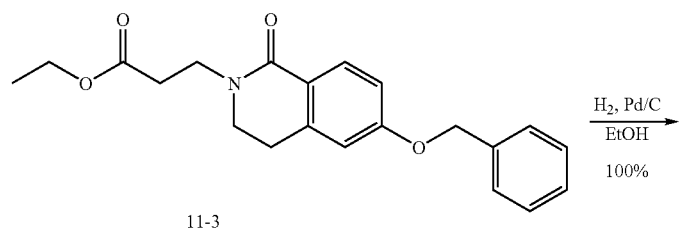
11-3
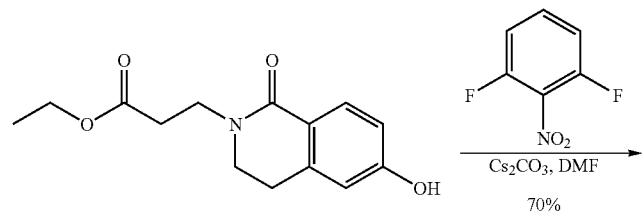
11-4
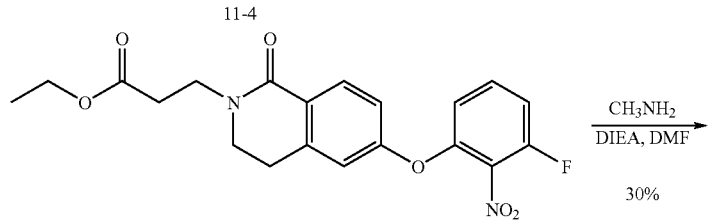
11-5
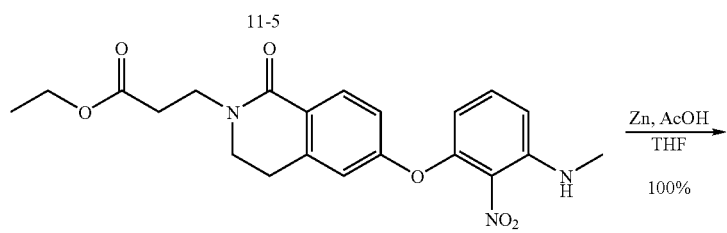
11-6
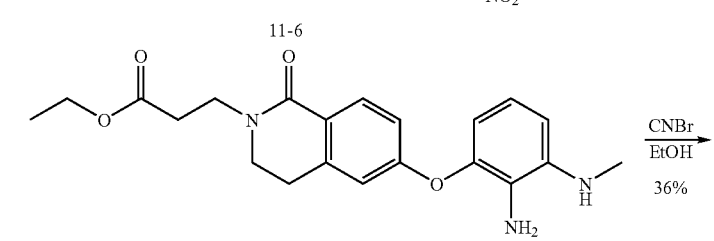
11-7
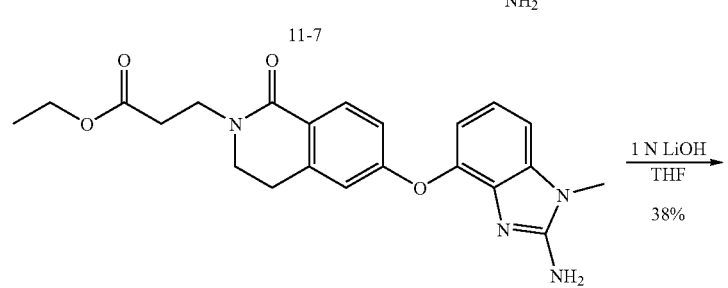
11

Example 11

Step 1:

To a solution of 5-hydroxyindanone (1.5 g, 10 mmol) in 15 ml trifluroracetic acid was added sodium azide (1.0 g, 15 mmol) portionwise. The solution was stirred at reflux for 2 h, then cooled and diluted with water. The volatiles were removed in vacuo and the resulting residue diluted with saturated $NaHCO_3$ and extracted with ethyl acetate. The organic layers were dried over $MgSO_4$ and concentrated to yield 11-1 (1.6 g, 98%) as a tan solid which was used without further purification.

Step 2:

To a solution of 11-1 (0.8 g, 5 mmol) in 10 ml DMF was added $K_2CO3$ (1.4 g, 10 mmol) and benzyl bromide (1.7 g, 10 mmol). The mixture was stirred at 25° C. for 18 h. The resulting mixture was then filtered and concentrated in vacuo. The resulting oil was purified on a silica gel column, eluting with 5% MeOH/DCM to yield 11-2 (0.46 g, 1.8 mmol, 36%) as an oil.

Step 3:

A solution of 11-2 (0.46 g, 1.8 mmol) in 15 ml anhydrous DMF was added to NaH (60% in mineral oil, 110 mg, 2.7 mmol) slowly. The resulting mixture was stirred at 25° C. for 2 h. A solution of ethyl bromopropionate (0.39 g, 2.2 mmol) in 5 ml anhydrous DMF was then added dropwise. The mixture was stirred for 18 h. The mixture was slowly diluted with 10 ml water. The solution was concentrated in vacuo and the residue purified on a silica gel column, eluting with 2% MeOH/DCM to yield 11-3 (0.42 g, 1.2 mmol, 67%) as an oil.

Step 4:

To a solution of 11-3 (0.42 g, 1.2 mmol) in 10 ml EtOH was added a small scoop of 10% Pd/C. The mixture was stirred at 25° C. under a $H_2$ atmosphere for 18 h. The mixture was then filtered and concentrated in vacuo to yield 11-4 as an oil (0.32 g, 1.2 mmol, 100%).

Data for 11-4: MS: m/z (assignment, relative intensity) 264.1 (M+H$^+$, 95)

Step 5

A solution of 11-4 (0.32 g, 1.2 mmol), 2,6-difluoronitrobenzene (0.23 g, 1.4 mmol), and $Cs_2CO_3$ (0.86 g, 2.6 mmol) in 10 ml DMF was stirred at 60° C. for 5 hours. The mixture was cooled to room temp, filtered and concentrated in vacuo. The residue was chromatagraphed on a silica gel column, eluting with 5% MeOH/DCM to yield 11-5 as an oil (0.34 g, 0.84 mmol, 70%).

Step 6:

To 11-5 (0.32 g, 0.84 mmol) in 5 ml DMF was added DIEA (435 µl, 2.5 mmol) and methylamine (1 ml 2M in THF). The solution was stirred at 25° C. for 18 h. The solution was concentrated in vacuo and the resulting oil was chromatagraphed on a silica gel column, eluting with 5% MeOH/DCM to yield 11-6 as an oil (0.21 g, 0.50 mmol, 60%).

Step 7:

To a solution of 11-6 (0.21 g, 0.50 mmol) in 10 ml THF was added 1 ml acetic acid and 0.50 g of Zn dust. The mixture was stirred at reflux for 30 min. The mixture was filtered and concentrated in vacuo to yield 11-7 as an oil which was used without further purification.

Step 8:

To 11-7 (0.21 g, 0.50 mmol) in 5 ml EtOH was added cyanogen bromide (11.0 ml; 5M in acetonitrile) and stirred at 25° C. for 2 h. The solution was concentrated in vacuo and the resulting oil chromatagraphed on a silica gel column, eluting with 5% MeOH/DCM to 7% MeOH/DCM to yield 11-8 as a foam (0.07 g, 0.18 mmol, 36%).

Step 9:

To 11-8 (0.07 g, 0.18 mmol) in 5 ml THF was added 200 µl of 1N LiOH (aq) and stirred at 25° C. for 18 h. The mixture was concentrated in vacuo and the residue taken up in 7 ml water and treated with 200 µl of 1N HCl (aq). The precipitate was filtered and then treated with 4N HCl/dioxane. Concentration in vacuo yielded 11 as a pale orange solid (28 mg, 0.07 mmol, 38%).

Data for 11: MS: m/z (assignment, relative intensity) 381.3 (M+H$^+$, 90).

Example 12

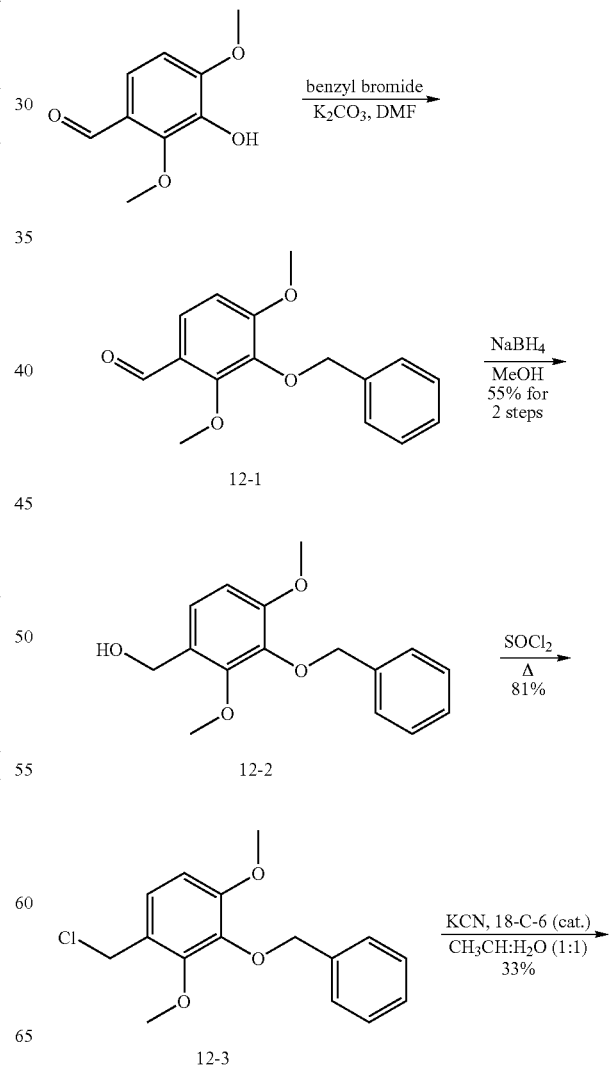

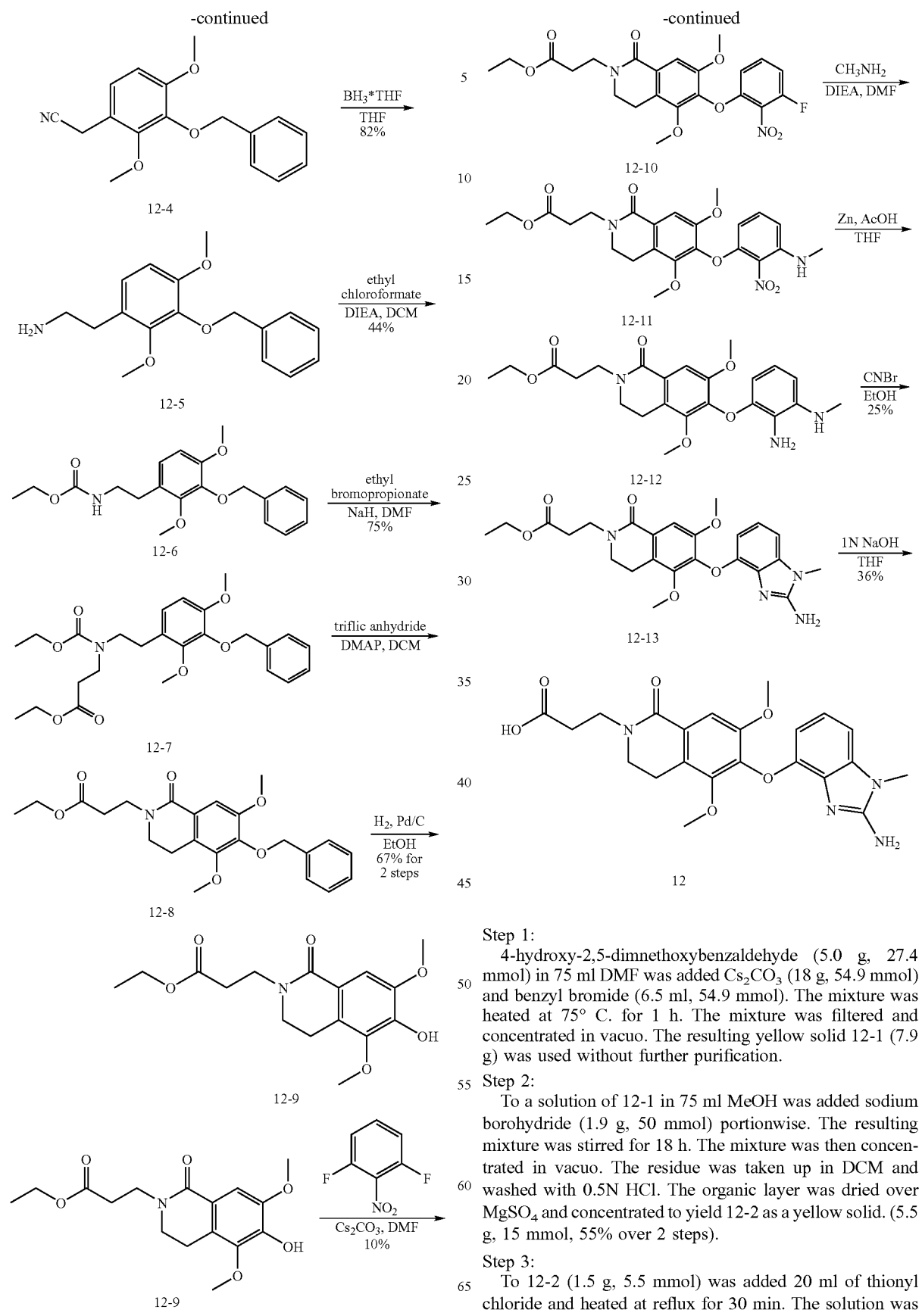

Step 1:
4-hydroxy-2,5-dimethoxybenzaldehyde (5.0 g, 27.4 mmol) in 75 ml DMF was added $Cs_2CO_3$ (18 g, 54.9 mmol) and benzyl bromide (6.5 ml, 54.9 mmol). The mixture was heated at 75° C. for 1 h. The mixture was filtered and concentrated in vacuo. The resulting yellow solid 12-1 (7.9 g) was used without further purification.

Step 2:
To a solution of 12-1 in 75 ml MeOH was added sodium borohydride (1.9 g, 50 mmol) portionwise. The resulting mixture was stirred for 18 h. The mixture was then concentrated in vacuo. The residue was taken up in DCM and washed with 0.5N HCl. The organic layer was dried over $MgSO_4$ and concentrated to yield 12-2 as a yellow solid. (5.5 g, 15 mmol, 55% over 2 steps).

Step 3:
To 12-2 (1.5 g, 5.5 mmol) was added 20 ml of thionyl chloride and heated at reflux for 30 min. The solution was concentrated in vacuo and the residue taken up in DCM and washed with water. The organic layer was dried over MgSO$_4$ and concentrated to yield 12-3 as an oil. (1.3 g, 4.4 mmol, 81%).

Step 4:

To 12-3 (11.0 g, 3.4 mmol) in 20 ml CH$_3$CN:water (1:1) was added potassium cyanide (0.36 g, 5.5 mmol) and a crystal of 18-crown-6. The solution was stirred 18 h. The solution was then concentrated in vacuo and chromatagraphed on a silica gel column, eluting with EtOAc:hexanes (1:1) to yield 12-4 as a solid (0.3 g, 1.1 mmol, 33%).

Step 5:

To 12-4 (0.3 g, 1.1 mmol) in 5 ml anhydrous THF was added BH$_3$-THF (2 ml 1.0M in THF) and stirred for 18 h. The solution was then carefully treated with HCl/EtOH (5 ml, 9% W/V). After 2 h the solution was concentrated in vacuo. The residue was taken up in DCM and washed with 1N NaOH. The organic layer was dried over Na$_2$SO$_4$ and concentrated to yield 12-5 as an oil. (0.25 g, 0.9 mmol, 82%).

Data for 12-5: MS: m/z (assignment, relative intensity) 288.1 (M+H$^+$, 80)

Step 6:

To sodium hydride (70 mg, 1.8 mmol 60% dispersion in oil) under argon was added 12-5 (0.25 g, 0.9 mmol) in 5 ml anhydrous DMF dropwise. After 2 h ethyl 3-bromopropionate (0.18 g, 1.35 mmol) in 5 ml anhydrous DMF was added dropwise. The mixture was stirred for 18 h after which 5 ml 1N HCl was added slowly. The solution was then concentrated in vacuo. The residue was chromatagraphed on a silica gel column, eluting with 2% MeOH/DCM to yield 12-6 as an oil. (155 mg, 0.4 mmol, 44%).

Step 7:

To 12-6 (155 mg, 0.4 mmol) in 5 ml DCM was added DIEA (200 ml, 1.1 mmol) and ethyl chloroformate (100 ml 1.0 mmol). The solution was stirred for 2 h then concentrated in vacuo. The residue was taken up in DCM and washed with 1N NaOH, 1N HCl, and brine. The organic layers were dried over Na$_2$SO$_4$ and concentrated to yield 12-7 as an oil (150 mg, 0.3 mmol, 75%).

Step 8:

To trifluoromethane sulfonic anhydride (0.2 ml, 1.5 mmol) in 2.5 ml anhydrous DCM cooled to 0° C. was added a solution of 12-7 (150 mg, 0.3 mmol) and DMAP (110 mg, 0.9 mmol) in 12 ml anhydrous DCM dropwise. The solution was stirred at 0° C. for 18 h. The solution was then quenched with water and extracted. The organic layer was concentrated in vacuo and chromatagraphed on a silica gel column, eluting with 5% MeOH/DCM. The product 12-8 was then taken up in 5 ml EtOH and a small scoop of 10% Pd/C was added. This mixture was placed under a balloon of hydrogen for 18 h. The mixture was then filtered and concentrated in vacuo to yield 12-9 as an oil (75 mg, 0.2 mmol, 67% for 2 steps).

Step 9:

Following the general procedure described for example 11, step 5, 12-9 was reacted with 2,6-difluoronitrobenzene affording after purification on a silica gel column, eluting with 25% EtOAc/hexanes 10 mg of 12-10 (10%).

Step 10:

Following the general procedure described for example 11, step 6, 12-10 was treated with methylamine to afford 12-11. The crude product was used without purification.

Step 11:

Following the general procedure described for example 11, step 7, 12-11 was treated with Zn and acetic acid in THF to afford 12-12. The crude product was used without purification.

Step 12:

Following the general procedure described for example 11, step 8, 12-12 was treated with cyanogen bromide to afford 12-13 which was chromatagraphed on a silica gel column, elution with 5% MeOH/DCM, to afford 2.5 mg (25% for 3 steps).

Data for 12-13: MS: m/z (assignment, relative intensity) 468.5 (M+H$^+$, 95)

Step 13:

Following the general procedure described for example 11, step 9, 12-13 was treated with 1N NaOH to afford 12 which was purified by preparative HPLC giving 0.8 mg (36%).

Data for 12: MS: t/z (assignment, relative intensity) 441.2 (M+H$^+$, 95)

Example 13

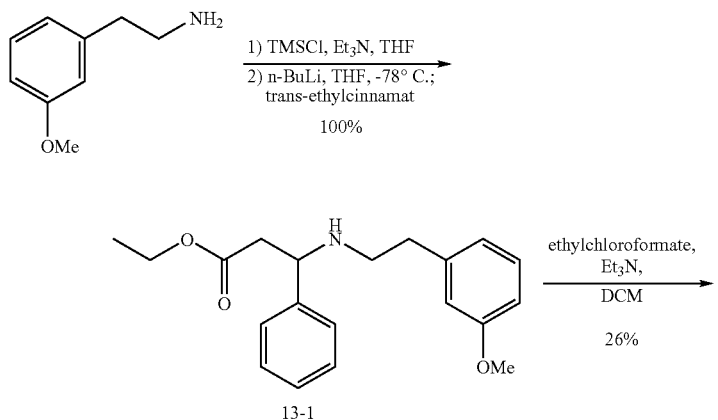

13-1

-continued
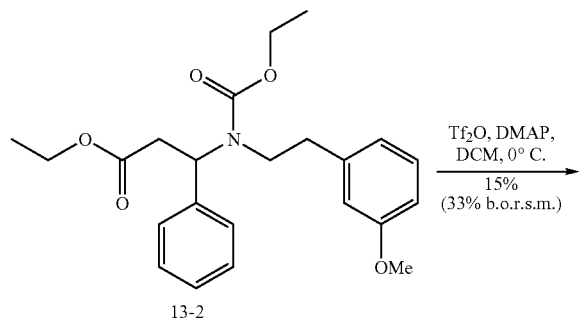
13-2
Tf₂O, DMAP,
DCM, 0° C.
———————→
15%
(33% b.o.r.s.m.)
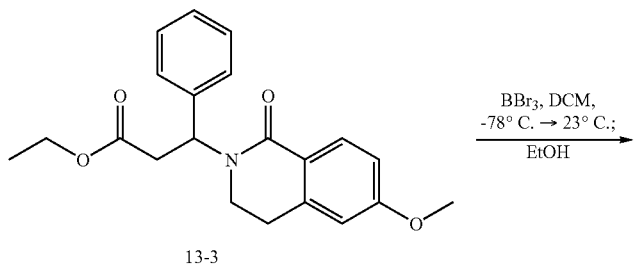
13-3
BBr₃, DCM,
-78° C. → 23° C.;
————————→
EtOH
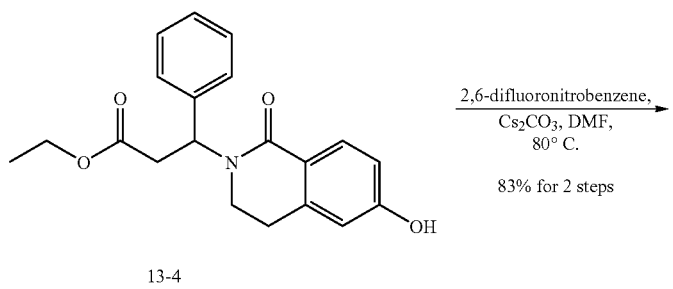
13-4
2,6-difluoronitrobenzene,
Cs₂CO₃, DMF,
80° C.
————————————→
83% for 2 steps
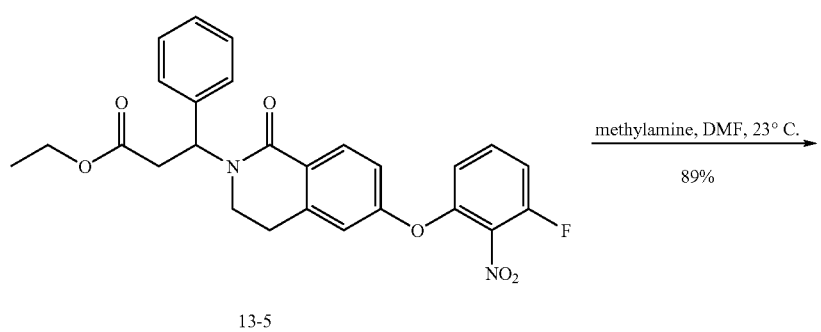
13-5
methylamine, DMF, 23° C.
————————————→
89%
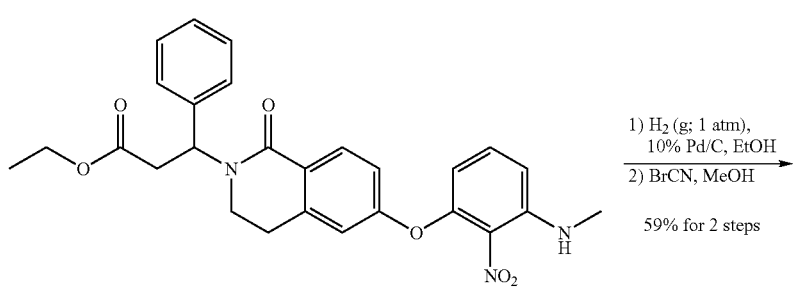
13-6
1) H₂ (g; 1 atm),
10% Pd/C, EtOH
————————→
2) BrCN, MeOH
59% for 2 steps

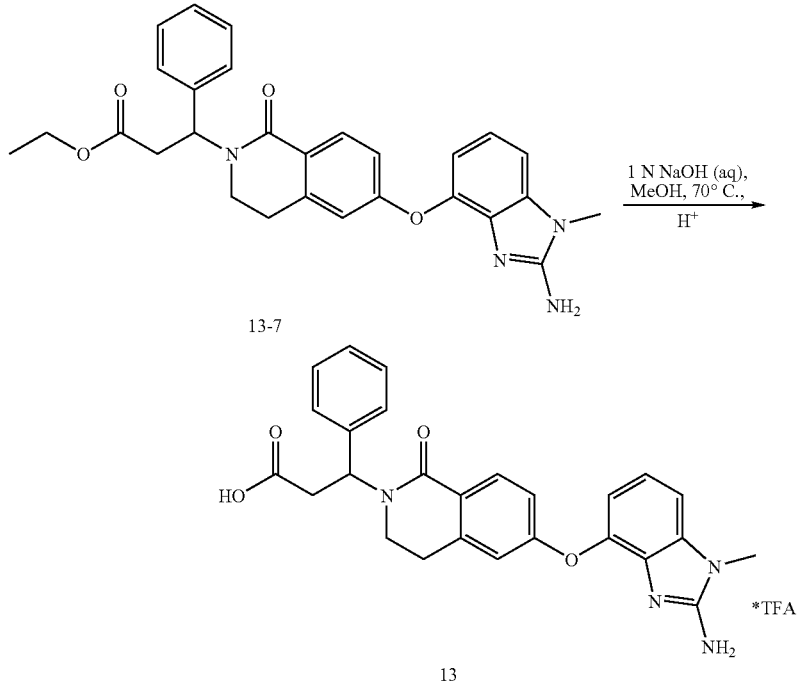

Example 13

Step 1:

To a solution of 3-methoxyphenethylamine (0.5 mL; 3.41 mmol) and triethylamine (0.68 mL; 4.88 mmol) in THF (3 mL) was added TMSCl (0.51 mL; 4.02 mmol). The reaction mixture was stirred for 1 h at room temperature. To the resultant thick slurry was added more THF (3 mL) and then this was filtered through a sintered glass funnel into a 25 mL r.b. flask under a blanket of argon. The resulting clear solution was cooled to −78° C. and n-BuLi (2.5 M; 1 mL; 2.56 mmol) was added and stirred for 15 min at the same temperature. Trans-ethylcinnamate (0.29 mL; 1.71 mmol) was added via cannula as a solution in THF (1 mL) and the mixture stirred for an additional 15 min at −78° C. before quenching with sat. ammonium chloride (aq). The mixture was warmed to room temperature and 1 N HCl (aq) was added forming a thick white precipitate. The mixture was basified to pH 10-11 with 1 N NaOH (aq) and extracted with DCM (3×). The combined organic layers were dried (Na$_2$SO$_4$), filtered and concentrated in vacuo. The crude residue was purified by FCC (silica gel, elution with 2:1 hexanes:EtOAc) giving 560 mg (100%) of 13-1.

Data for 13-1: MS: m/z (assignment, relative intensity) 328.1 (M+H$^+$, 100).

Step 2:

To a solution of 13-1 (610 mg; 1.86 mmol) in DCM (10 mL) at room temperature were added triethylamine (0.39 mL; 2.79 mmol) and ethylchloroformate (0.21 mL; 2.24 mmol). A crystal of DMAP was added and the reaction mixture was stirred at room temperature for 1 h afterwhich more triethylamine (0.39 mL; 2.79 mmol) and ethylchloroformate (0.21 mL; 2.24 mmol) were added. After continuing to stir at room temperature for 3 d, the mixture was concentrated in vacuo and the crude residue was taken up in EtOAc. This was washed with 1 N HCl (aq) (1×20 mL), sat. NaHCO$_3$ (aq) (1×20 mL) and brine (1×20 mL). The organic phase was dried (Na$_2$SO$_4$), filtered and concentrated in vacuo. The crude product was purified by FCC (silica gel, elution with 3:1 hexanes: EtOAc) to afford 190 mg (26%) of ethyl carbamate 13-2.

Step 3:

To a solution of 13-2 (190 mg; 0.48 mmol) and DMAP (183 mg; 1.50 mmol) in DCM (20 mL) at 0° C. was added dropwise triflic anhydride (0.40 mL; 2.40 mmol) as a solution in DCM (4 mL). The resultant cloudy mixture was stirred for an additional 2 h at 0° C. and was then diluted with ether (40 mL) and washed with sat. NaHCO$_3$ (aq) (1×) and 1 N HCl (aq) (1×). The organic phase was dried (Na$_2$SO$_4$), filtered and concentrated in vacuo. The crude mixture was purified by FCC (silica gel, elution with 2:1 hexanes:EtOAc) giving 26 mg (15%) of isoquinolinone 13-3 along with 100 mg of recovered starting material 13-2 (33% based on reacted starting material).

Step 4:

Following the general procedure described for step 2 in example 8, the product from above, 13-3 (35 mg; 0.0991 mmol), was reacted with BBr$_3$ giving phenol 134 which was used in the next step crude without further purification.

Data for 13-4: MS: m/z (assignment, relative intensity) 340.0 (M+H$^+$, 100).

Step 5:

Following the procedure described for step 3 in example 8, the crude product from above, 13-4, was reacted with 2,6-difluoronitrobenzene giving, after purification by FCC (silica gel; elution with 2:1 hexanes:EtOAc), 39 mg (83% for 2 steps) of 13-5.

Step 6:

Following the procedure described for step 4 in example 8, compound 13-5 from above was reacted with methylamine to afford 34 mg (89%) of 13-6 after purification by FCC (silica gel; elution with 2:1 hexanes:EtOAc).

Step 7:

Following the procedure described for step 5 in example 8, compound 13-6 from above was reduced and then reacted with cyanogen bromide to afford, after purification by FCC (silica gel; elution with 5% MeOH/DCM then 10% MeOH/DCM), 20 mg (59% for 2 steps) of aminobenzimidazole 13-7.

Data for 13-7: MS: t/z (assignment, relative intensity) 485.2 (M+H$^+$, 100), 969.0 (2M+H$^+$, 32).

Step 8:

To a solution of ethyl ester 13-7 (20 mg; 0.0413 mmol) in MeOH (2 mL) was added 1 N NaOH (aq) (0.12 mL; 0.12 mmol). The resultant mixture was heated to 70° C. for 3 h. The mixture was then cooled and concentrated in vacuo and the crude material was acidified to pH 2 with 1 N HCl (aq). The mixture was applied to a column filled with Dowex 50 W (H$^+$) ion exchange resin and then eluted with water until the eluent became neutral (pH 6). The column was then eluted with 5% pyridine/H$_2$O. Fraction containing the desired product were pooled and concentrated in vacuo and the zwitterion thus obtained was treated with 50% TFA/DCM and concentrated in vacuo giving 8.3 mg of 13 (33%) as the TFA salt.

Data for 13: MS: m/z (assignment, relative intensity) 457.2 (M+H$^+$, 100), 913.1 (2M+H$^+$, 30).

Example 14

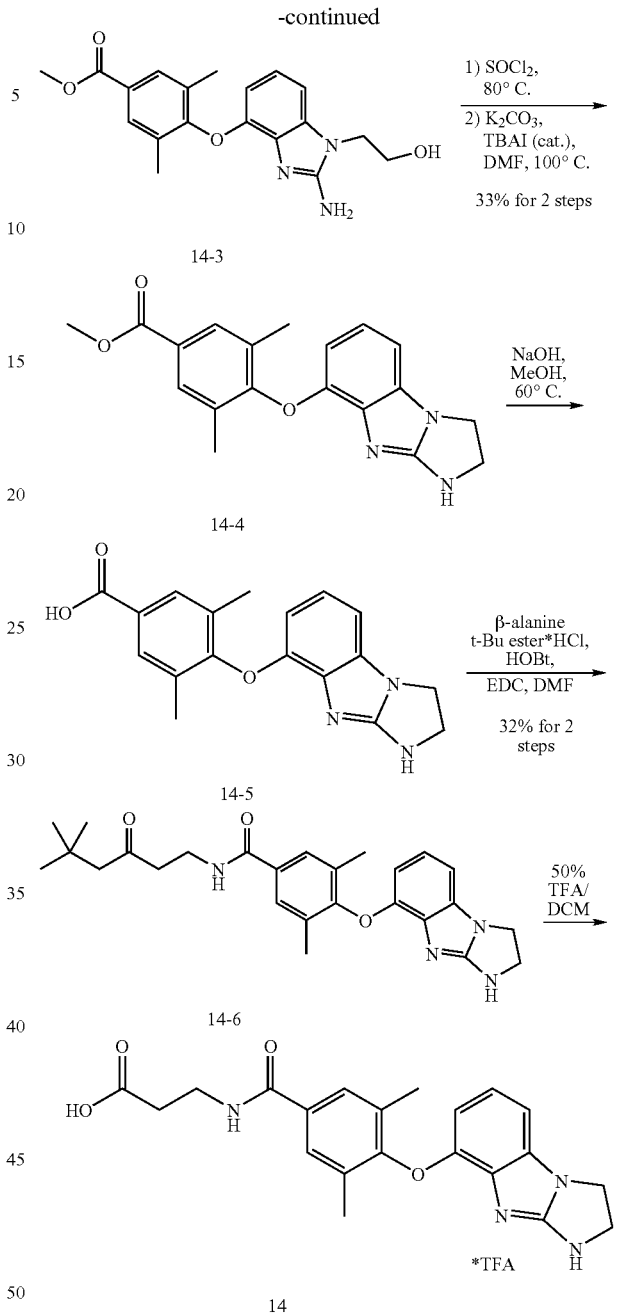

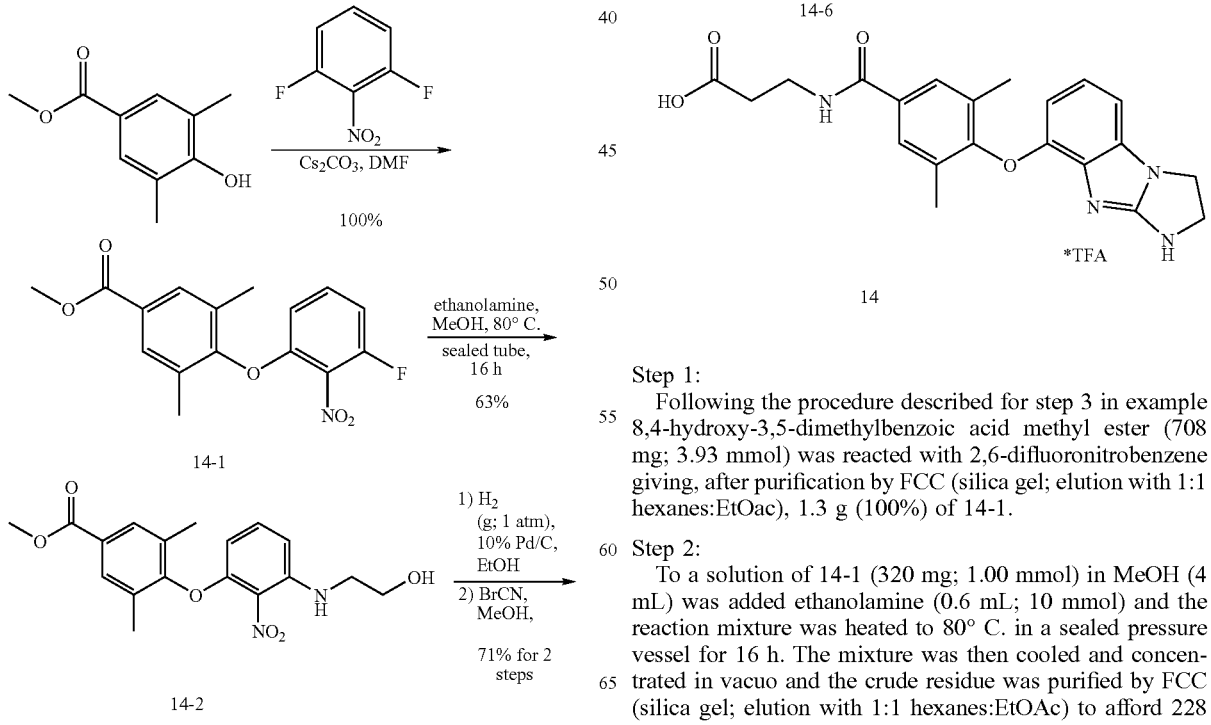

Step 1:

Following the procedure described for step 3 in example 8,4-hydroxy-3,5-dimethylbenzoic acid methyl ester (708 mg; 3.93 mmol) was reacted with 2,6-difluoronitrobenzene giving, after purification by FCC (silica gel; elution with 1:1 hexanes:EtOac), 1.3 g (100%) of 14-1.

Step 2:

To a solution of 14-1 (320 mg; 1.00 mmol) in MeOH (4 mL) was added ethanolamine (0.6 mL; 10 mmol) and the reaction mixture was heated to 80° C. in a sealed pressure vessel for 16 h. The mixture was then cooled and concentrated in vacuo and the crude residue was purified by FCC (silica gel; elution with 1:1 hexanes:EtOAc) to afford 228 mg (63%) of 14-2.

Data for 14-2: MS: m/z (assignment, relative intensity) 361.1 (M+H+, 100).

Step 3:

Following the procedure described for step 5 in example 8, compound 14-2 from above was reduced and then reacted with cyanogen bromide to afford, after purification by FCC (silica gel; elution with 10% MeOH/DCM), 159 mg (71% for 2 steps) of aminobenzimidazole 14-3.

Data for 14-3: MS: m/z (assignment, relative intensity) 356.2 (M+H+, 100).

Step 4:

14-3 (52 mg; 0.146 mmol) was treated with thionyl chloride (1.5 mL) and the resultant mixture was heated to 80° C. for 0.5 h. The mixture was then cooled and concentrated in vacuo and the residue was dissolved in DMF (1.5 mL). To this was added K₂CO₃ (101 mg; 0.73 mmol) and a crystal of tetrabutylammonium iodide and the reaction mixture was heated to 100° C. for 2 d. The mixture was then cooled and partitioned between EtOAc and water. The aqueous phase was extracted with EtOAc (2×) and the organic phases were combined and washed with water (1×) and brine (1×). This was dried (Na₂SO₄), filtered, and concentrated in vacuo and the crude residue was purified by FCC (silica gel; elution with 5% MeOH/EtOAc) giving 16 mg (33% for 2 steps) of 144.

Data for 14-4: MS: m/z (assignment, relative intensity) 338.3 (M+H+, 100).

Step 5:

14-4 (16 mg; 0.0474 mmol) in MeOH (1 mL) was treated with 1 N NaOH (aq) (142 μL; 0.142 mmol) and the reaction mixture heated to 60° C. for 4 h. The mixture was cooled, concentrate in vacuo and treated with 1 N HCl (aq) (142 μL) forming a thick white precipitate which was collected by filtration. The crude acid 14-5 was used in the next step without further purification.

Data for 14-5: MS: m/z (assignment, relative intensity) 324.4 (M+H+, 100).

Step 6:

Following the procedure described for step 1 in example 3, 14-5 was coupled with β-alanine t-Bu ester hydrochloride giving, after purification by FCC (silica gel; elution with 10% MeOH/DCM), 7 mg (32%) of 14-6.

Data for 14-6: MS: m/z (assignment, relative intensity) 451.1 (M+H+, 83), 395.2 (M-tBu, 100), 923.1 (2M+Na+, 17).

Step 7:

14-6 (4 mg; 0.0094 mmol) was treated with 50% TFA/DCM and allowed to stand for 16 h. This was then concentrated in vacuo and triturated with Et2O giving 6.6 mg (84%) of 14 as a TFA salt.

Data for 14: MS: m/z (assignment, relative intensity) 394.44 (M+H+, 100).

Example 15

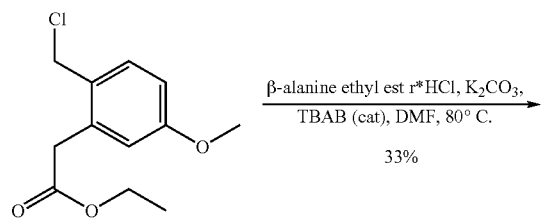

β-alanine ethyl est r*HCl, K₂CO₃, TBAB (cat), DMF, 80° C.

33%

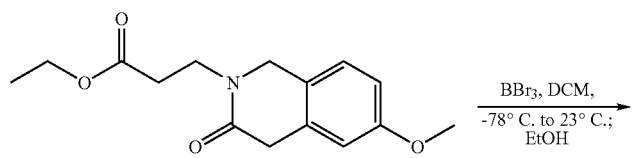

15-1

BBr₃, DCM, −78° C. to 23° C.; EtOH

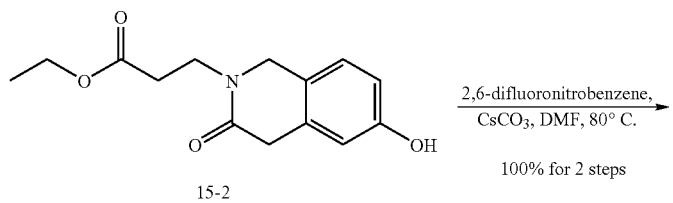

15-2

2,6-difluoronitrobenzene, CsCO₃, DMF, 80° C.

100% for 2 steps

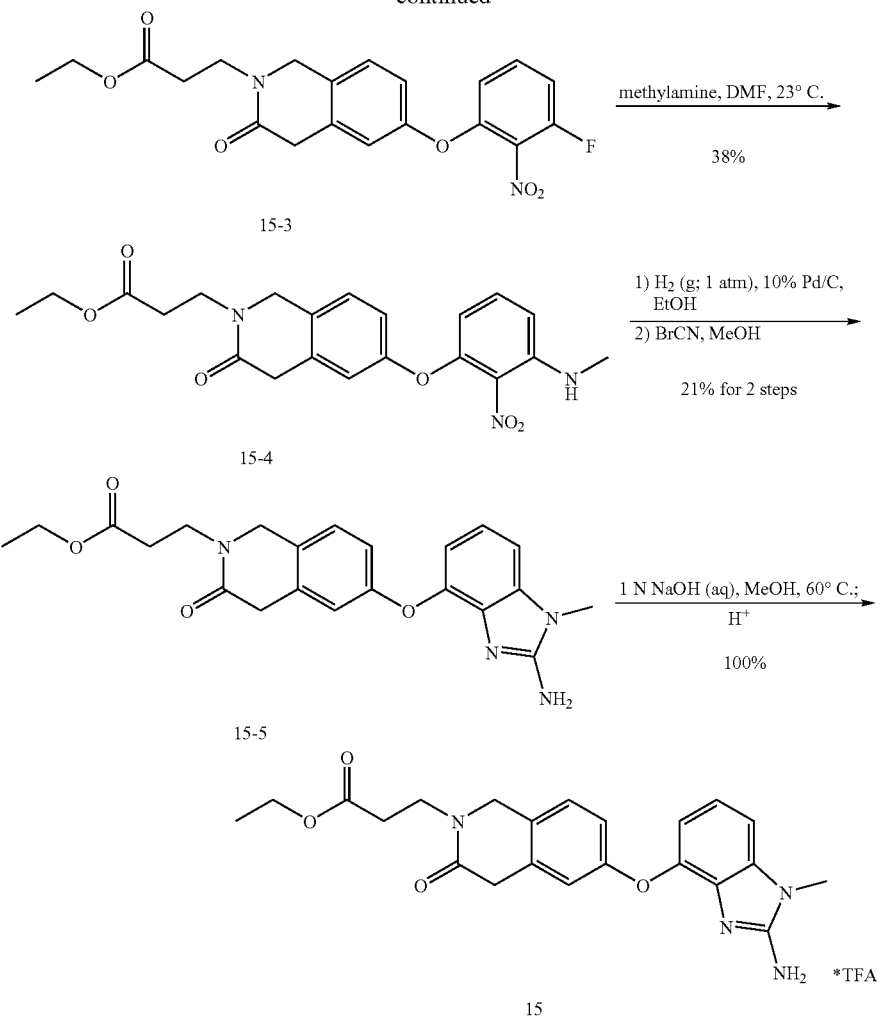

Step 1

To a solution of (2-Chloromethyl-5-methoxy-phenyl)-acetic acid ethyl ester (248 mg; 1.02 mmol) in DMF (1 mL) was added β-alanine ethyl ester hydrochloride (188 mg; 1.23 mmol), $K_2CO_3$ (423 mg; 3.06 mmol), and tetrabutylammonium bromide (small scoop). The reaction mixture was heated to 70° C. for 1 h and then the temperature was increased to 80° C. and stirring was continued for a further 24 h. The mixture was cooled, diluted with EtOAc and washed with 1N HCl (aq) (1×), water (1×) and brine (1×). The organic phase was dried ($Na_2SO_4$), filtered and concentrated in vacuo. The crude residue was purified by FCC (silica gel; elution with 2:1 EtOAc:hexanes) giving 92 mg (33%) of 15-1.

Step 2:

Following the general procedure described for step 2 in example 8, the product from above, 15-1 (50 mg; 0.180 mmol), was reacted with $BBr_3$ giving phenol 15-2 which was used in the next step crude without further purification.

Step 3:

Following the procedure described for step 3 in example 8, the crude product from above, 15-2, was reacted with 2,6-difluoronitrobenzene giving, after purification by FCC (silica gel; elution with 1:2 hexanes:EtOAc), 72 mg (100% for 2 steps) of 15-3.

Data for 15-3: MS: m/z (assignment, relative intensity) 403.2 (M+H$^+$, 80), 425.2 (M-tBu, 45).

Step 4:

Following the procedure described for step 4 in example 8, compound 15-3 from above was reacted with methylamine to afford 28 mg (38%) of 15-4 after purification by FCC (silica gel; elution with 1:2 hexanes:EtOAc).

Step 5:

Following the procedure described for step 5 in example 8, compound 15-4 from above was reduced and then reacted with cyanogen bromide to afford, after purification by FCC (silica gel; elution with 10% MeOH/DCM), 6 mg (21% for 2 steps) of aminobenzimidazole 15-5.

Data for 15-5: MS: m/z (assignment, relative intensity) 409.2 (M+H$^+$, 100).

Step 6:

To a solution of ethyl ester 15-5 (6 mg; 0.0147 mmol) in MeOH (1 mL) was added 1 N NaOH (aq) (44 μL; 0.044 mmol). The resultant mixture was heated to 60° C. for 3 h. The mixture was then cooled and concentrated in vacuo and the crude material was acidified to pH 2 with 1 N HCl (aq). The mixture was applied to a column filled with Dowex 50 W (H+) ion exchange resin and then eluted with water until the eluent became neutral (pH 6). The column was then eluted with 5% pyridine/H₂O. Fractions containing the desired product were pooled and concentrated in vacuo and the zwitterion thus obtained was treated with 50% TFA/DCM and concentrated in vacuo giving 7.5 mg of 15 (100%) as the TFA salt.

Data for 15: MS: m/z (assignment, relative intensity) 381.3 (M+H+, 100).

Example 16

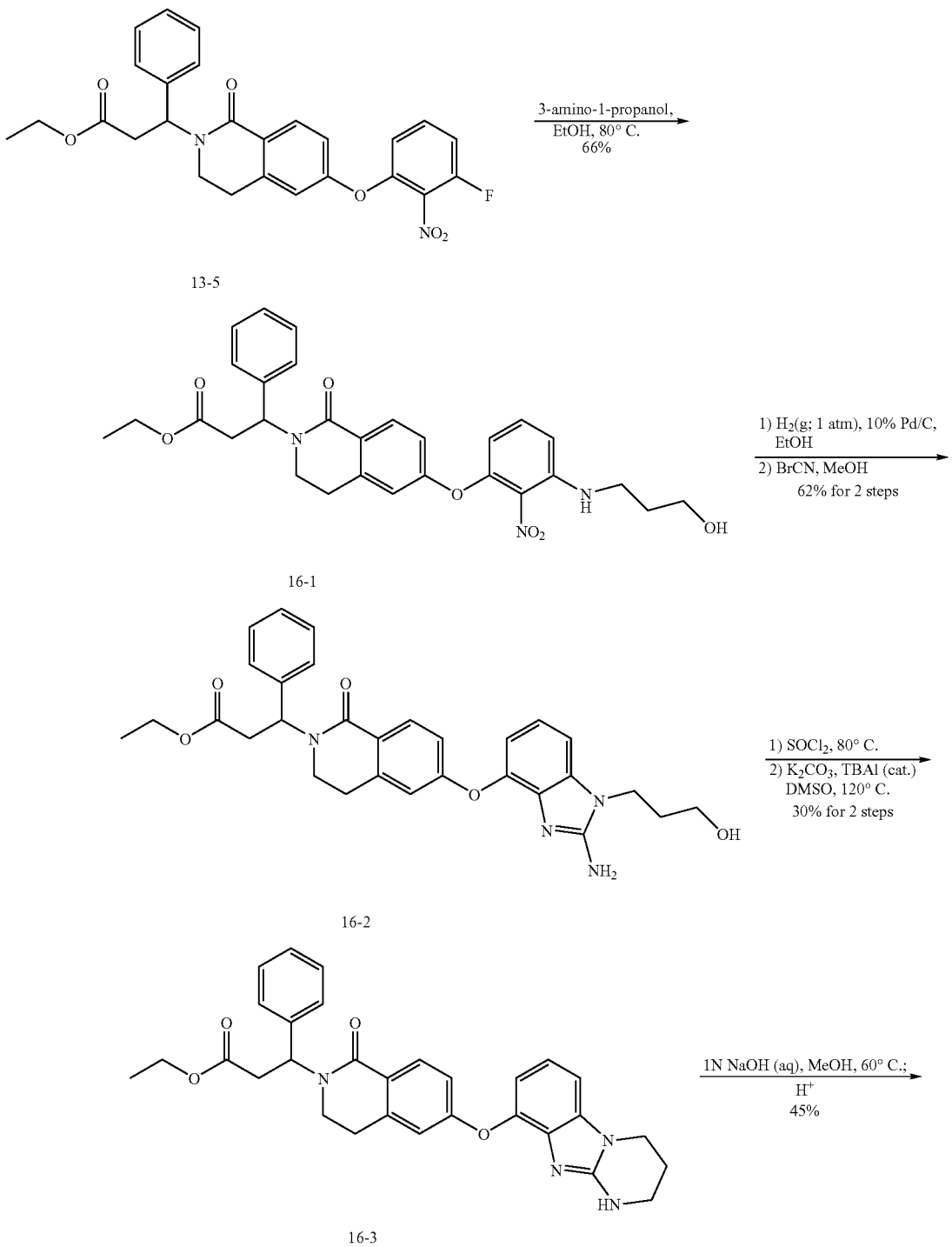

-continued
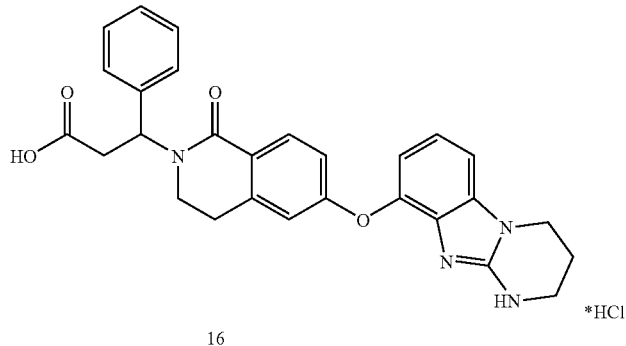
16
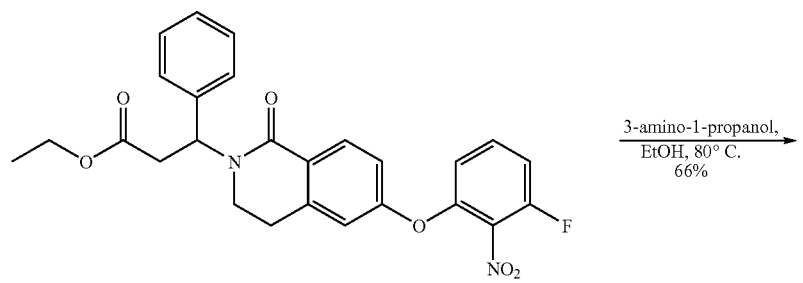
13-5
→ 3-amino-1-propanol,
EtOH, 80° C.
66%
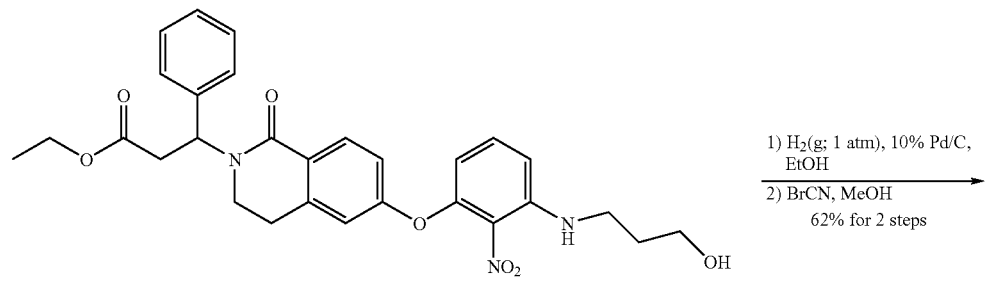
16-1
→ 1) H₂(g; 1 atm), 10% Pd/C, EtOH
2) BrCN, MeOH
62% for 2 steps
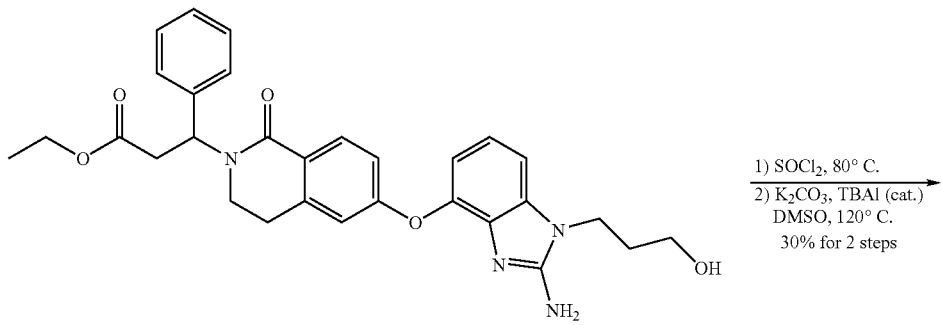
16-2
→ 1) SOCl₂, 80° C.
2) K₂CO₃, TBAI (cat.) DMSO, 120° C.
30% for 2 steps

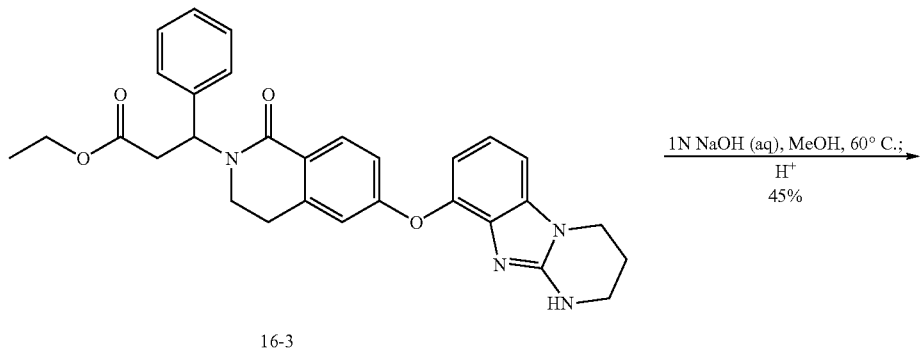

16-3

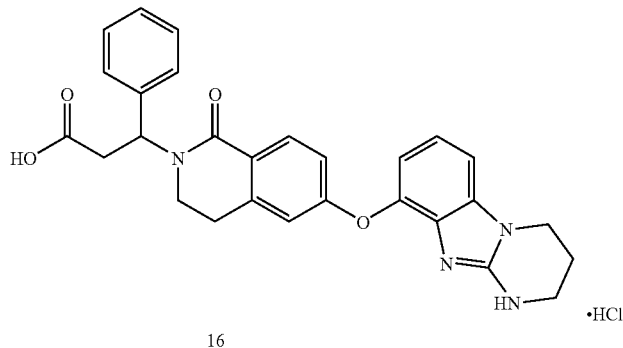

16 ·HCl

Step 1:

To a solution 13-5 [For preparation see example 13 above] (341 mg; 0.713 mmol) in anhydrous EtOH (5 mL) was added 3-amino-1-propanol (0.55 mL; 7.13 mmol). The reaction mixture was heated to 80° C. for 16 h. The mixture was then cooled and concentrated in vacuo. The crude residue was purified by FCC (silica gel; elution with 2:1 EtOAc: hexanes) giving 250 mg of 16-1 (66%).

Step 2:

Following the general procedure described for step 5 in example 8, compound 16-1 from above was reduced and then reacted with cyanogen bromide to afford, after purification by FCC (silica gel; elution with 5% MeOH/DCM then 10% MeOH/DCM), 144 mg (62% for 2 steps) of aminobenzimidazole 16-2.

Data for 16-2: MS: n/z (assignment, relative intensity) 529.2 (M+H$^+$, 100), 1057.0 (2M+H+, 15).

Step 3:

16-2 (100 mg; 0.19 mmol) was treated with thionyl chloride (2 mL) and the resultant mixture was heated to 80° C. for 1 h. The mixture was then cooled and concentrated in vacuo and the residue was dissolved in DMSO (4 mL). To this was added K$_2$CO$_3$ (131 mg; 0.95 mmol) and a small scoop of tetrabutylammonium iodide and the reaction mixture was heated to 135-140° C. for 5 h. The heat was then reduced to 120° C. and stirring was continued for 16 h at this temperature. The mixture was then cooled, diluted with EtOAc (50 mL) and washed with water (2×10 mL) and brine (1×10 mL). The organic phase was dried (Na$_2$SO$_4$), filtered, and concentrated in vacuo. The crude residue was purified by FCC (silica gel; elution with 2% MeOH/DCM then 10% MeOH/DCM) giving 30 mg (30% for 2 steps) of 16-3 along with 27 mg of recovered 16-2 (resulting from hydrolysis of intermediate chloride).

Data for 16-3: MS: m/z (assignment, relative intensity) 511.2 (M+H$^+$, 100), 1020.9 (2M+H$^+$, 25).

Step 4:

To a solution of ethyl ester 16-3 (30 mg; 0.0588 mmol) in MeOH (1 mL) was added 1 N NaOH (aq) (0.2 mL; 0.2 mmol). The resultant mixture was heated to 60° C. for 3 h. The mixture was then cooled and concentrated in vacuo and the crude material was acidified to pH 2 with 1 N HCl (aq). The mixture was applied to a column filled with Dowex 50 W (H$^+$) ion exchange resin and then eluted with water until the eluent became neutral (pH 6). The column was then eluted with 5% pyridine/H$_2$O. Fractions containing the desired product were pooled and concentrated in vacuo and the zwitterion thus obtained was suspended in Et₂O and HCl gas bubbled through to make the HCl salt. This was concentrated in vacuo and dried in a vacuum oven at 60° C. for overnight giving 14 mg of 16 (45%) as the HCl salt.
Data for 16: MS: nzlz (assignment, relative intensity) 483.2 (M+H⁺, 100), 965.0 (2M+H⁺, 8).
Example 17
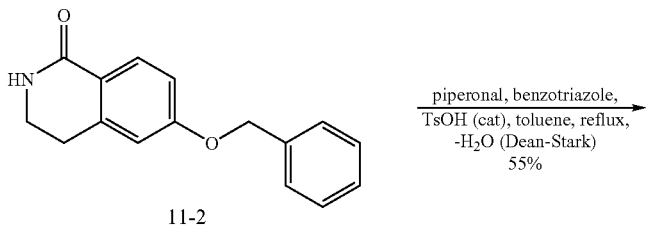
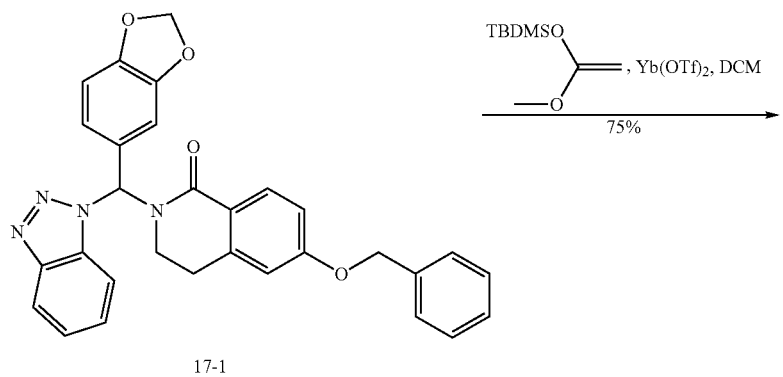
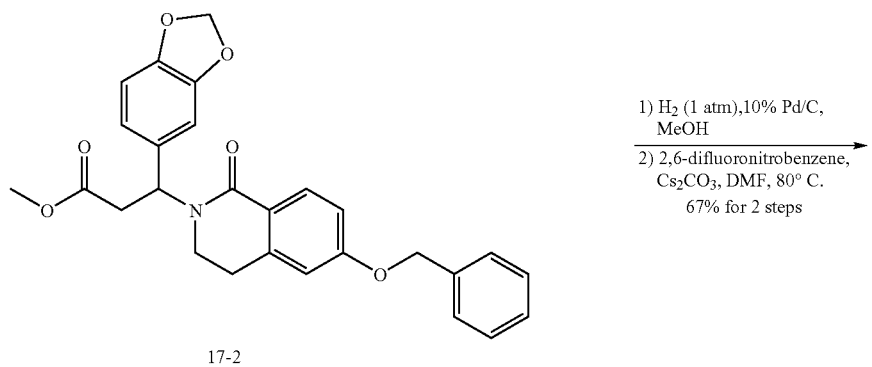
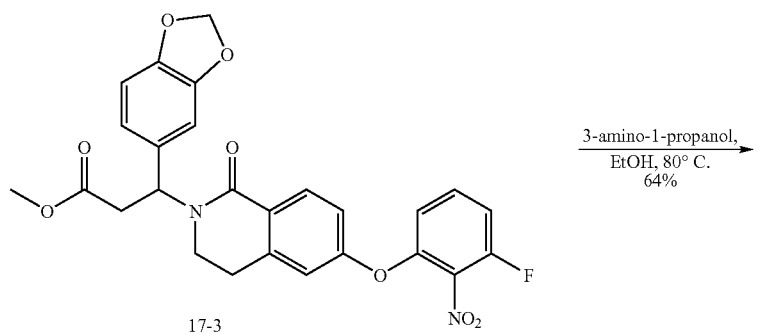

-continued
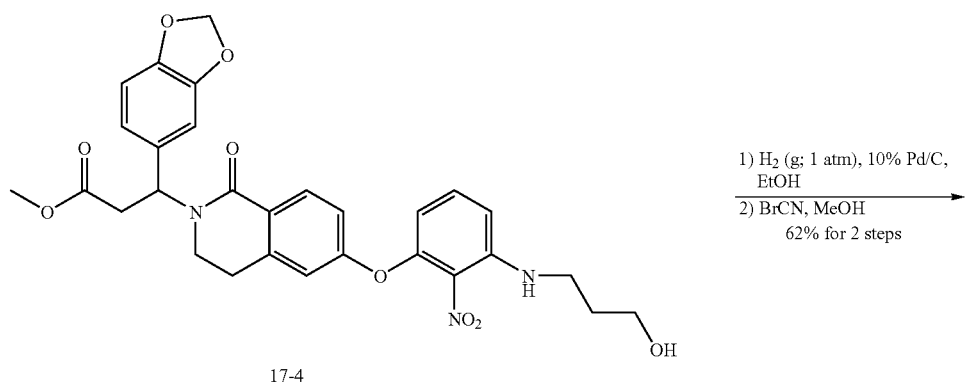
17-4
1) H₂ (g; 1 atm), 10% Pd/C, EtOH
2) BrCN, MeOH
62% for 2 steps
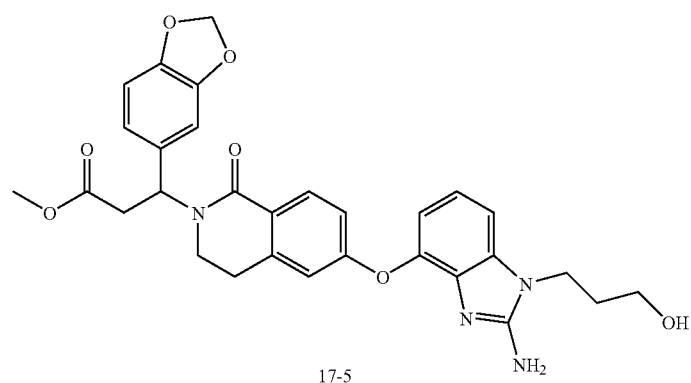
17-5
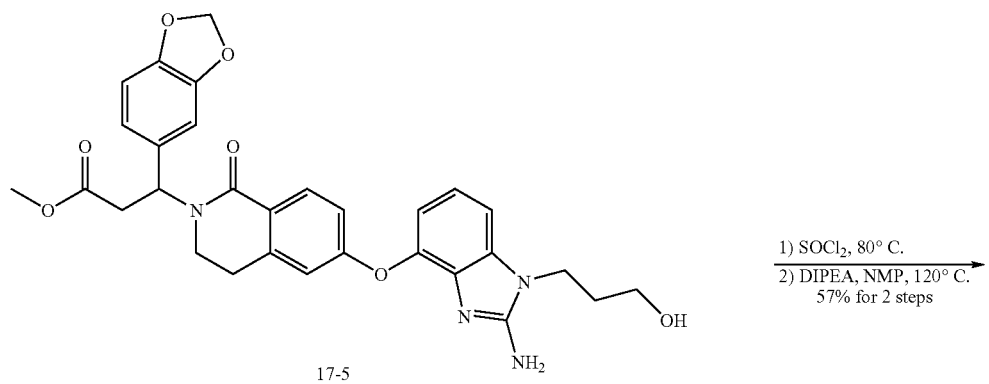
17-5
1) SOCl₂, 80° C.
2) DIPEA, NMP, 120° C.
57% for 2 steps
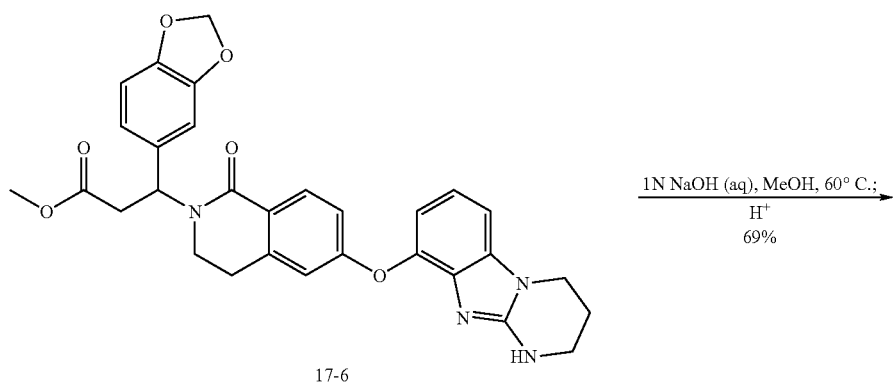
17-6
1N NaOH (aq), MeOH, 60° C.;
H⁺
69%

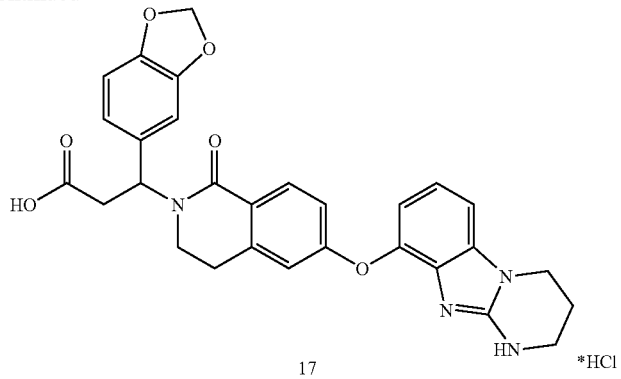

17 *HCl

Step 1:

A mixture of 11-2 [For preparation see example 11 above] (253 mg; 1.00 mmol), piperonal (150 mg; 1 mmol), benzotriazole (119 mg; 1 mmol) and TsOH*H$_2$O (19 mg; 0.1 mmol) was heated to reflux in 5 mL of toluene with a Dean-Stark trap for 16 h. The mixture was cooled, diluted with DCM (100 mL) and washed with 1 N NaOH (aq) (1×50 mL). The aqueous phase was back-extracted with DCM (2×50 mL) and the combined organic phases were dried (Na$_2$SO$_4$), filtered and concentrated in vacuo. The crude residue was purified by FCC (silica gel; elution with 2:1 hexanes:EtOAc) to afford 274 mg (55%) of 17-1.

Step 2:

To a solution of 17-1 (274 mg; 0.544 mmol) in DCM (5 mL) were added ytterbium trifluoromethanesulfonate [Yb(OTf)$_3$] (67 mg; 0.109 mmol) and 1-(tert-butyldimethylsilyloxy)-1-methoxyethene (0.15 mL; 0.815 mmol). The resultant mixture was stirred at room temperature for 16 h. The mixture was then transferred to a separatory funnel and washed with water (1×). The aqueous phase was back-extracted with DCM (2×) and the combined organic phases were dried (Na$_2$SO$_4$), filtered and concentrated in vacuo. The crude residue was purified by FCC (silica gel; elution with 2:1 hexanes:EtOAc) giving 187 mg (75%) of 17-2.

Step 3:

17-2 (187 mg; 0.407 mmol) was debenzylated by hydrogenation in MeOH in the presence of a catalytic amount of 10% Pd/C (1 small scoop) under 1 atm of H$_2$ (g) (balloon) for 3 d. The reaction mixture was filtered through a pad of Celite and concentrated in vacuo. The crude phenol was taken up in DMF (4 mL) and 2,6 difluoronitrobenzene (43 µL; 0.407 mmol) and Cs$_2$CO$_3$ (133 mg; 0.407 mmol) were added. The mixture was heated to 80° C. for 16 h. After cooling to room temperature the mixture was filtered through a pad of Celite, concentrated in vacuo and the crude residue was purified by FCC (silica gel; elution with 3:1 hexanes:EtOAc) to afford 139 mg (67% for 2 steps) of 17-3.

Step 4:

To a solution 17-3 (139 mg; 0.273 mmol) in anhydrous MeOH (3 mL) was added 3-amino-1-propanol (0.21 mL; 2.73 mmol). The reaction mixture was heated to 80° C. for 16 h. The mixture was then cooled, concentrated in vacuo and partitioned between EtOAc and water. The aqueous phase was extracted with EtOAc (1×) and the combined organic phases were then washed with water (1×) and brine (1×). The organic phase was then dried (Na$_2$SO$_4$), filtered and concentrated in vacuo. The crude residue was purified by FCC (silica gel; elution with 3:1 EtOAc:hexanes) giving 98 mg (65%) of 17-4.

Step 5:

Following the general procedure described for step 5 in example 8, compound 17-4 from above was reduced and then reacted with cyanogen bromide to afford, after purification by FCC (silica gel; elution with 5% MeOH/DCM then 10% MeOH/DCM), 63 mg (65% for 2 steps) of aminobenzimidazole 17-5.

Data for 17-5: MS: m/z (assignment, relative intensity) 559.2 (M+H$^+$, 100), 1116.9 (2M+H+, 36).

Step 6:

17-5 (63 mg; 0.113 mmol) was treated with thionyl chloride (3 mL) and the resultant mixture was heated to 80° C. for 45 min. The mixture was then cooled and concentrated in vacuo and the residue was dissolved in NMP (2.5 mL). To this was added a scoop of 4 A molecular sieves and DIPEA (98 µL; 0.563 mmol) and the reaction mixture was heated to 120° C. for 6.5 h. More DIPEA (98 µL; 0.563 mmol) was then added and the mixture was heated at 120° C. for an additional 9 h. The mixture was then cooled and partitioned between EtOAc and water. The aqueous phase was extracted with EtOAc and the organic phases were combined and washed with water (1×) and brine (1×). The organic phase was dried (Na$_2$SO$_4$), filtered, and concentrated in vacuo. The crude residue was purified by FCC (silica gel; elution with 2% MeOH/DCM then 5% MeOH/DCM) giving 35 mg (57% for 2 steps) of 17-6.

Data for 17-6: MS: m/z (assignment, relative intensity) 541.2 (M+H$^+$, 100).

Step 7:

To a solution of methyl ester 17-6 (35 mg; 0.0647 mmol) in MeOH (2 mL) was added 1 N NaOH (aq) (0.32 mL; 0.32 mmol). The resultant mixture was heated to 60° C. for 1.5 h. The mixture was then cooled to room temperature and stirring continued for 16 h. The mixture was then warmed back to 60° C. for an additional 1 h, cooled and concentrated in vacuo. The crude material was acidified to pH 5 with 1 N HCl (aq) (0.32 mL; 0.32 mmol) forming a white precipitate which was collected by filtration and washed with cold water. The material thus obtained was treated with 2 N HCl in Et₂O, concentrated in vacuo, and then dried in a vacuum oven at 70° C. for 3 h to give 25 mg of 17 (69%) as the HCl salt.
Data for 17: MS: m/z (assignment, relative intensity) 527.1 (M+H$^+$, 100), 1052.8 (2M+H$^+$, 45).
Example 18
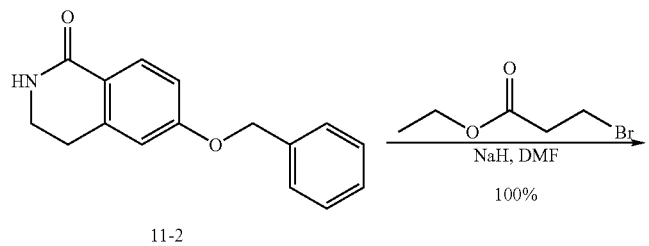
11-2
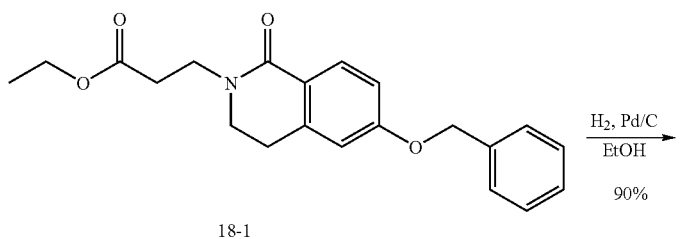
18-1
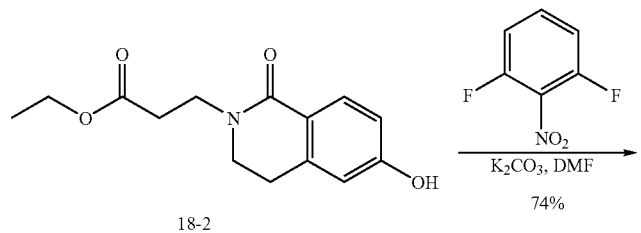
18-2
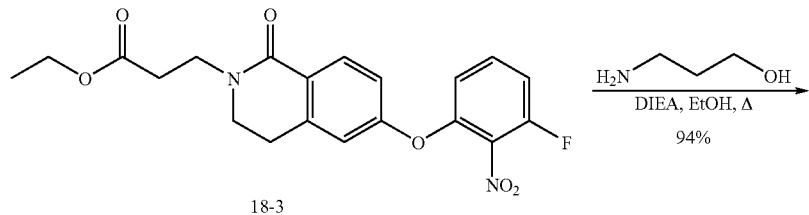
18-3
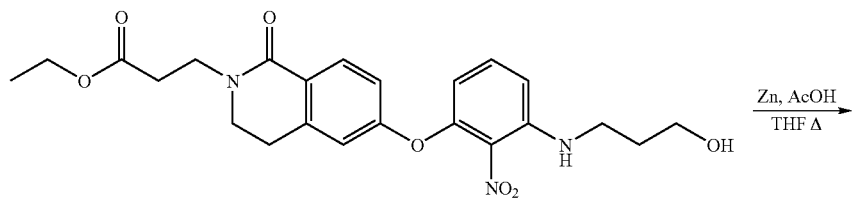
18-4
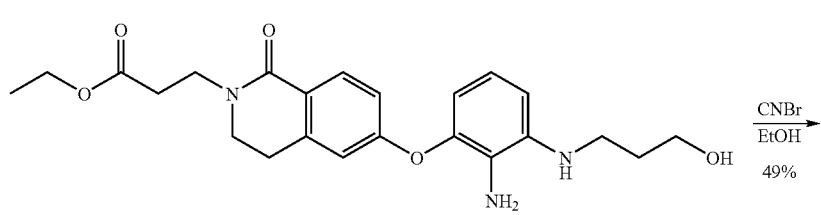
18-5

-continued

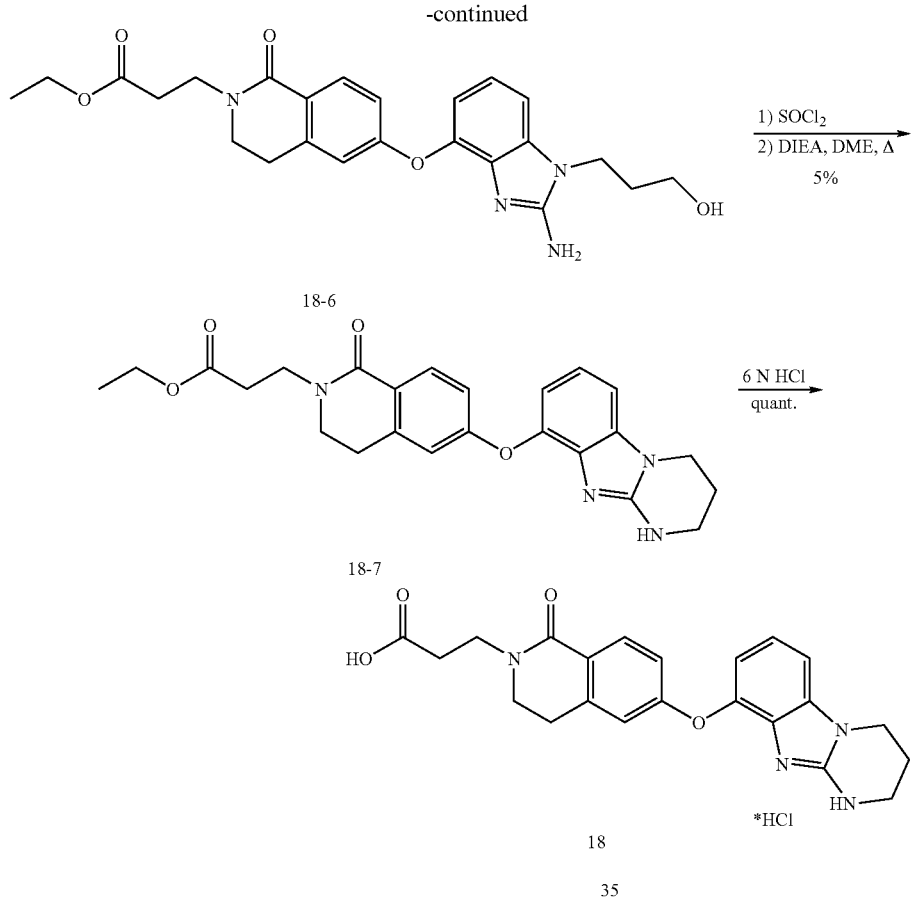

Step 1:
To 11-2 [For preparation see example 11 above] (0.25 g, 1 mmol) in 10 ml dry DMF was added NaH (0.08 g, 2 mmol). After 2.5 hours ethylbromopropionate (0.36 g, 2 mmol) in 5 ml dry DMF was added dropwise. After 2 hours the reaction was quenched with 0.1N HCl and concentrated in vacuo. The residue was purified on a silica gel column, eluting with 5% MeOH/DCM to yield 18-1 (0.36 g, 1 mmol, 100%) as an oil.

Step 2:
To 18-1 in 5 ml EtOH was added a small scoop of 10% Pd/C and placed under a $H_2$ balloon. The mixture was stirred at room temperature for 18 hours. The mixture was then filtered and concentrated in vacuo to yield 18-2 (0.24 g, 0.9 mmol, 90%) as an oil.

Step 3:
A mixture of 18-2 (0.24 g, 0.9 mmol), 2,6-difluoronitrobenzene (0.24 g, 1.5 mmol), and $K_2CO_3$ (0.28 g, 2 mmol) was stirred at 80° C. in 10 ml DMF for 18 hours. The mixture was then filtered and concentrated in vacuo to yield 18-3 (0.27 g, 0.67 mmol, 74%) as an oil which was used without further purification.

Step, 4:
A solution of 18-3 (0.27 g, 0.67 mmol), 3-amino-1-propanol (0.51 ml, 6.7 mmol) and DIEA (0.57 ml, 3.3 mmol) was heated to reflux in DME for 2 hours. The solution was then concentrated in vacuo and the residue purified on a silica gel column, eluting with 5% MeOH/DCM to yield 18-4 (0.29 g, 0.63 mmol, 94%) as an oil.

Step 5:
To 18-4 (0.29 g, 0.64 mmol) in 15 ml TH was added 2 ml acetic acid and 0.5 g of zinc dust. The mixture was heated at reflux for 15 minutes. The mixture was cooled to room temperature, filtered and concentrated. He residue was taken up in DCM and washed with 1N NaOH and brine, dried over $MgSO_4$ and concentrated to yield 18-5 which was used without further purification.

Step 6:
To crude 18-5 in 110 ml EtOH was added cyanogen bromide (00.10 g, 1 mmol) and stirred at room temperature for 18 hours. The solution was then concentrated and the residue purified on a silica gel column, eluting with 7% MeOH/DCM to yield 18-6 (0.14 g, 0.31 mmol, 49%) as an oil.

Step 7:
To 18-6 was added 10 ml $SOCl_2$ and stirred at room temperature for 30 minutes. The solution was concentrated, taken up in 15 ml DME and basified with DIEA. The solution was then heated at reflux for 48 hours. The solution was then concentrated and the residue purified on a silica gel column, eluting with 10% MeOH/DCM. The resulting oil was then purified further by preparative HPLC to yield 18-7 (0.007 g, 0.016 mmol, 5%) as an oil.

Step 8:
18-7 (4 mg, 0.009 mol) was treated with 4 ml 6N HCl for 18 hours. The mixture was then concentrated in vacuo to yield 18 (4 mg, 0.009 mmol, 100%) as a white solid.

Data for 18: MS: m/z (assignment, relative intensity) 407.2 (M+H⁺, 95)

Example 19

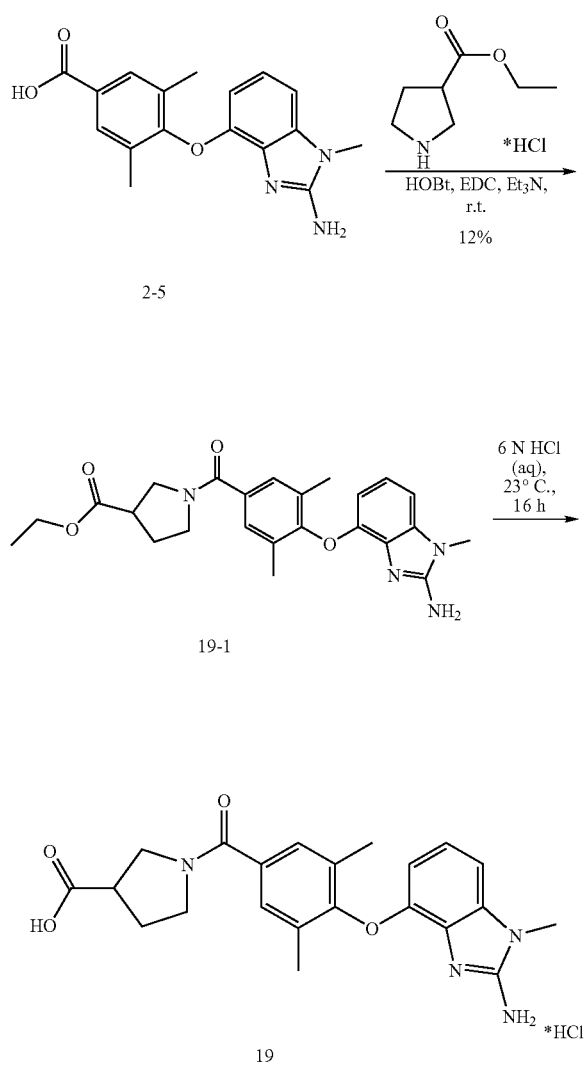

Step 1:

To a solution of 2-5 (87 mg; 0.28 mmol) in DMF (1 mL) were added triethylamine (194 μL; 1.4 mmol), 1-hydroxybenzotriazole (56.7 mg; 0.42 mmol), 1-[3-(dimethylamino)propyl]-3-ethylcarbodiimide hydrochloride (80.5 mg; 0.42 mmol) and pyrrolidine-3-carboxylic acid ethyl ester (50 mg; 0.35 mmol). The reaction mixture was stirred at room temperature overnight. Then the mixture was partitioned between EtOAc and water. The aqueous phase was extracted with EtOAc (3×). The organic phases were combined and concentrated in vacuo. The residue was purified by FCC (silica gel; elution with 10% MeOH/DCM) giving 15 mg (12%) of 19-1.

Data for 19-1: MS: m/z (assignment, relative intensity) 437.2 (M+H$^+$, 100).

Step 2:

19-1 (15 mg; 0.034 mmol) was treated with 1 mL of 6 N HCl (aq) and stirred at room temperature for 16 h. This was then concentrated in vacuo and dried in a vacuum oven at 60° C. for 16 h giving 15 mg (100%) of 19.

Data for PS580985: MS: m/Lz (assignment, relative intensity) 409.2 (M+H$^+$, 100).

A good review of the demonstrated utility in vivo of vitronectin antagonists is provided by Miller et al. [*Drug Discovery Today* 5, 397-408 (2000)]. The article is incorporated herein by reference. The article describes a number of compounds that have been tested in vivo for the treatment of osteoporosis, tumors, rheumatoid arthritis, and restenosis based on their vitronectin inhibitory activity in vitro. Therefore compounds showing the vitronectin inhibitory activity in vitro described below would be expected by persons of skill to exhibit utility for these conditions in vivo.

The compounds were tested according to the following procedure:

Assays of human placental $\alpha_v\beta_3$ and $\alpha_v\beta_5$ were performed as described in the literature [Pytela et al. "Methods In Enzymology, 144, 475-489 (1987)] with minor modification. Time-resolved fluorescence was used as an alternative to colorimetric detection to improve the assay sensitivity and the signal to noise ratio. In the assay, 75 ng of either $\alpha_v\beta_3$ or $\alpha_v\beta_5$ was coated on the microtiter wells. Various concentrations of the test compound were added, together with 5 mmol of europium-labeled vitronectin. The samples were allowed to incubate at room temperature for one hour. Following incubation, the wells were emptied and washed. The amount of europium-labeled vitronectin bound to the plate was determined by time-resolved fluorescence measurement. A 384 well plate was coated by incubating each well with 25 μL of a 3 μg per mm solution of $\alpha_v\beta_3$ (75 ng per well) in buffer A. Buffer A is an aqueous solution containing 50 mmol tris-hydrochloride, 100 mmol sodium chloride, 1 mmol magnesium chloride, 1 mmol magnesium chloride, 1 mmol calcium chloride, 1 mmol manganese chloride adjusted to pH7.4. The plate was incubated overnight at 4° C. 70 μL of 1% bovine serum albumin (BSA) per well was added and the plate incubated for three hours at room temperature, followed by washing three times with 70 μL of Buffer A per well. To each well was added 15 μL of a solution of test compound in 46 μL of buffer A containing 1% dimethylsulfoxide, 20 mmol diethylenetriaminepentaacetic acid (DTPA) and 0.05% BSA (1-5 μM final concentration of test compound). Also added was 5 μL of 20 nm Eu$^{3+}$ vitronectin in Buffer A with 20 mmol DTPA and 0.05% BSA (to a 5 nm final concentration). The plate was incubated for one hour at room temperature and washed three times with 70 μL each of Buffer A. Twenty-five μL of a standard fluorescence enhancement solution was added and the fluorescence measured and compared to control. The IC$_{50}$ of a test compound represents the concentration of that compound required to suppress fluorescence by 50%.

All of the compounds of the preceding examples and in the following table, which were made by analogous procedures, exhibited IC$_{50}$'s below 1 μM against $\alpha_v\beta_3$ integrin and below 10 μM against $\alpha_v\beta_5$ integrin.

| Example number | Structure |
|---|---|
| 20 | 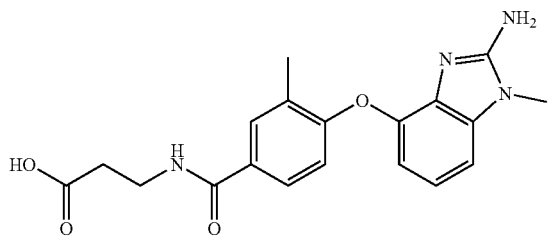 |
| 21 | 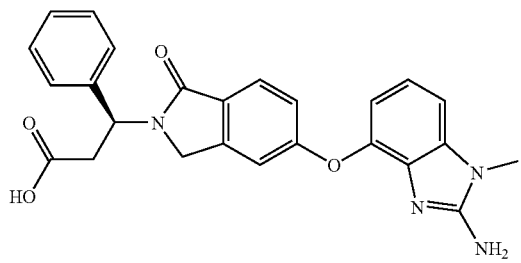 |
| 22 | 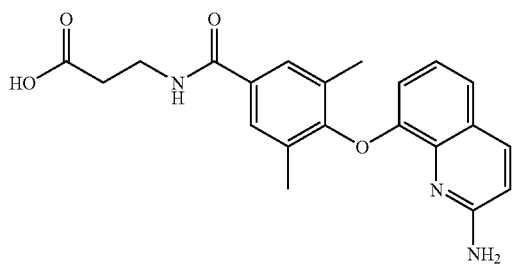 |
| 23 | 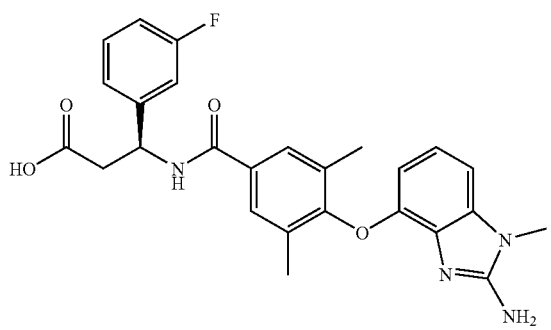 |
| 24 | 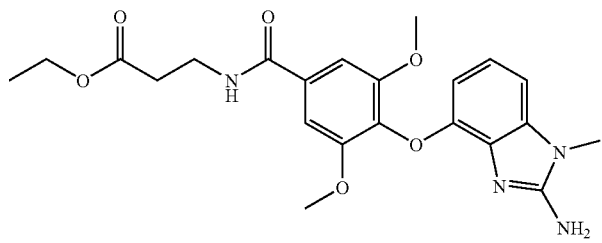 |

-continued
| Example number | Structure |
|---|---|
| 25 | 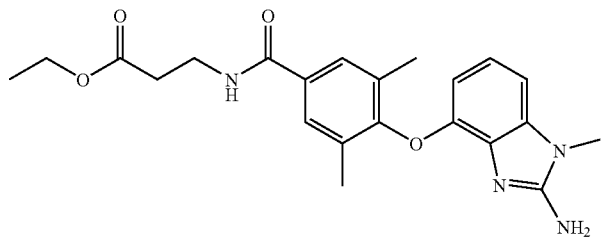 |
| 26 | 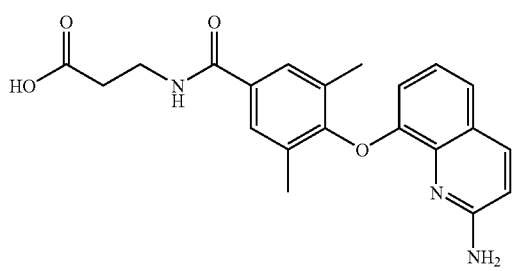 |
| 27 | 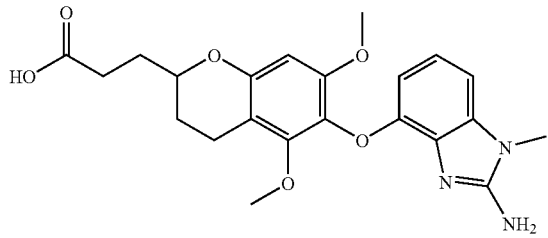 |
| 28 | 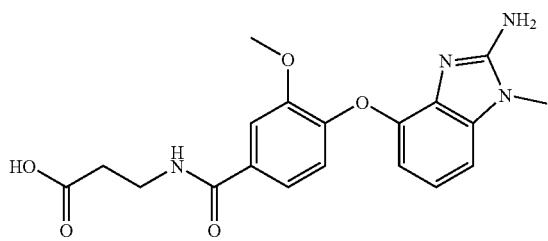 |
| 29 | 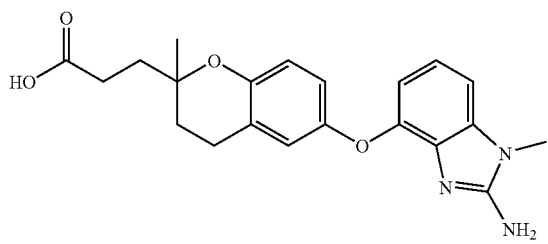 |

-continued
| Example number | Structure |
|---|---|
| 30 | 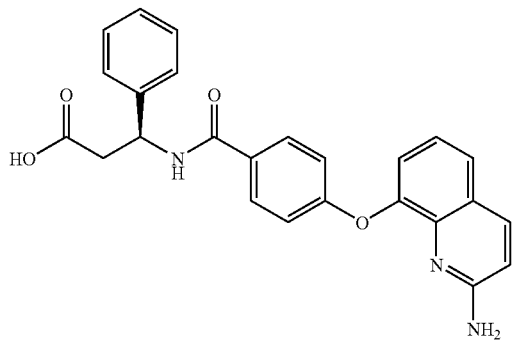 |
| 31 | 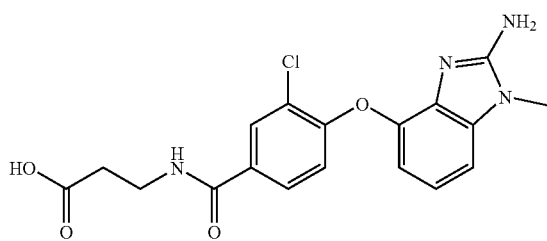 |
| 32 | 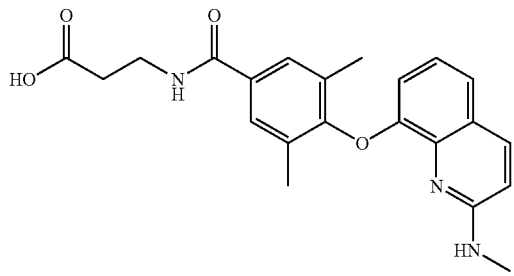 |
| 33 | 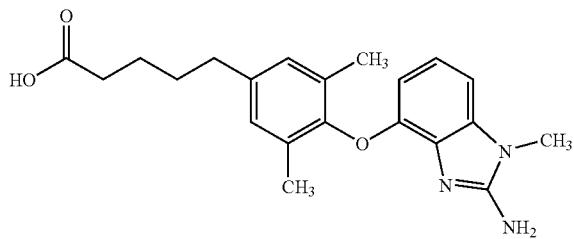 |
| 34 | 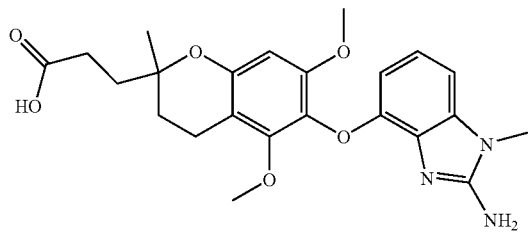 |

-continued
| Example number | Structure |
|---|---|
| 35 | 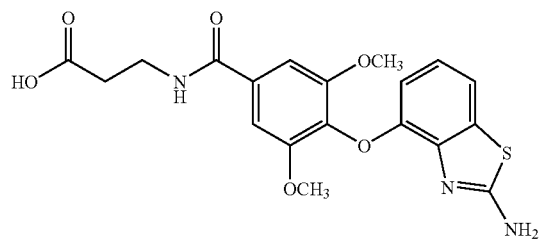 |
| 36 | 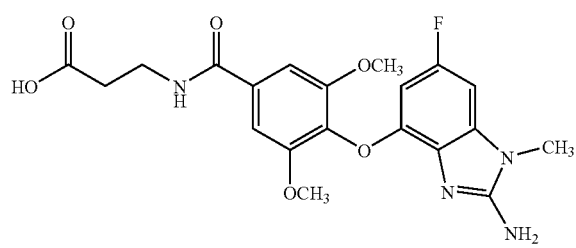 |
| 37 | 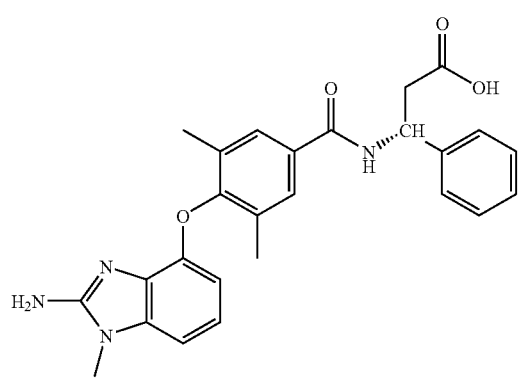 |
| 38 | 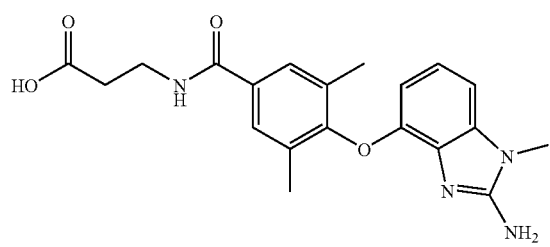 |
| 39 | 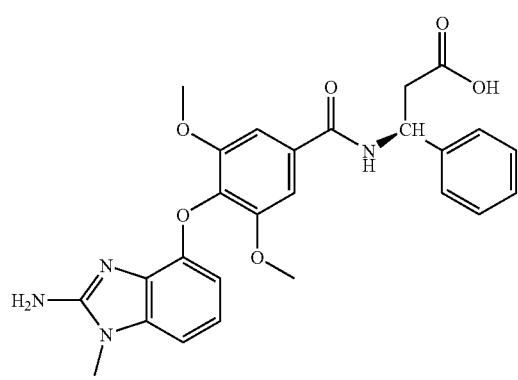 |

-continued
| Example number | Structure |
|---|---|
| 40 | 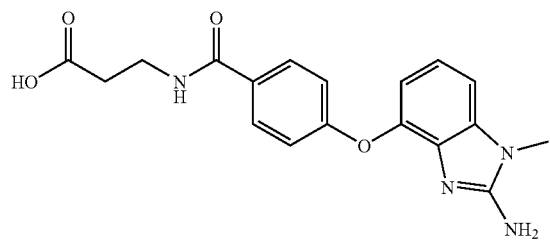 |
| 41 | 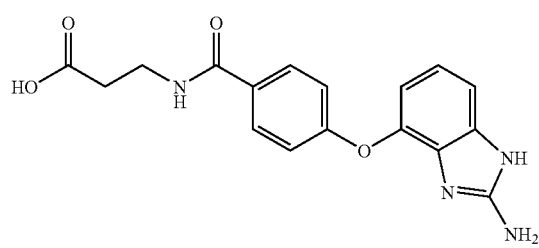 |
| 42 | 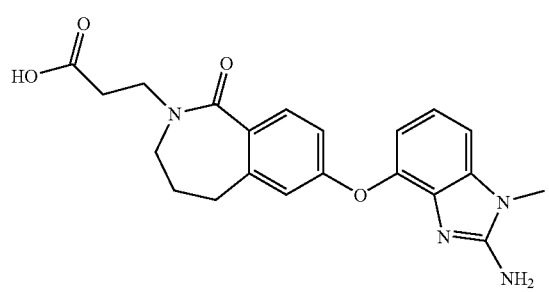 |
| 43 | 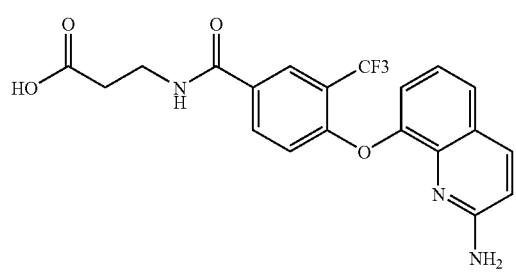 |
| 44 | 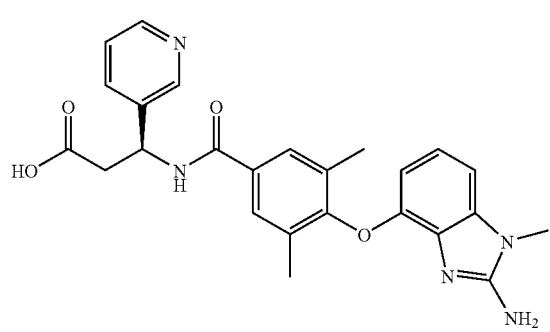 |

| Example number | Structure |
|---|---|
| 45 | 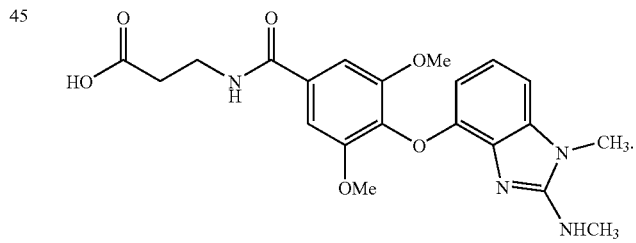 |
| 46 | 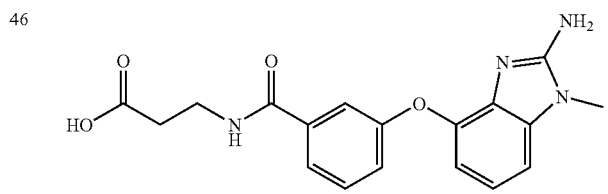 |
| 47 | 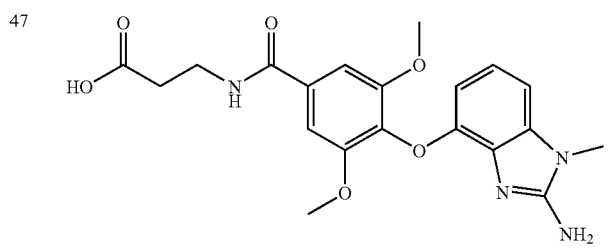 |
| 48 | 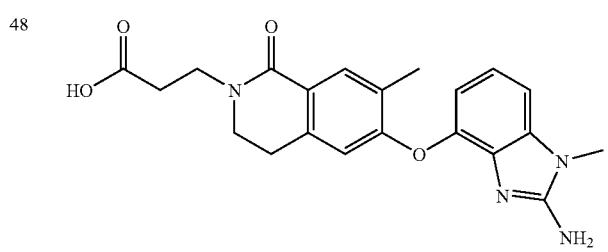 |
| 49 | 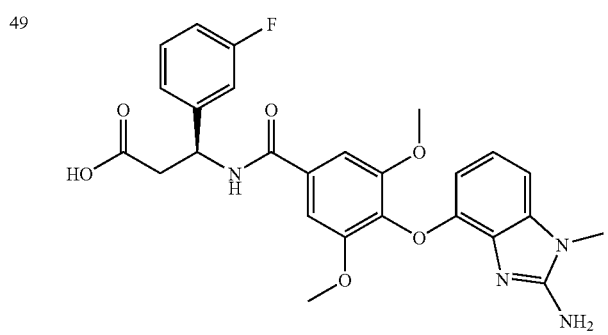 |
| 50 | 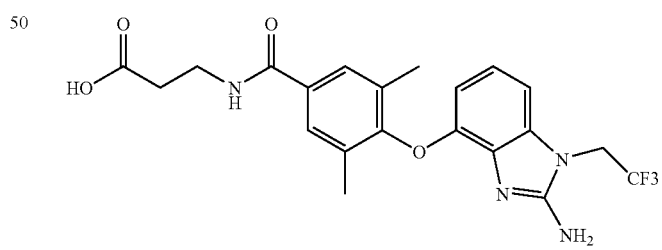 |

-continued

| Example number | Structure |
|---|---|
| 51 | 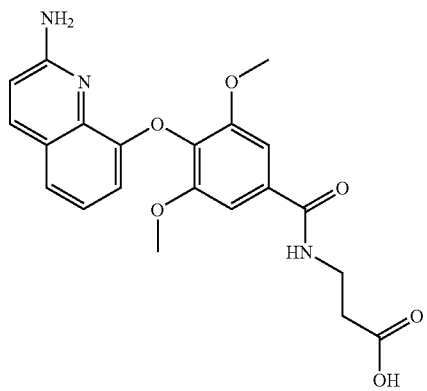 |
| 52 | 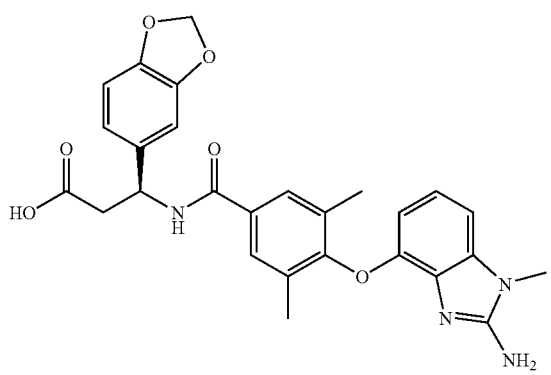 |
| 53 | 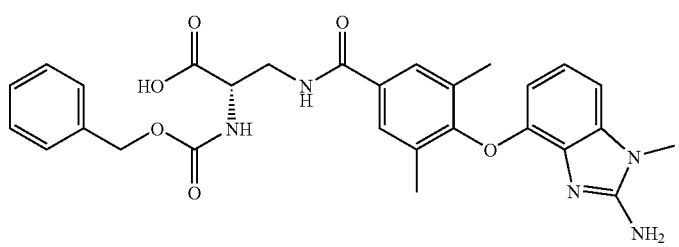 |

What is claimed is:

1. A compound of formula:

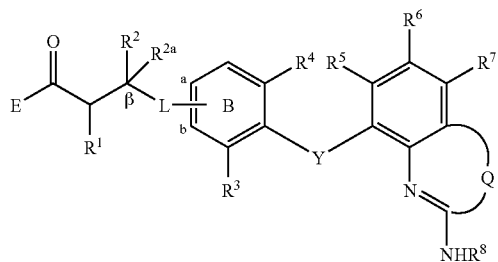

wherein

Y is chosen from the group consisting of —O—, —S—, —SO$_2$—, —CH$_2$— and —N(loweralkyl)-;

L is a linker, said linker comprising from one to eight carbons and from zero to three nitrogens, sulfurs and oxygens, wherein at least two atoms are interposed between ring B and carbon β, said linker being straight chain, branched or cyclic, and, when cyclic, attached either at carbons a and b of ring B or, when $R^1$ is methylene, at $R^1$;

Q is $NR^9$;

E is hydroxy, or E is a biolabile residue such that E and the carboxyl to which it is attached together form an ester or amide cleavable in vivo to provide a compound in which E is hydroxy;

$R^1$ is chosen from the group consisting of hydrogen, aryl, heteroaryl, ($C_1$ to $C_6$) hydrocarbon, substituted aryl, ($C_1$ to $C_3$)alkylaryl, —NHCOOR$^{10}$, —NHSO$_2$R$^{10}$ and —NHCOR$^{10}$;

$R^2$ is chosen from the group consisting of hydrogen, aryl, heteroaryl, ($C_1$ to $C_6$) hydrocarbon, substituted aryl, ($C_1$ to $C_3$)alkylaryl, —NHCOOR$^{10}$, —NHSO$_2$R$^{10}$ and —NHCOR$^{10}$, and R$^{2a}$ is hydrogen; or taken together R$^2$ and R$^{2a}$ form a carbonyl;

R$^3$ and R$^4$ are independently chosen from the group consisting of hydrogen, ($C_1$ to $C_4$) hydrocarbon, loweralkoxy, halogen and fluoro(loweralkyl);

R$^5$, R$^6$ and R$^7$ are independently chosen from the group consisting of hydrogen, halogen and fluoro(loweralkyl);

R$^8$ is chosen from hydrogen and lower alkyl; and

R$^9$ is chosen from hydrogen, alkyl, substituted alkyl, aryl and ($C_1$ to $C_3$) akylaryl; or taken together R$^8$ and R$^9$ represent a two to four carbon chain forming a five to seven membered cyclic structure, which may contain one degree of unsaturation; and R$^{10}$ is chosen from the group consisting of alkyl, substituted alkyl, aryl and ($C_1$ to $C_3$)alkylaryl.

2. A compound according to claim 1 of formula:

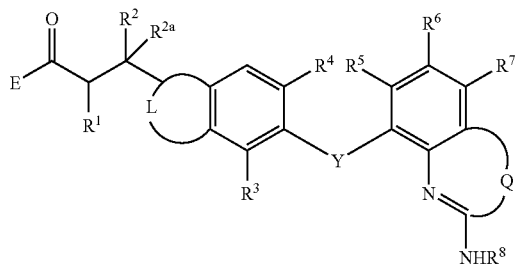

wherein L is a cyclic linker forming a five-, six or seven-membered ring, optionally substituted with one or two substituents chosen from lower alkyl and oxo.

3. A compound according to claim 2 of formula:

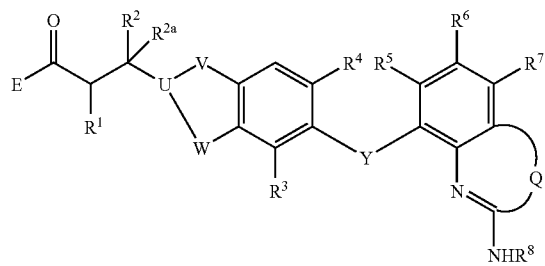

wherein
U is chosen from the group consisting of CH, C(CH$_3$) and N;
V is chosen from the group consisting of C=O, CH$_2$ and O;
W is chosen from the group consisting of (CH$_2$)$_n$C=O, C(=O)(CH$_2$)$_n$, (CH$_2$)$_n$CH$_2$, O(CH$_2$)$_n$ and (CH$_2$)$_n$O; and
n is zero, one or two.

4. A compound according to claim 3 of formula:

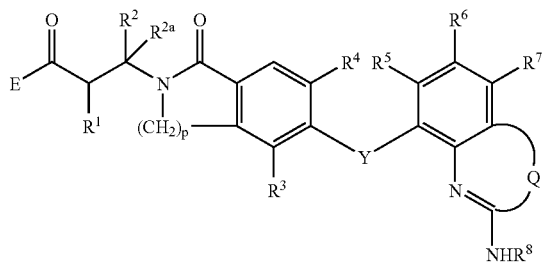

wherein p is one, two or three;

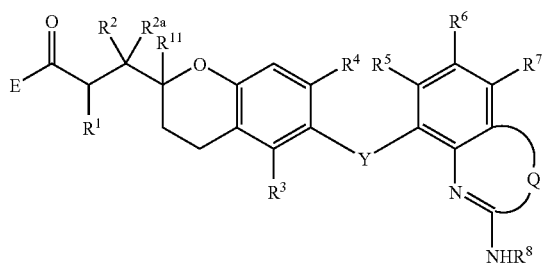

wherein R$^{11}$ hydrogen or methyl;

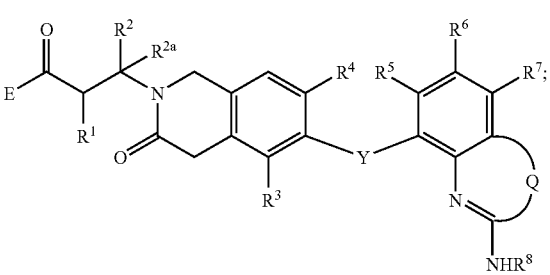

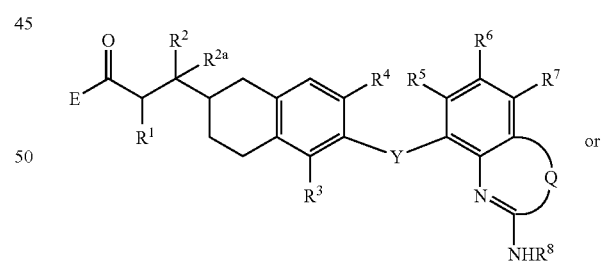 or

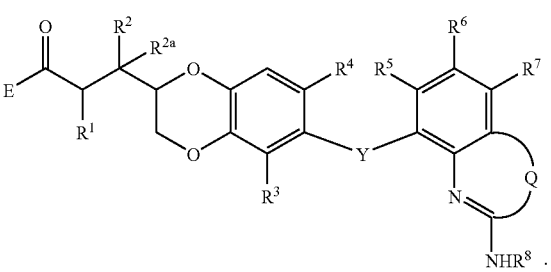

5. A compound according to claim 1 of formula:

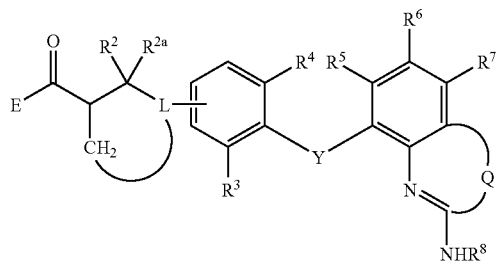

6. A compound according to claim 5 of formula:

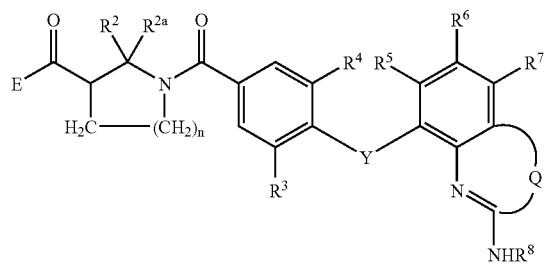

wherein n is zero, one or two.

7. A compound according to claim 1 of formula:

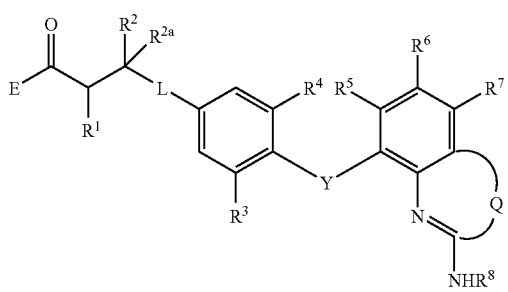

wherein L is a linker comprising from one to four carbons and from zero to three nitrogens, sulfurs and oxygens, in a straight or branched chain.

8. A compound according to claim 1 of formula:

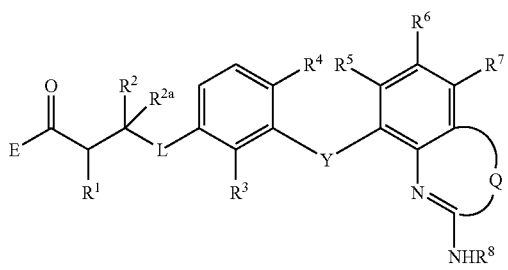

wherein L is a linker comprising from one to eight carbons and from zero to three nitrogens, sulfurs and oxygens, in a straight or branched chain.

9. A compound according to claim 1 of formula:

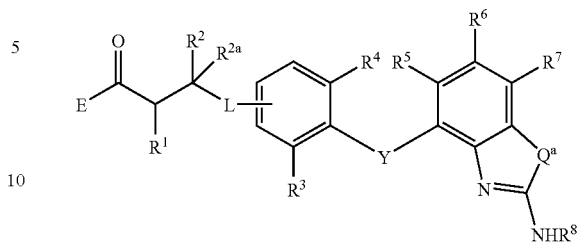

wherein $Q^a$ is $NR^9$, and $R^9$ is chosen from hydrogen, alkyl, aryl, ($C_1$ to $C_3$)alkylaryl and alkyl substituted with methoxy, fluoro or hydroxy.

10. A compound according to claim 1 of formula:

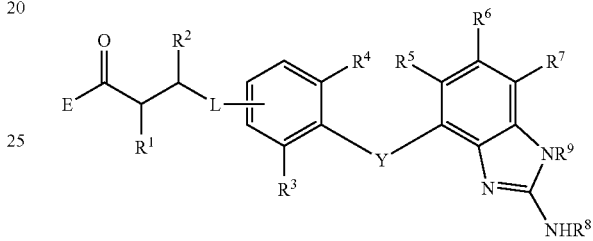

wherein $R^9$ is chosen from hydrogen, lower alkyl, and fluoro (loweralkyl).

11. A compound according to claim 1 of formula

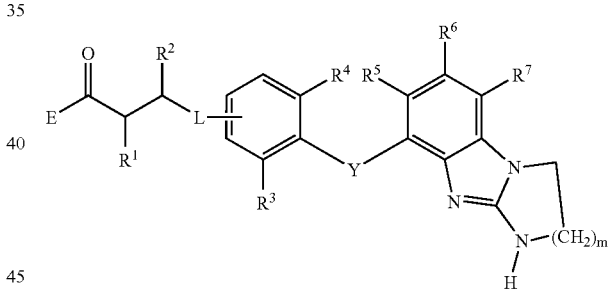

wherein m is one or two.

12. A compound according to claim 9 of formula:

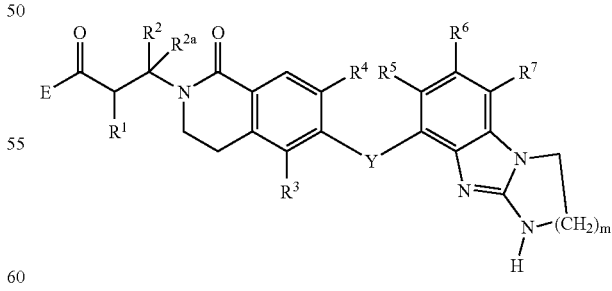

wherein m is one or two.

13. A compound according to any of claims 1 to 12 wherein E is hydroxy.

14. A compound according to claim 1 wherein $R^2$ and $R^{2a}$ are hydrogen and $R^1$ is chosen from hydrogen, —NHCOOR$^{10}$, —NHCOR$^{10}$ and —NHSO$_2$R$^{10}$.

15. A compound according to claim 1 wherein $R^1$ is other than hydrogen and the carbon to which $R^1$ is attached is of the configuration shown:

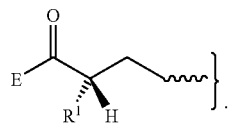

16. A compound according to claim 1 wherein $R^2$ is hydrogen, $C_1$-$C_6$ hydrocarbon, aryl, substituted aryl or heteroaryl.

17. A compound according to claim 1 wherein $R^1$ is hydrogen, $R^{2a}$ is hydrogen and $R^2$ is other than hydrogen, and the carbon to which $R^2$ is attached is of the configuration shown:

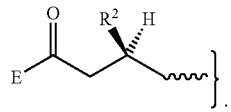

18. A compound according to claim 1 wherein $R^3$ and $R^4$ are chosen from hydrogen, methyl, methoxy, halogen and trifluoromethyl.

19. A compound according to claim 1 wherein $R^5$ and $R^7$ are hydrogen.

20. A compound according to claim 1 wherein $R^8$ chosen from hydrogen and methyl.

21. A compound according to claim 1 wherein L is chosen from —C(=O)NH—, —CH=CH— and —CH$_2$CH$_2$—.

22. A compound according to any of claims 1 to 12 wherein Y is —O—.

23. A compound according to claim 22 wherein
E is hydroxy
$R^1$ hydrogen, —NHCOOR$^{10}$ or —NHCOR$^{10}$;
$R^2$ is hydrogen, aryl, heteroaryl or substituted aryl;
$R^3$ $R^4$ are chosen from hydrogen, methyl, methoxy, halogen and trifluoromethyl;
$R^5$ $R^7$ are hydrogen; and
$R^8$ is chosen from hydrogen and methyl.

24. A compound according to claim 13 wherein Y is —O—.

25. A pharmaceutical composition comprising a compound according to claim 1 and pharmaceutically acceptable carrier.

* * * * *

UNITED STATES PATENT AND TRADEMARK OFFICE
CERTIFICATE OF CORRECTION

PATENT NO. : 7,365,209 B2
APPLICATION NO. : 10/775963
DATED : April 29, 2008
INVENTOR(S) : Letourneau et al.

It is certified that error appears in the above-identified patent and that said Letters Patent is hereby corrected as shown below:

Title page, item [75] under the Inventors:

Delete "Yaing Rong," and insert -- Yajing Rong, --

In the Claims:

Claim 20, Col. 92, Line 6: Delete "wherein $R^8$ chosen" and insert -- $R^8$ is chosen --

Claim 23, Col. 92, Line 14: Delete "$R^1$ hydrogen," and insert -- $R^1$ is hydrogen, --

Claim 23, Col. 92, Line 16: Delete "$R^3$ $R^4$ are" and insert -- $R^3$ and $R^4$ are, --

Claim 23, Col. 92, Line 18: Delete "$R^5$ $R^7$ are hydrogen; and" and insert -- $R^5$ and $R^7$ are hydrogen; --

Signed and Sealed this

Eighth Day of July, 2008

JON W. DUDAS
*Director of the United States Patent and Trademark Office*